(12) United States Patent
McAlister

(10) Patent No.: US 9,222,704 B2
(45) Date of Patent: Dec. 29, 2015

(54) GEOTHERMAL ENERGIZATION OF A NON-COMBUSTION CHEMICAL REACTOR AND ASSOCIATED SYSTEMS AND METHODS

(71) Applicant: McAlister Technologies, LLC, Phoenix, AZ (US)

(72) Inventor: Roy Edward McAlister, Phoenix, AZ (US)

(73) Assignee: McAlister Technologies, LLC, Phoenix, AZ (US)

( * ) Notice: Subject to any disclaimer, the term of this patent is extended or adjusted under 35 U.S.C. 154(b) by 0 days.

(21) Appl. No.: 14/251,433

(22) Filed: Apr. 11, 2014

(65) Prior Publication Data

US 2014/0219904 A1    Aug. 7, 2014

Related U.S. Application Data

(60) Division of application No. 13/764,107, filed on Feb. 11, 2013, now Pat. No. 8,734,546, which is a continuation-in-part of application No. 13/584,688, filed on Aug. 13, 2012.

(60) Provisional application No. 61/523,266, filed on Aug. 12, 2011.

(51) Int. Cl.
*C01B 31/02* (2006.01)
*C01B 31/04* (2006.01)
(Continued)

(52) U.S. Cl.
CPC ............... *F24J 3/08* (2013.01); *B01J 19/0053* (2013.01); *C01B 31/02* (2013.01); *C01B 31/04* (2013.01);
(Continued)

(58) Field of Classification Search
CPC ........ C01B 31/02; C01B 31/04; C01B 31/36; F24J 2/07; F24J 2/12; F24J 2/5266; F24J 3/085
See application file for complete search history.

(56) References Cited

U.S. PATENT DOCUMENTS 3,613,792 A   10/1971   Hyde et al.
3,633,372 A    1/1972   Kimmel et al.
(Continued)

FOREIGN PATENT DOCUMENTS

CA    2521698 A1    8/2005
CH     692927 A5   12/2002
(Continued)

OTHER PUBLICATIONS

"Carnot Thermochemical Cycles." Digital image. Wikipedia, the Free Encyclopedia, Published: Aug. 31, 2010. Accessed: Jan. 4, 2011. Printed: May 20, 2011. <http://en.wikipedia.org/wiki/File:Carnot_thermochemical_cycles.PNG>. p. 1.
(Continued)

*Primary Examiner* — Matthew Merkling
(74) *Attorney, Agent, or Firm* — Perkins Coie LLP

(57) ABSTRACT

Systems and methods for heating a non-combustion chemical reactor with thermal energy from a geothermal heat source are described. A working fluid is directed from the geothermal heat source to the chemical reactor to transfer heat. The working fluid can be circulated in a closed system so that it does not contact material at the geothermal heat source, or in an open system that allows the working fluid to intermix with material at the geothermal heat source. When intermixing with material at the geothermal heat source, the working fluid can transport donor substances at the geothermal heat source to the chemical reactor.

13 Claims, 26 Drawing Sheets

(51) Int. Cl.

| | | |
|---|---|---|
| *C01B 31/36* | (2006.01) | |
| *F24J 2/12* | (2006.01) | |
| *F24J 2/07* | (2006.01) | |
| *F28D 15/02* | (2006.01) | |
| *F24J 3/08* | (2006.01) | |
| *B01J 19/00* | (2006.01) | |
| *C12M 1/107* | (2006.01) | |
| *C12M 1/02* | (2006.01) | |
| *F23G 5/02* | (2006.01) | |
| *H01L 21/30* | (2006.01) | |
| *F01K 13/00* | (2006.01) | |
| *F24J 2/52* | (2006.01) | |
| *F28D 15/04* | (2006.01) | |
| *F28D 15/06* | (2006.01) | |

(52) U.S. Cl.
CPC ............... *C01B 31/36* (2013.01); *C12M 21/04* (2013.01); *C12M 41/20* (2013.01); *F01K 13/00* (2013.01); *F23G 5/02* (2013.01); *F24J 2/07* (2013.01); *F24J 2/12* (2013.01); *F24J 2/5266* (2013.01); *F28D 15/02* (2013.01); *F28D 15/046* (2013.01); *F28D 15/06* (2013.01); *H01L 21/30* (2013.01); *F23G 2201/50* (2013.01); *F23G 2900/50803* (2013.01); *F24J 3/083* (2013.01); *F24J 3/084* (2013.01); *F24J 3/085* (2013.01); *Y02E 10/125* (2013.01); *Y02E 10/14* (2013.01); *Y02E 10/41* (2013.01); *Y02E 10/42* (2013.01); *Y02E 10/47* (2013.01)

(56) References Cited

U.S. PATENT DOCUMENTS

| | | | |
|---|---|---|---|
| 3,662,832 A | | 5/1972 | Keeler et al. |
| 3,757,860 A | | 9/1973 | Pritchett |
| 3,788,389 A | | 1/1974 | Waters |
| 3,807,491 A | | 4/1974 | Van Hulsen |
| 3,830,508 A | | 8/1974 | Endicott |
| 3,840,068 A | | 10/1974 | Waters |
| 3,882,937 A | | 5/1975 | Robinson |
| 3,936,652 A | | 2/1976 | Levine |
| 3,975,912 A | | 8/1976 | Greene |
| 3,986,362 A | | 10/1976 | Baciu |
| 3,990,502 A | | 11/1976 | Best |
| 3,991,817 A | | 11/1976 | Clay |
| 4,019,868 A | | 4/1977 | Sebacher et al. |
| 4,053,576 A | | 10/1977 | Fletcher |
| 4,070,861 A | | 1/1978 | Scragg et al. |
| 4,082,865 A | | 4/1978 | Ban et al. |
| 4,099,489 A | | 7/1978 | Bradley |
| 4,138,993 A | | 2/1979 | Conley |
| 4,158,354 A | | 6/1979 | Carden |
| 4,161,211 A | | 7/1979 | Duffy et al. |
| 4,169,460 A | | 10/1979 | Popovich et al. |
| 4,172,506 A | | 10/1979 | Terry |
| 4,178,987 A | | 12/1979 | Bowman et al. |
| 4,229,184 A | | 10/1980 | Gregg |
| 4,257,239 A | | 3/1981 | Partin et al. |
| 4,343,338 A | | 8/1982 | Hart |
| 4,382,189 A | | 5/1983 | Wilson |
| 4,386,801 A | | 6/1983 | Chapman et al. |
| 4,401,689 A | | 8/1983 | Ban |
| 4,455,045 A | | 6/1984 | Wheeler |
| 4,519,342 A | | 5/1985 | Yoon |
| 4,549,078 A | | 10/1985 | Monahan |
| 4,549,528 A | | 10/1985 | Gibson |
| 4,601,508 A | | 7/1986 | Kerian |
| 4,611,847 A | | 9/1986 | Sullivan |
| 4,620,580 A | | 11/1986 | Groezinger et al. |
| 4,704,267 A | | 11/1987 | DiMartino |
| 4,706,651 A | | 11/1987 | Yudow |
| 4,746,160 A | | 5/1988 | Wiesemeyer |
| 4,848,445 A | | 7/1989 | Harper |
| 4,856,281 A | * | 8/1989 | Taylor .................. 60/641.9 |
| 4,921,580 A | | 5/1990 | Martes et al. |
| 4,978,162 A | | 12/1990 | Labbe |
| 5,058,945 A | | 10/1991 | Elliott, Sr. et al. |
| 5,119,897 A | | 6/1992 | Moriwake |
| 5,132,090 A | | 7/1992 | Volland |
| 5,222,698 A | | 6/1993 | Nelson et al. |
| 5,280,990 A | | 1/1994 | Rinard |
| 5,315,868 A | | 5/1994 | Jacobi et al. |
| 5,348,774 A | | 9/1994 | Golecki et al. |
| 5,407,245 A | | 4/1995 | Geropp |
| 5,442,934 A | | 8/1995 | Wolflick |
| 5,498,059 A | | 3/1996 | Switlik |
| 5,558,721 A | | 9/1996 | Kohmura et al. |
| 5,560,443 A | | 10/1996 | DuBose |
| 5,618,134 A | | 4/1997 | Balch |
| 5,647,877 A | | 7/1997 | Epstein |
| 5,685,362 A | * | 11/1997 | Brown .................. 165/45 |
| 5,881,559 A | | 3/1999 | Kawamura |
| 5,882,382 A | | 3/1999 | Hachisuka et al. |
| 5,986,429 A | | 11/1999 | Mula, Jr. |
| 6,012,065 A | | 1/2000 | Boucher et al. |
| 6,068,328 A | | 5/2000 | Gazdzinski |
| 6,074,696 A | | 6/2000 | Sato |
| 6,081,183 A | | 6/2000 | Mading et al. |
| 6,089,224 A | | 7/2000 | Poulek |
| 6,092,861 A | | 7/2000 | Whelan |
| 6,155,212 A | | 12/2000 | McAlister |
| 6,200,069 B1 | | 3/2001 | Miller |
| 6,216,599 B1 | | 4/2001 | Cavanagh |
| 6,220,193 B1 | | 4/2001 | Dilks |
| 6,242,752 B1 | | 6/2001 | Soma et al. |
| 6,309,010 B1 | | 10/2001 | Whitten |
| 6,334,928 B1 | | 1/2002 | Sekine et al. |
| 6,378,932 B1 | | 4/2002 | Fasel et al. |
| 6,409,252 B1 | | 6/2002 | Andrus |
| 6,464,755 B2 | | 10/2002 | Nakanishi et al. |
| 6,502,533 B1 | | 1/2003 | Meacham |
| 6,508,209 B1 | | 1/2003 | Collier, Jr. |
| 6,531,704 B2 | | 3/2003 | Yadav et al. |
| 6,534,210 B2 | | 3/2003 | Luken et al. |
| 6,571,747 B1 | | 6/2003 | Gerstweiler |
| 6,585,785 B1 | | 7/2003 | Warren et al. |
| 6,630,267 B2 | | 10/2003 | Badding et al. |
| 6,749,043 B2 | | 6/2004 | Brown et al. |
| 6,756,140 B1 | | 6/2004 | McAlister |
| 6,756,565 B2 | | 6/2004 | Suenaga et al. |
| 6,838,782 B2 | | 1/2005 | Vu |
| 6,854,788 B1 | | 2/2005 | Graham |
| 6,881,508 B2 | | 4/2005 | Penev |
| 6,886,249 B2 | | 5/2005 | Smalc |
| 6,889,755 B2 | | 5/2005 | Zuo et al. |
| 6,897,575 B1 | | 5/2005 | Yu |
| 6,908,297 B2 | | 6/2005 | Dafft et al. |
| 6,919,062 B1 | | 7/2005 | Vasileiadis et al. |
| 6,923,004 B2 | | 8/2005 | Chandran et al. |
| 6,926,345 B2 | | 8/2005 | Ortega et al. |
| 6,979,049 B2 | | 12/2005 | Ortega et al. |
| 6,984,305 B2 | | 1/2006 | McAlister |
| 7,014,737 B2 | | 3/2006 | Harutyunyan et al. |
| 7,033,570 B2 | | 4/2006 | Weimer et al. |
| 7,051,794 B2 | | 5/2006 | Luo |
| 7,140,181 B1 | | 11/2006 | Jensen et al. |
| 7,152,908 B2 | | 12/2006 | Shahbazi |
| 7,165,804 B2 | | 1/2007 | Shahbazi |
| 7,179,383 B1 | | 2/2007 | Porter et al. |
| 7,185,944 B2 | | 3/2007 | Shahbazi |
| 7,207,620 B2 | | 4/2007 | Cosgrove et al. |
| 7,210,467 B2 | | 5/2007 | Kweon et a |
| 7,211,905 B1 | | 5/2007 | McDavid, Jr. |
| 7,237,827 B2 | | 7/2007 | Shahbazi |
| 7,243,980 B2 | | 7/2007 | Vala |
| 7,250,151 B2 | | 7/2007 | Tonkovich et al. |
| 7,285,350 B2 | | 10/2007 | Keefer et al. |
| 7,293,533 B2 | | 11/2007 | Hemsath |
| 7,337,612 B2 | | 3/2008 | Skinnes et al. |
| 7,343,971 B2 | | 3/2008 | Pfefferle |
| 7,397,141 B2 | | 7/2008 | Gouker |
| 7,420,004 B2 | | 9/2008 | Hardy et al. |

(56) References Cited

U.S. PATENT DOCUMENTS

| | | |
|---|---|---|
| 7,426,959 B2 | 9/2008 | Wang et al. |
| 7,449,158 B2 | 11/2008 | Haueter et al. |
| 7,484,553 B2 | 2/2009 | Lai et al. |
| 7,504,739 B2 | 3/2009 | Enis et al. |
| 7,527,094 B2 | 5/2009 | McKinzie et al. |
| 7,568,479 B2 | 8/2009 | Rabinowitz |
| 7,582,167 B2 | 9/2009 | Kaszuba et al. |
| 7,585,339 B2 | 9/2009 | Dahl et al. |
| 7,587,998 B2 | 9/2009 | Hotta et al. |
| 7,597,068 B2 | 10/2009 | Arai et al. |
| 7,608,120 B2 | 10/2009 | Wunning |
| 7,621,262 B2 | 11/2009 | Zubeck |
| 7,628,137 B1 | 12/2009 | McAlister |
| 7,692,170 B2 | 4/2010 | Gaus et al. |
| 7,713,642 B2 | 5/2010 | Warner et al. |
| 7,714,258 B2 | 5/2010 | Dalton |
| 7,745,026 B2 | 6/2010 | Fan et al. |
| 7,753,122 B2 | 7/2010 | Curlett |
| 7,775,261 B2 | 8/2010 | Valenzuela |
| 7,788,924 B2 | 9/2010 | Hines |
| 7,789,182 B2 | 9/2010 | Bradley et al. |
| 7,799,315 B2 | 9/2010 | Amendola |
| 7,808,121 B1 | 10/2010 | Glynn |
| 7,856,843 B2 | 12/2010 | Enis et al. |
| 7,884,308 B1 | 2/2011 | Mejia |
| 7,910,258 B2 | 3/2011 | Steinberg |
| 7,943,045 B2 | 5/2011 | Rohrich et al. |
| 7,943,808 B2 | 5/2011 | Hershkowitz et al. |
| 7,955,478 B2 | 6/2011 | McClure |
| 7,963,328 B2 | 6/2011 | Khinkis et al. |
| 7,971,861 B2 | 7/2011 | Soininen |
| 7,972,471 B2 | 7/2011 | Sant |
| 8,043,592 B2 | 10/2011 | Krass |
| 8,053,916 B2 | 11/2011 | Edwards et al. |
| 8,083,520 B2 | 12/2011 | Mueller et al. |
| 8,136,740 B2 | 3/2012 | Hagen et al. |
| 8,202,817 B2 | 6/2012 | Yuge et al. |
| 8,220,539 B2 | 7/2012 | Vinegar et al. |
| 8,449,634 B2 | 5/2013 | Tamura et al. |
| 2002/0102188 A1 | 8/2002 | Hsu et al. |
| 2003/0008183 A1 | 1/2003 | Hsu |
| 2003/0024686 A1* | 2/2003 | Ouellette ............... 165/47 |
| 2003/0178195 A1 | 9/2003 | Agee et al. |
| 2004/0200618 A1 | 10/2004 | Piekenbrock |
| 2004/0219737 A1 | 11/2004 | Quon |
| 2004/0247957 A1 | 12/2004 | Hatano et al. |
| 2004/0253168 A1 | 12/2004 | Chu |
| 2004/0265448 A1 | 12/2004 | Shiau et al. |
| 2004/0266615 A1 | 12/2004 | Watson et al. |
| 2005/0029120 A1 | 2/2005 | Bar-Gadda |
| 2005/0061486 A1 | 3/2005 | Yang |
| 2005/0079977 A1 | 4/2005 | Choi et al. |
| 2005/0265919 A1 | 12/2005 | Lomax et al. |
| 2005/0272856 A1 | 12/2005 | Cooper et al. |
| 2006/0005738 A1 | 1/2006 | Kumar |
| 2006/0005739 A1 | 1/2006 | Kumar |
| 2006/0048808 A1 | 3/2006 | Ruckman et al. |
| 2006/0266043 A1 | 11/2006 | Jerome |
| 2007/0031718 A1 | 2/2007 | Fujimura et al. |
| 2007/0095065 A1* | 5/2007 | Kaplan et al. ............ 60/651 |
| 2007/0137202 A1* | 6/2007 | Hines ...................... 60/641.2 |
| 2007/0138006 A1 | 6/2007 | Oakes et al. |
| 2007/0205298 A1 | 9/2007 | Harrison et al. |
| 2007/0220810 A1 | 9/2007 | Leveson et al. |
| 2007/0295477 A1 | 12/2007 | Mueller et al. |
| 2008/0000469 A1* | 1/2008 | Weir ........................ 126/643 |
| 2008/0073066 A1 | 3/2008 | Chang et al. |
| 2008/0086946 A1 | 4/2008 | Weimer et al. |
| 2008/0098654 A1 | 5/2008 | Cherry et al. |
| 2008/0170975 A1 | 7/2008 | Ahn et al. |
| 2008/0175766 A1 | 7/2008 | Mankins et al. |
| 2008/0241033 A1 | 10/2008 | Nazri |
| 2008/0295883 A1 | 12/2008 | Ducellier et al. |
| 2009/0062591 A1 | 3/2009 | Bingue et al. |
| 2009/0206666 A1 | 8/2009 | Sella et al. |
| 2009/0313886 A1 | 12/2009 | Hinman et al. |
| 2010/0000874 A1 | 1/2010 | Hinman et al. |
| 2010/0043404 A1 | 2/2010 | Hebbale et al. |
| 2010/0107994 A1 | 5/2010 | Moriarty et al. |
| 2010/0140950 A1 | 6/2010 | Pitre |
| 2010/0174124 A1 | 7/2010 | Tonkovich et al. |
| 2010/0242352 A1 | 9/2010 | Perkins et al. |
| 2011/0061295 A1 | 3/2011 | McAlister |
| 2011/0061383 A1 | 3/2011 | McAlister |
| 2011/0100731 A1 | 5/2011 | Hassan |
| 2011/0197599 A1 | 8/2011 | Stewart et al. |
| 2011/0214986 A1 | 9/2011 | Brown |
| 2011/0220040 A1 | 9/2011 | McAlister |
| 2011/0284298 A1 | 11/2011 | Ajisaka |
| 2011/0315539 A1 | 12/2011 | Zadik et al. |
| 2012/0118878 A1 | 5/2012 | Kim et al. |
| 2012/0119510 A1 | 5/2012 | Herzen et al. |

FOREIGN PATENT DOCUMENTS

| | | |
|---|---|---|
| CN | 101042261 A | 9/2007 |
| CN | 101091900 A | 12/2007 |
| CN | 101597025 A | 12/2009 |
| EA | 200702287 A1 | 4/2008 |
| EP | 1658892 A1 | 5/2006 |
| FR | 2923731 A1 | 5/2009 |
| GB | 24256 | 7/1911 |
| JP | 59046375 | 3/1984 |
| JP | H02025571 | 1/1990 |
| JP | H04044314 | 2/1992 |
| JP | H11108465 A | 4/1999 |
| JP | 2000271472 A | 10/2000 |
| JP | 2001080902 A | 3/2001 |
| JP | 2001181846 A | 7/2001 |
| JP | 2001262353 A | 9/2001 |
| JP | 03215670 B2 | 10/2001 |
| JP | 2003040601 A | 2/2003 |
| JP | 2003166059 A | 6/2003 |
| JP | 2005511467 A | 6/2003 |
| JP | 2005021876 A | 1/2005 |
| JP | 2005213069 A | 8/2005 |
| JP | 2007139399 A | 6/2007 |
| JP | 2007527348 A | 9/2007 |
| JP | 2007254180 A | 10/2007 |
| JP | 2008503709 A | 2/2008 |
| JP | 2009500274 A | 1/2009 |
| JP | 2009513466 A | 4/2009 |
| JP | 2010003568 A | 1/2010 |
| JP | 2010006653 A | 1/2010 |
| JP | 2010025031 A | 2/2010 |
| JP | 2011507218 A | 3/2011 |
| KR | 100794943 B1 | 1/2008 |
| KR | 20120077307 A | 7/2012 |
| RU | 2011864 C1 | 4/1994 |
| RU | 2120913 C1 | 10/1998 |
| RU | 2312059 C1 | 12/2007 |
| RU | 2403379 C1 | 11/2010 |
| SU | 1498908 A1 | 8/1989 |
| SU | 1776298 | 11/1992 |
| WO | WO-2007053370 A2 | 5/2007 |
| WO | WO-2007140441 A2 | 12/2007 |
| WO | WO-2008031488 A1 | 3/2008 |
| WO | WO-2008035776 A1 | 3/2008 |
| WO | WO-2008076840 A2 | 6/2008 |
| WO | WO-2008093661 A1 | 8/2008 |
| WO | WO-2009098375 A1 | 8/2009 |
| WO | WO-2011154945 A2 | 12/2011 |

OTHER PUBLICATIONS

"Closed Loop Thermochemical Energy Storage System Using Ammonia." Australian National University College of Engineering & Computer Science—Solar Thermal Group. Accessed: Jan. 4, 2011. Printed: May 20, 2011. <http://solar-thermal.anu.edu.au/high-temperature/thermochemical-energy-storage/>. pp. 1-2.

"SI Cycle." Digital image. Sandia National Laboratories: Energy, Resources and Nonproliferation. Accessed: Jan. 4, 2011. Printed: Jun. 13, 2011. <http://www.sandia.gov/ERN/images/SI-cycle2.jpg>. p. 1.

(56) References Cited

OTHER PUBLICATIONS

"Solar Hydrogen." Digital image. Swiss Federal Institute of Technology, Department of Mechanical and Process Engineering, Zurich. Accessed: Jan. 4, 2011. Printed: May 23, 2011. p. 1. <http://www.pre.ethz.ch/research/projects/imgs/solarhydro_1.jpg>.

"The Carbon Cycle : Feature Articles." NASA Earth Observatory : Home. Web. Accessed: Jul. 1, 2010. Printed: Jun. 13, 2011. 12 Pages. <http://earthobservatory.nasa.gov/Features/CarbonCycle>.

"The Solar Zinc Route." Digital image. Swiss Federal Institute of Technology, Department of Mechanical and Process Engineering, Zurich. Accessed: Jan. 4, 2011. Printed: May 20, 2011. <http://www.pre.ethz.ch/research/projects/imgs/solzinc_1.jpg>. p. 1.

"Zinc Zinc—oxide Thermochemical Cycle." Digital image. Wikipedia, the Free Encyclopedia, Published: Dec. 21, 2008. Accessed: Jan. 4, 2011. Printed: May 20, 2011. <http://en.wikipedia.org/wiki/File:Zinc_zinc-oxide_thermochemical_cycle.jpg>. p. 1.

Chen et al. "Parylene-Encapsulated Copolymeric Membranes as Localized and Sustained Drug Delivery Platforms." Annals of Biomedical Engineering, vol. 37, Issue 10 (Oct. 2009): pp. 2003-2017.

Chen et al. "Thermochemistry Concept Map." Teacherknowledge Wikispace, Published: Nov. 20, 2006. <http://teacherknowledge.wikispaces.com/file/view/Thermochemistry+concept+map+-+Extended.pdf>. p. 1.

Food and Agriculture Organization of the United Nations. "Carbon Sequestration Options under the Clean Development Mechanism to Address Land Degradation." World Soil Resources Reports. Rome, 2000. pp. 1-45.

Foust et al. "An Economic and Environmental Comparison of a Biochemical and a Thermochemical Lignocellulosic Ethanol Conversion Processes." Cellulose, vol. 16, Issue 4. Jun. 10, 2009. pp. 547-565.

Funk, James E. "Thermochemical Processes for the Production of Hydrogen from Water." College of Engineering, University of Kentucky, Lexington, Kentucky. 1975. pp. 1-9.

Hackett et al. "Evaluation of Conversion Technology Processes and Products: Appendix A—Discussion of Thermochemical Process Definitions." University of California, Davis. Sep. 2004. pp. 1-7.

Kasting, James F. "The Carbon Cycle, Climate, and the Long-Term Effects of Fossil Fuel Burning." U.S. Global Change Research Information Office. 1998. Web. Accessed: Jul. 1, 2010. Printed: Jun. 13, 2011. <http://www.gcrio.org/CONSEQUENCES/vol4no1/carbcycle.html>.

U.S. Energy Information Administration. "Greenhouse Gases—Energy Explained, Your Guide to Understanding Energy." Web. Accessed: Jul. 1, 2010. Printed: Jun. 13, 2011. 1 Pages. <http://www.eia.gov/energyexplained/index.cfm?page=environment_about_ghg>.

US Environmental Protection Agency. "Cap and Trade." Web. Accessed: Jul. 1, 2010. Printed: Jun. 13, 2011. <http://www.epa.gov/captrade/>.

US Environmental Protection Agency. "Carbon Dioxide—Geologic Sequestration | Climate Change—Greenhouse Gas Emissions | U.S. EPA." Web. Accessed: Jul. 1, 2010. Printed: Jun. 13, 2011. <http://www.epa.gov/climatechange/emissions/co2_geosequest.html>.

US Environmental Protection Agency. "Carbon Dioxide | Climate Change—Greenhouse Gas Emissions|U.S. EPA". Web. Accessed: Jul. 1, 2010. Printed: Jun. 13, 2011. 1 Page. <http://www.epa.gov/climatechange/emissions/co2.html>.

US Environmental Protection Agency. "EPA Preliminary Analysis of the Waxman-Markey Discussion Draft". Web. Accessed: Jul. 1, 2010. Printed: Jun. 13, 2011. <http://www.epa.gov/climatechange/economics/pdfs/WM-Analysis.pdf>.

International Search Report and Written Opinion for PCT Application No. PCT/US2012/050647; Date of Mailing: Feb. 13, 2013, 12 pages.

Solar Collectors, Energy Storage, and Materials, pp. 443-444 (DeWinter, Francis, 1991).

Vegners, Raimonds Maris; "Colloidal Carbon and Silica : Their Use in Solar Energy" Table of Contents and Introduction of Thesis, University of Sydney, Feb. 1985, 5 pages.

N. Muradov: "Catalysis of Methane decomposition over elemental carbon", Catalysis Communications, No. 3-4, Jul. 1, 2001, pp. 89-94, p. 89, right-hand column, paragraph 2.

Wikipedia > Aerogel > Carbon—"Carbon aerogels are also extremely 'black' in the infrared spectrum, reflecting only 0.3% of radiation between 250 nm and 14.3 μm, making them efficient for solar energy collectors," 1 page. Accessed in 2011.

International Search Report and Written Opinion for PCT Application No. PCT/US2014/015878; Date of Mailing; May 20, 2014; 10 pages.

Muradov et al: "Catalytic Dissociation of Hydrocarbons: a Route to CO2-free Hydrogen", 15th Annual Symposium on Catalysis in Petroleum Refining & Petrochemicals.

\* cited by examiner

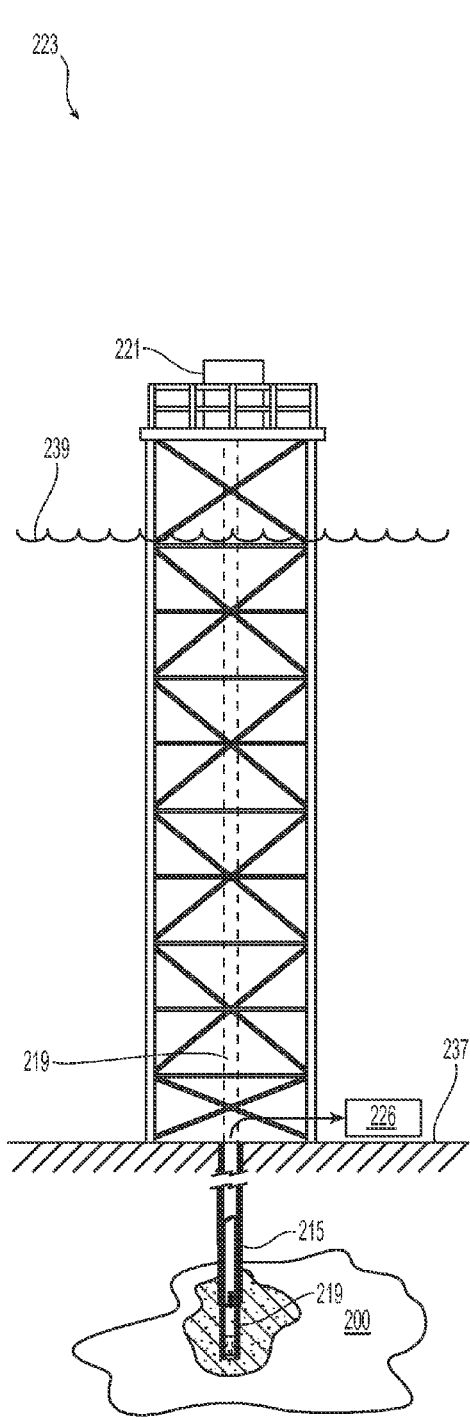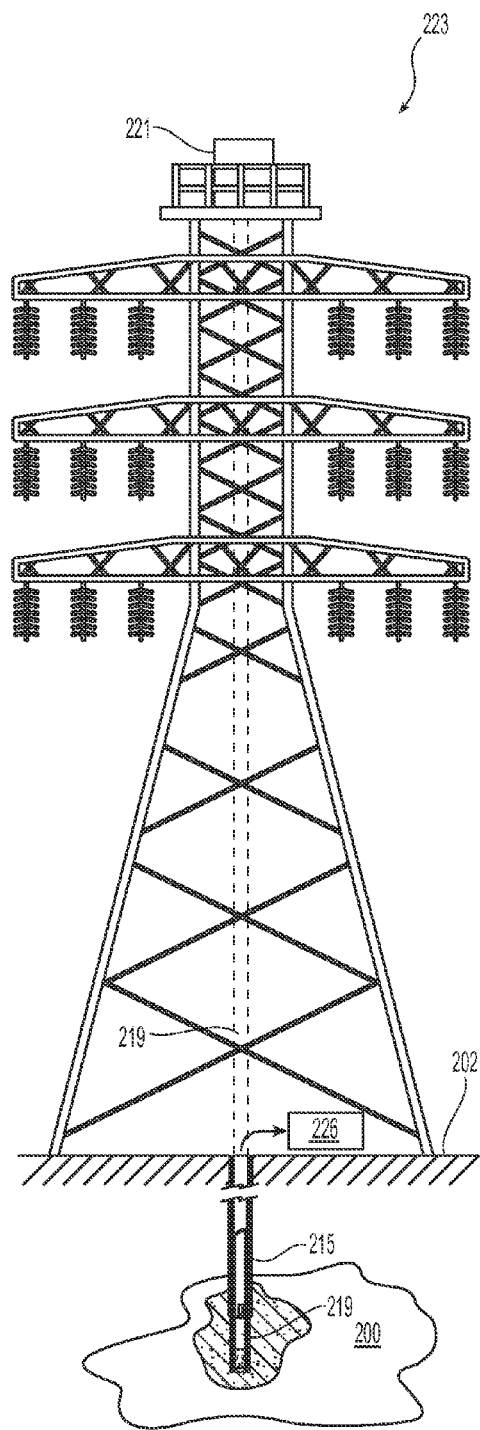
*Fig. 2E*  *Fig. 2F*

GEOTHERMAL ENERGIZATION OF A NON-COMBUSTION CHEMICAL REACTOR AND ASSOCIATED SYSTEMS AND METHODS

CROSS REFERENCE TO RELATED APPLICATIONS

The present application is a divisional of U.S. application Ser. No. 13/764,107, filed on Feb. 11, 2013, which is a continuation-in-part of pending U.S. application Ser. No. 13/584,688, filed on Aug. 13, 2012, which claims priority to U.S. Provisional Application No. 61/523,266, filed on Aug. 12, 2011 and incorporated herein by reference. To the extent the foregoing provisional application and/or any other materials incorporated herein by reference conflict with the present disclosure, the present disclosure controls.

TECHNICAL FIELD

The present application is directed generally to systems and methods for transferring heat from geothermal sources to chemical reactors. In particular embodiments, the heat provided by the geothermal sources facilitates the operation of a non-combustion chemical reactor.

BACKGROUND

Chemical processes that require a substantial amount of heat are often expensive to operate when the heating is provided by non-renewable energy sources. Self-sustaining and renewable sources of thermal energy can provide sufficient thermal energy to operate or facilitate the operation of thermal reactors, but conveying sufficient thermal energy from geothermal sources to the reactors can be difficult. In light of the foregoing, there remains a need to efficiently transfer geothermal energy to heat chemical processing reactors in a sustainable manner.

BRIEF DESCRIPTION OF THE DRAWINGS

FIG. 2E is a partially schematic illustration of a closed system extending between an underground geothermal source and an elevated location on a representative offshore oil product platform in accordance with an embodiment of the presently disclosed technology.

FIG. 2F is a partially schematic illustration of a closed system extending between an underground geothermal source and an elevated location on a representative electrical tower in accordance with an embodiment of the presently disclosed technology.

DETAILED DESCRIPTION

Figure 1:
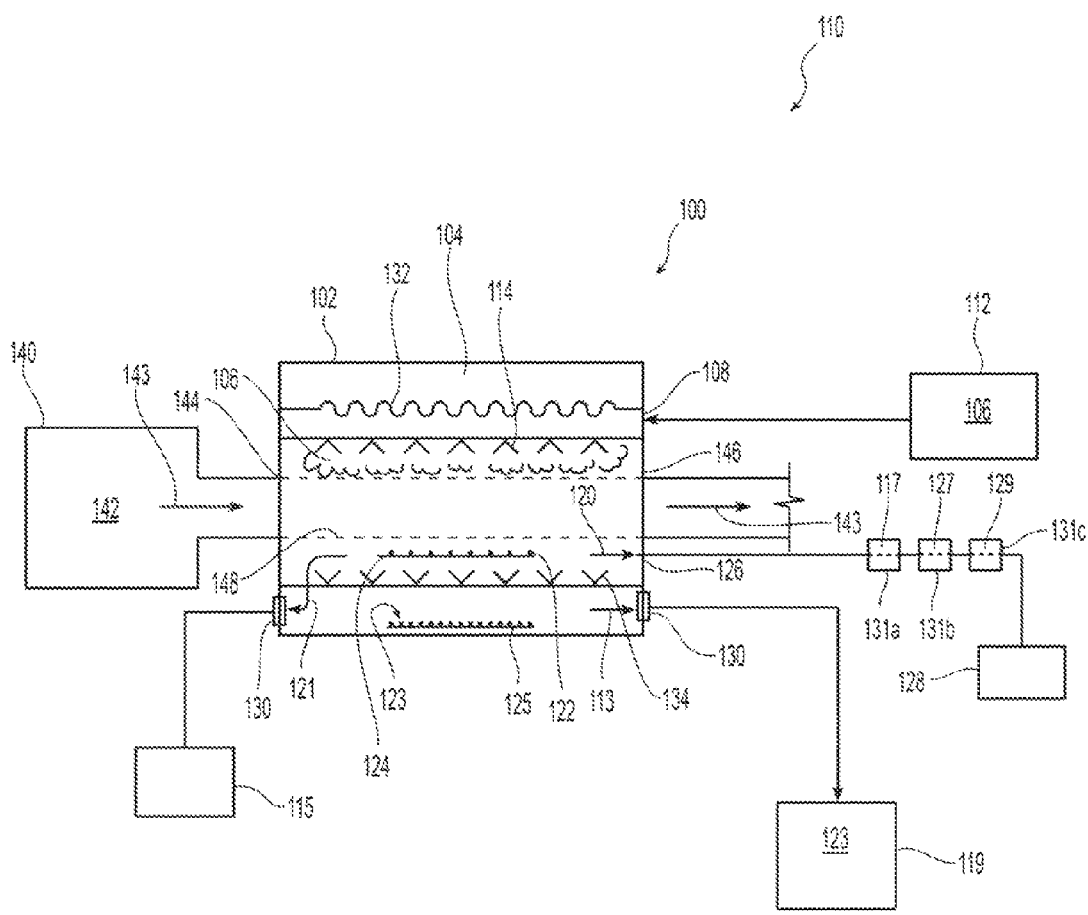
FIG. 1 is a partially schematic, partially cross-sectional illustration of a chemical processing system having a thermochemical processing (TCP) reactor configured in accordance with an embodiment of the presently disclosed technology.

The present disclosure is directed generally to systems and methods for using geothermal energy to heat a chemical reaction, e.g., a non-combustion chemical reaction, in a thermochemical processing (TCP) reactor system. TCP reactors can process the fluids collected from various sources to provide hydrogen and/or other products. Accordingly, these systems can in particular embodiments use a renewable energy source (geothermal heat) to process carbon-based or other hydrogen donors (that are normally combusted), into clean-burning hydrogen and carbon-based structural building blocks.

1. Overview

Several examples of devices, systems and methods using geothermal energy to provide heat to a TCP reactor and/or to facilitate reactions in a TCP reactor are described below. The heating systems and TCP reactors can be used in accordance with multiple operational modes, depending on the particular embodiment, to transfer thermal energy and separate incoming reactants. In particular embodiments, the process of separating can include reforming, re-speciating, and/or dissociating a donor substance (e.g., methane) into a hydrogen component and a non-hydrogen donor component (e.g., carbon). The operational modes can include further processes of reformation, re-speciation, and/or combination of the products resulting from the TCP reactor processes and/or additional constituents. In particular embodiments, the system can also produce compounds of nitrogen (e.g., ammonia) for use as a working fluid. Although the following description provides many specific details of representative examples in a manner sufficient to enable a person skilled in the relevant art to practice, make and use them, several of the details and advantages described below may not be necessary to practice certain examples of the technology. Additionally, the technology can include other examples that are within the scope of the present technology but are not described here in detail.

References throughout this specification to "one example," "an example," "one embodiment" or "an embodiment" mean that a particular feature, structure, process or characteristic described in connection with the example is included in at least one example of the present technology. Thus, the occurrences of the phrases "in one example," "in an example," "one embodiment" or "an embodiment" in various places throughout this specification are not necessarily all referring to the same example. Furthermore, the particular features, structures, routines, steps or characteristics may be combined in any of a number of suitable manners in one or more examples of the technology. The headings provided herein are for convenience only and are not intended to limit or interpret the scope or meaning of the present technology.

Certain embodiments of the technology described below may take the form of computer-executable instructions, including routines executed by a programmable computer or controller. Those skilled in the relevant art will appreciate that the technology can be practiced on computer or controller systems other than those shown and described below. The technology can be embodied in a special-purpose computer, controller, or data processor that is specifically programmed, configured or constructed to perform one or more of the computer-executable instructions described below. Accordingly, the terms "computer" and "controller" as generally used herein refer to any data processor and can include Internet appliances, hand-held devices, multi-processor systems, programmable consumer electronics, network computers, mini-computers, and the like. The technology can also be practiced in distributed environments where tasks or modules are performed by remote processing devices that are linked through a communications network. Aspects of the technology described below may be stored or distributed on computer-readable media, including magnetic or optically readable or removable computer discs as well as media distributed electronically over networks. In particular embodiments, data structures and transmissions of data particular to aspects of the technology are also encompassed within the scope of the present technology. The present technology encompasses methods of both programming computer-readable media to perform particular steps, and executing the steps.

2. Representative TCP Reactors and TCP Reactor Systems

FIG. 1 is a partially schematic illustration of a representative TCP reactor 100 and reactor system 110. Further representative TCP reactors and reactor systems are described in detail in U.S. patent application Ser. No. 13/027,208, titled "CHEMICAL PROCESSES AND REACTORS FOR EFFICIENTLY PRODUCING HYDROGEN FUELS AND STRUCTURAL MATERIALS, AND ASSOCIATED SYSTEMS AND METHODS," filed Feb. 14, 2011, incorporated herein by reference and referred to as the '208 Application. As illustrated, the representative reactor 100 has a reactor vessel 102 configured and insulated to provide control of reaction conditions, including an elevated temperature and/or pressure within the interior of a reactor chamber 104, sufficient to reform or dissociate a donor substance 106 introduced into the reactor 100. The reforming or dissociation processes are non-combustive processes and can be conducted in accordance with the parameters described in the '208 Application previously incorporated herein by reference. The reactor system 110 can include heat exchangers, heaters, piping, valves, sensors, ionizers, and other equipment (not shown in FIG. 1) to facilitate introducing the donor substance 106 into the TCP reactor 100, to facilitate reforming, respeciating and/or dissociating the donor substance 106 within the reactor 100, and to facilitate extracting dissociated and/or reformed components of the donor substance 106 from the reactor 100.

The reactor chamber 104 includes one or more donor inlets 108 for receiving the donor substance 106 from a donor source 112. In particular embodiments, the donor substance 106 is a hydrogen donor and can be a solid, liquid, and in further embodiments a gaseous hydrocarbon, e.g., methane gas. The donor substance 106 can include other carbon-based compounds, e.g., ethane, propane or butane, along with cetane and/or octane rated compounds. In still further embodiments, the donor substance 106 can include a lower grade constituent, e.g., off-grade cetane or octane rated hydrocarbons, or wet alcohol. In at least some embodiments, the donor substance can include compounds other than hydrocarbon fuels (e.g., carbohydrates, fats, alcohols, esters, cellulose and/or others). In yet further embodiments, the hydrogen donor 106 can include hydrogen atoms in combination with constituents other than carbon. For example, nitrogenous compounds (e.g., ammonia and/or urea) can serve a similar hydrogen donor function. Examples of other suitable hydrogen donors are described in the '208 Application, previously incorporated herein by reference. In yet further embodiments, the donor substance can donate constituents other than hydrogen. For example, the reactor 100 can dissociate oxygen from $CO_2$ and/or another oxygen donor, or the reactor 100 can dissociate a halogen donor. The donor substance 106 can be in a gaseous or liquid form that is distributed into the reactor chamber 104 through donor inlet nozzles 114. Typically, the donor substance 106 is provided as a vapor or gas. In other embodiments, the donor substance 106 can be a liquid or vapor that undergoes a gas phase transition in the reactor chamber 104.

In the reactor chamber 104, the donor substance 106 undergoes reformation, partial oxidation and/or a non-combustion-based dissociation reaction and dissociates into at least two components, e.g., a gas 120 and a solid 122. In other embodiments, the dissociated components can take the form of a liquid and a gas, or two gases, depending on the donor substance used and the dissociation process parameters. In further embodiments, the donor substance 106 can dissociate into three or more dissociated components in the form of a solid, gas, or liquid, or a mixture of these phases. In a particular embodiment, methane is the donor substance, and the dissociated components are carbon and hydrogen.

When carbon is a dissociated component, it can be disposed as a solid 122 on an internal donor solid (e.g., carbon) collector 124 within the reactor chamber 104, and when hydrogen is a dissociated component, it can be in the form of a gas 120 within the reaction chamber 104. The carbon can be transferred from the internal collector 124 to an industrial manufacturing or packaging plant via a storage tank or other receptacle 115 as shown by arrow 121. The hydrogen gas can react with carbon dioxide from sources such as a combustion chamber 140 and/or the donor source 112 for production of fluids such as selected alcohols and/or water. In other embodiments, the hydrogen and carbon can be removed from the reaction chamber 104 together (e.g., in gaseous forms such as $H_2$ and CO and/or $CO_2$ and/or $CH_3OH$ and/or $C_2H_5OH$, among others) and separated outside the reaction chamber 104. Substances such as hydrogen 117, carbon monoxide 127, and water 129 can be collected by selective filtration, pressure or temperature swing adsorption and/or phase separation processes in separation/collection subsystems (e.g., collectors) 131a, 131b and 131c. Any remaining constituents can be collected at an additional collector 128. Products at elevated temperature can exchange heat with the donor substance (e.g., feed stocks) 106 to cool the outgoing products and heat the incoming reactants. As described above, in many of these embodiments, the donor substance functions as a hydrogen donor, and is dissociated into molecules of hydrogen (or a hydrogen compound) and molecules of the donor (or a donor compound).

In addition to removing the reaction products to access the products for other purposes, the reaction products can be removed in a manner and/or at a rate that facilitates the reaction taking place in the reactor chamber 104. For example, solid products (e.g., carbon) can be removed via a conveyor, and fluids (gases and/or liquids) can be removed via a selective filter or membrane to avoid also removing reactants. As the products are removed, they can exchange heat with the incoming reactants, as discussed above. In addition to pre-heating the reactants, this process can contract and/or change the phase of the products, which can further expedite the removal process and/or control (e.g., reduce) the pressure in the reactor chamber 104. In a particular embodiment, condensing water and/or alcohols from the product stream can achieve this purpose. In any of these embodiments, removing the reactants quickly rather than slowly can increase the rate and/or efficiency of the reaction conducted in the chamber 104.

In at least some embodiments, substances such as energy crops, forest slash, landfill waste and/or other organic wastes can be transferred into the reactor chamber 104, e.g., via the donor inlet 108, and can be anaerobically heated to produce gases such as methane, water vapor, hydrogen, and carbon monoxide. This process and/or other processes can create ash, which, if allowed to accumulate, can interfere with radiative heating and/or other processes within the reactor chamber 104. Accordingly, an ash residue 123 can be collected at an ash collector 125 and transferred to an external ash collector or receptacle 119 (as indicated by arrow 113) for various uses such as returning trace minerals to improve crop productivity from hydroponic operations or soil, or as a constituent in concrete formulas. The ash collector 125 can be cooled and/or positioned to selectively attract ash deposits as opposed to other products and/or reactants. In at least some embodiments, the ash may also contain char, which can also be collected. In general, the amount of ash and/or char introduced to and removed from the reactor 100 depends in part on the composition of the donor 106, with relatively simple and/or pure donors (e.g., pure methane) producing little or no ash and char. In any of these embodiments, an advantage associated with collecting the ash within the reactor chamber 104 rather than from the products exiting the chamber is that the ash is less likely to contaminate, foul and/or otherwise interfere with the efficient operation of the reactor 100. Benefits of the present embodiments include an increased tolerance regarding the rate with which the ash 123 is produced and/or removed from the reactor chamber 104. As a result, the ash may have little or no effect on the reaction rate in the chamber 104, and so may not be controlled as closely as the product removal rate.

The reaction chamber 104 includes one or more reaction chamber exit ports 126 (one is shown schematically in FIG. 1) through which gaseous or liquid dissociated components can be removed and delivered for subsequent processing or containment. The donor inlet nozzle 114, donor solid collector 124, and reaction chamber exit port 126 can be positioned to enhance (e.g., maximize) the movement of the donor substance 106 and dissociated components 120 and 122 through the reaction chamber 104, so as to facilitate accumulating and removing the dissociated components from the TCP reactor 100. The TCP reactor 100 can also include one or more solid collector exit ports 130 (two are shown in FIG. 1) through which the solid dissociated component 122 and/or ash 123 can be removed from the reactor 100. Representative carbon-based products from the reactor 100 include carbon, silicon carbide, halogenated hydrocarbons, graphite, and graphene. These products can be further processed, e.g., to form carbon films, ceramics, semiconductor devices, polymers and/or other structures. Accordingly, the products of the reaction conducted in the reactor 100 can be architectural constructs or structural building blocks that can be used as is or after further processing. Other suitable products are described in the '208 Application.

As described above, the TCP reactor 100 can be configured to facilitate the ingress of the donor substance 106 into the reactor chamber 104, and to permit the egress of materials, including the dissociated components 120 and 122 from the reactor chamber, e.g., as summarized in Equation 1 below. The TCP reactor 100 can also receive additional thermal energy provided by a heater 132 via concentrated solar energy or regenerative electric heating or by circulating heat transfer fluids. At times when solar, wind, hydroelectric, geothermal or another off-peak energy is available in excess of the demand for operating the system 110, energy (e.g., heat energy) can be stored in an insulated heat battery or transferred into a heated water storage medium. In particular embodiments, the TCP reactor 100, and the TCP reactor system 110 as a whole, can be configured to permit the ingress or egress of additional substances and/or energy into or out of the reaction chamber 104. These additional substances and/or energies can be applied to modify the operation of the TCP reactor 100 so as to accept different donor substances, to provide different dissociated and/or reformed components, to provide greater control over the dissociation reaction, and/or to provide greater efficiency in the operation of the TCP reactor system.

In the representative system of FIG. 1, a reactant distributor 134 for additional reactants e.g., water (steam), is disposed in the reactor chamber 104 to provide supplemental heat and/or constituents. Water in the reaction chamber 104 can also participate in reactions such as reforming steam and methane into the products shown in Equation 2 below. Accordingly, Equations 1 and 2 illustrate representative dissociation and reformation processes without water (or another oxygen donor) as a reactant and with water (or another oxygen donor, e.g., air) as a reactant:

$$CH_4 + HEAT_1 \rightarrow C + 2H_2 \quad (1)$$

$$CH_4 + H_2O + HEAT_2 \rightarrow CO + 3H_2 \quad (2)$$

In a particular embodiment shown in FIG. 1, the combustion chamber 140 directs combustion products 142 into the reaction chamber 100 through a combustion product inlet 144 as indicated by arrow 143. The heat-emitting combustion products 142 pass through the reactor 100 so as to provide additional heat to the reactor chamber 104 and exit via an outlet 146. The combustion products inlet 144 and outlet 146 can be joined by a pipe or conduit 148 that facilitates transferring heat from the combustion products 142 into the reaction chamber 104 and that, in particular embodiments, allows some or all of the combustion products 142 to enter the reaction chamber 104 through a permeable or transmissive surface of the conduit 148. Such products can include steam and/or oxides of carbon, nitrogen, and/or oxygen, and such surfaces are described further in U.S. application Ser. No. 13/026,996, titled "REACTOR VESSELS WITH TRANSMISSIVE SURFACES FOR PRODUCING HYDROGEN-BASED FUELS AND STRUCTURAL ELEMENTS, AND ASSOCIATED SYSTEMS AND METHODS," filed Feb. 14, 2011 and incorporated herein by reference. Accordingly, the combustion products 142 can supplement the donor substance 106 as a source of hydrogen and/or donor molecules. In further embodiments, the reactor 100 can also include one or more heat exchangers (e.g., counterflow heat exchangers) as described in the '208 Application. In any of these embodiments, sufficient heat is transmitted to the reactor 100 to enable the non-combustion dissociation reaction that separates the donor substance 106 into the donor-based component and hydrogen or hydrogen-based component.

Reactors having any of the foregoing configurations can be used to process substances obtained from a number of liquid, vapor, and/or gas producing sites. Representative sites include a landfill where organic action has produced recoverably valuable quantities of methane and/or carbon dioxide, the sea floor (holding frozen methane hydrates subject to mobilization such as via thawing), permafrost, deposits of degrading limestone that release carbon dioxide, anaerobically digested paper and/or paper products, and stranded well gas. Reactors processing the gases provided from such sites, and/or other sites, require heat to facilitate the non-combustion reaction, dissociation, and/or hydrolytic reactions. The necessary heat may be obtained in whole or in part from solar, wind, geothermal and/or other sources. Representative techniques for providing energy from a geothermal source to a TCP reactor are described below with reference to FIGS. 2-4.

3. Representative Geothermally-Heated TCP Reactor Systems

Reactors having any of the foregoing configurations can be used to process substances obtained from a number of liquid, vapor, and/or gas-producing sites. Representative sites include a landfill where organic action has produced recoverably valuable quantities of methane and/or carbon dioxide, the sea floor (holding frozen methane hydrates subject to mobilization such as via thawing), permafrost, deposits of degrading limestone that release carbon dioxide, anaerobically digested paper and/or paper products, and stranded well gas. Reactors processing the gases provided from such sites, and/or other sites, require heat to facilitate the non-combustion reaction, dissociation, and/or hydrolytic reactions. The necessary heat may be obtained in whole or in part from geothermal sources. Representative techniques for providing geothermal energy to a TCP reactor of a TCP reaction system are described below with reference to FIGS. 2A-4.

Figure 2A:
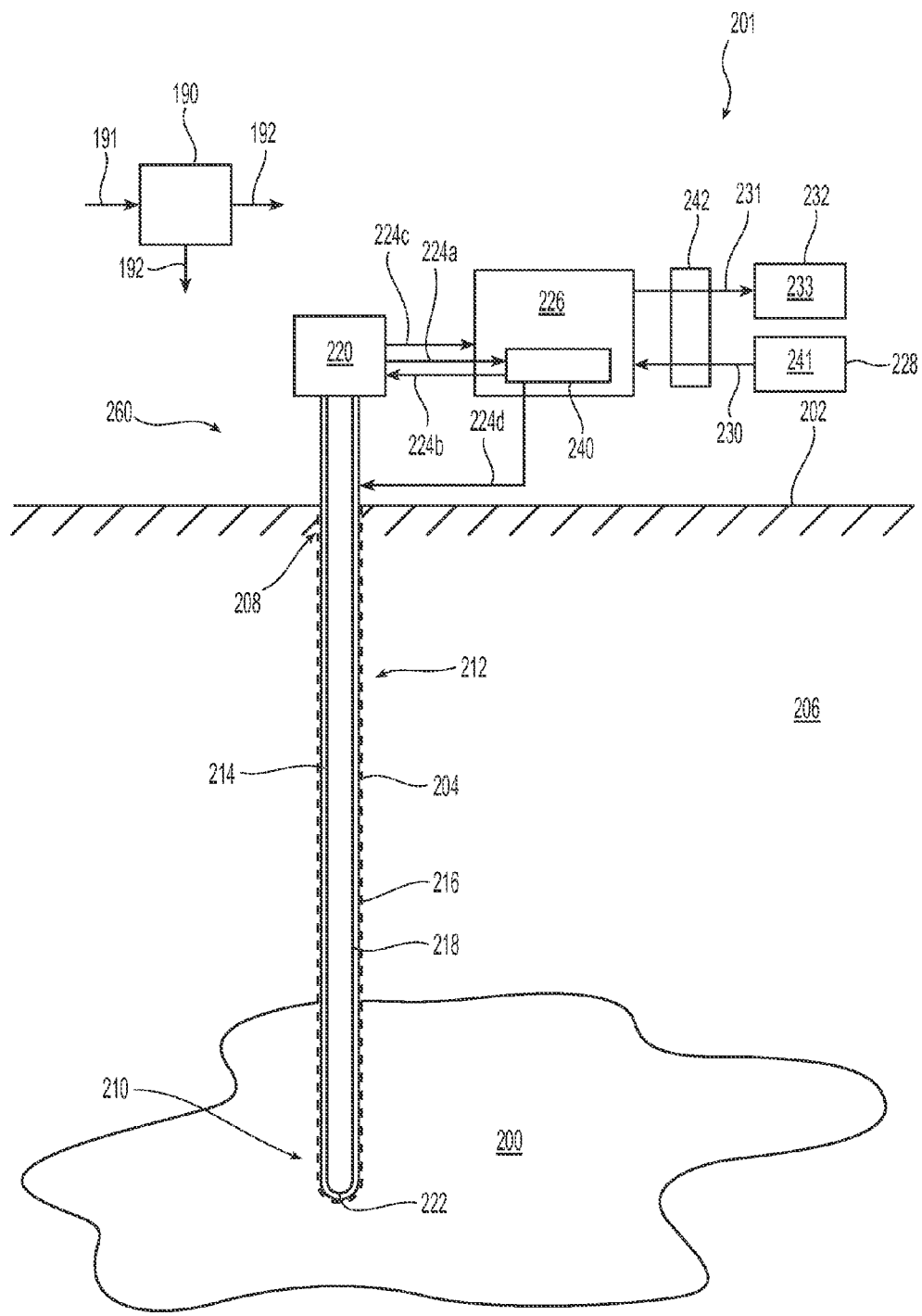
FIG. 2A is a partially schematic illustration of a thermochemical reactor heated by a closed system communicating with a geothermal source in accordance with an embodiment of the presently disclosed technology.

FIG. 2A is a partially schematic, cross-sectional elevation view of a TCP reactor 226 that sources and/or receives heat and/or reactants from a subterranean geothermal source 200. In this representative embodiment, the geothermal source is located below (e.g., approximately 1.5 miles below) the local surface 202. In this embodiment, the geothermal source 200 may include a zone such as an aquifer that is at a temperature of 150-700° F. due to thermal communication between the aquifer and a hot interior zone of the earth and/or a tectonic plate boundary (not shown). In other embodiments, the geothermal source 200 can include dry subterranean rock, a sufficiently hot subterranean surface, and/or a subterranean region located at or near an active volcanic region.

In a representative embodiment illustrated in FIG. 2A, a geothermally-heated TCP reactor system 201 is positioned near the geothermal source 200 and receives heat from the geothermal source 200 via a working fluid transfer system 260. A bore tube 204 in the ground 206 over the geothermal source 200 extends from a bore top 208 at or near the surface 202 to a bore zone 210 (e.g., a bottom of the bore tube 204) at or near the geothermal source 200. The bore tube 204 can be placed by known drilling techniques, and in some embodiments includes a pre-existing well (e.g., an oil well or water well). The working fluid transfer system 260 can include a heating pipe 212 having a downflow portion 214 and an upflow portion 216 (e.g., adjacent or annularly positioned relative to each other) that can be disposed in the bore tube 204 and that contain a working fluid 218. In a particular embodiment, the working fluid 218 includes water, and in other embodiments, the working fluid 218 includes other suitable heat transfer media (e.g., Therminol®, propane, butane, sulfur dioxide, ammonia, etc.), as discussed further below with reference to FIG. 4. In any of these embodiments, the working fluid 218 can travel downward as a relatively dense fluid and then return in a closed loop via a return portion 222 of the heating pipe 212 as a lower density fluid, e.g., a vapor or a gas. In certain embodiments, the working fluid 218 can circulate downward by gravitational force and upward as a vapor or gas that fills the available space. In other embodiments, the working fluid 218 circulates under the power of a pump 220 (e.g., a reversible pump). In certain embodiments, the pump 220 drives the working fluid 218 through the heating pipe 212 so as to deliver cooled working fluid 218 to the geothermal source 200 and return heated working fluid 218 to the surface 202.

In particular embodiments, the pump 220 can be a reversible pump and can accordingly operate in (at least) two modes: a first mode in which energy is supplied to the pump 220 to drive the working fluid 218, and a second mode in which the working fluid 218 drives the pump 220, which can in turn extract energy from the working fluid via a generator and/or other suitable device. The extracted energy can be provided to the reactor 226 and/or other system components, as indicated by arrow 224c. Accordingly, the working fluid can be selected to have chemical and/or physical properties that are suitable for dual-mode operation. Other overall system parameters can also be selected to enhance this function. For example, the heat transfer rate of the working fluid 218 (including the temperature and pressure it develops) and/or the position of the return portion 222 within the geothermal formation can be selected based at least in part on the dual-mode function of the working fluid. In particular embodiments for which the working fluid 218 operates in an open loop manner (described further below with reference to FIGS. 3 and 4), the substance extraction characteristics of the working fluid are also considered.

The pump 220 (and/or vapor pressure) directs the returned, heated working fluid 218 to the TCP reactor 226, as indicated by arrow 224a. The working fluid 218 transfers heat to the TCP reactor 226 via a first heat exchanger 240 and returns to the heating pipe 212 via the pump 220, as indicated by arrow 224b. In another embodiment, the working fluid 218 can bypass the pump 220, as indicated by arrow 224d. In particular embodiments, the heat exchanger 240 can include a surface that is permeable to the working fluid 218. This arrangement can be employed when the working fluid 218 is a suitable reactant, as well as a heat conveyor. For example, when the heat transfer fluid is water, it can participate in the reaction described above with reference to Equation (2) and FIG. 1. In further particular embodiments, the heat supplied to the TCP reactor 226 by the working fluid 218 can be supplemented by other heat sources, e.g., solar heat, electric heat, and/or heat from combustion products. In yet a further particular embodiment, a heat pump (described in further detail later) can be used to elevate the temperature of the working fluid. The TCP reactor 226 also receives a reactant substance 241 from a reactant source 228. In the representative embodiment shown in FIG. 2A, the reactant source 228 is a storage tank containing the reactant substance 241, and the reactant substance 241 includes a substance such as a hydrocarbon (e.g., crop or animal waste, garbage, landfill waste, methane, ethane, propane, butane or parafin). As illustrated, the reactant substance 241 is provided to the TCP reactor 226 via a pipe or other conduit 230 that is routed through a second heat exchanger 242 to preheat the reactant substance 241 before it enters the TCP reactor 226. Heat is provided to the reactant substance 241 by the products 233 produced at the reactor 226. Accordingly, the products 233 exit the TCP reactor 226 and pass through the second heat exchanger 242 via another pipe or conduit 231 (e.g., in a counterflow arrangement) to a products collector 232. In the representative embodiment of FIG. 2A, the reaction products are hydrogen and carbon, and the products collector for the hydrogen is a storage tank. The hydrogen and carbon (or other donor dissociated from the reactant substance 241 at the reactor 226) can be removed from the reactor 226 together and then separated, or they can be removed separately. In either embodiment, one or both products can transfer heat to the incoming reactant substance 241 via one or more heat exchangers 242. Additional sources of heat and reactant substances provided to the TCP reactor 226, and additional products of the TCP reactor 226, are described in the '208 Application.

The components of the overall system 201, including the reactor 226, can be controlled by a controller 190. Accordingly, the controller 190 can receive automatic or manual inputs 191 from sensors, transducers, detectors and operators. The controller 190 can be programmed with instructions that, when executed, issue commands or outputs 192 that direct the functions, settings, operating parameters, and/or states of the components of the system 201 to produce the desired outputs.

Figure 2B:
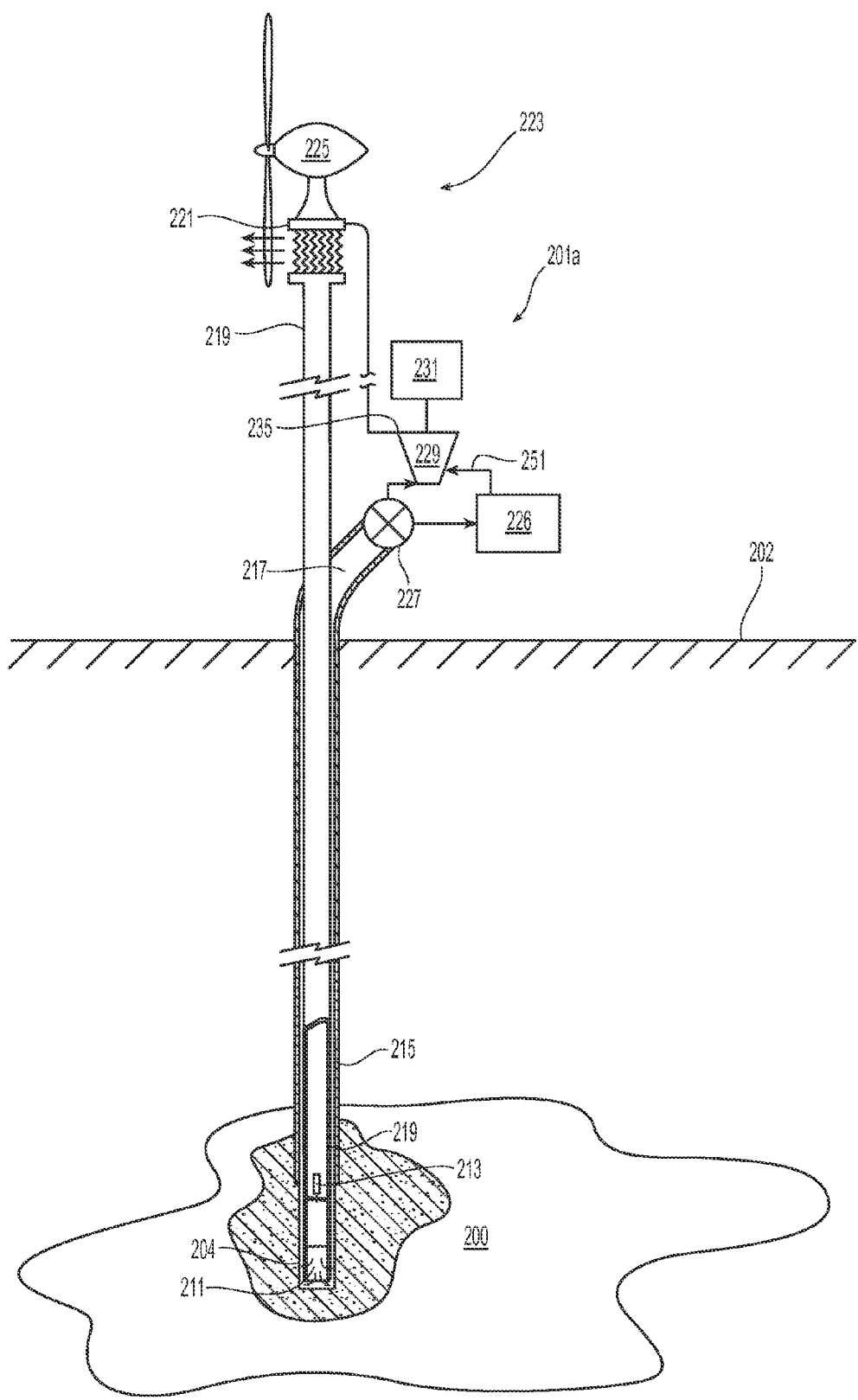
FIG. 2B is a partially schematic illustration of a thermochemical reactor coupled to an elevated closed system communicating with a geothermal source in accordance with an embodiment of the presently disclosed technology.

In at least some areas, significant advantages can be developed from natural or artificial height differences. FIG. 2B shows a portion 201a of a geothermally-heated TCP reactor system, configured to provide a dense water vapor or liquid 211 with a potential energy "head" above a motor-generator 213 disposed near the bottom of the bore tube 204 to produce power. As illustrated, the bore tube 204 extends from the surface 202 to the geothermal heat source 200. The bore tube 204 is provided with an insulated conduit 215 to maintain a desired temperature within passages 217 for vapor or gas transport from the geothermal source 200. The gases can be directed through a valve 227 to an expansion motor 229 (e.g., a turbine which is coupled to a load, e.g., a pump or a generator 231). The upper portion of the passage 217 can also communicate (via the valve 227) with one or more TCP reactors 226 which can be generally similar to those described above with regard to FIG. 2A. Hot gases or vapors produced by the reactor 226 can be directed to the expansion motor 229, e.g., via an insulated conduit 251. Within the bore tube 204 is a conduit 219 that is coupled with the motor-generator 213, e.g., at or near the bottom of the conduit 204. The conduit 219 can be disposed within the outer insulated conduit 215 in a concentric arrangement. At or near the top of the conduit 219 is a condenser or radiator 221 that is disposed at an elevated site 223, such as a tower for a wind turbine 225, a tall building, or a mountain.

In operation, the liquid 211 is vaporized by the heat provided by the geothermal source 200, and the vapor rises upwards through the passage 217 to the TCP reactor 226 via the valve 227. The valve 227 is controlled to provide the vapor to the TCP reactor 226 as needed, and/or to provide the vapor to the expansion motor (e.g., turbine) 229, and the generator 231. The generator 231 can provide power to the overall system. An exit 235 from the expansion motor 229 directs the exiting fluid (e.g., expanded vapors or gases) to the condenser or radiator 221 where it condenses to a liquid and is returned via the conduit 219 to the bottom of the bore tube 204 to repeat the cycle. The fluids (e.g., liquids) descending through the conduit 219 have a liquid head due to the elevation of the condenser 221, which can be extracted as work by the motor/generator 213. As described previously, the motor-generator 213 can be a reversible motor-generator or pump that can be operated as a motor-generator to produce electricity in one mode, and can be operated as a pump in another mode.

Figure 2C:
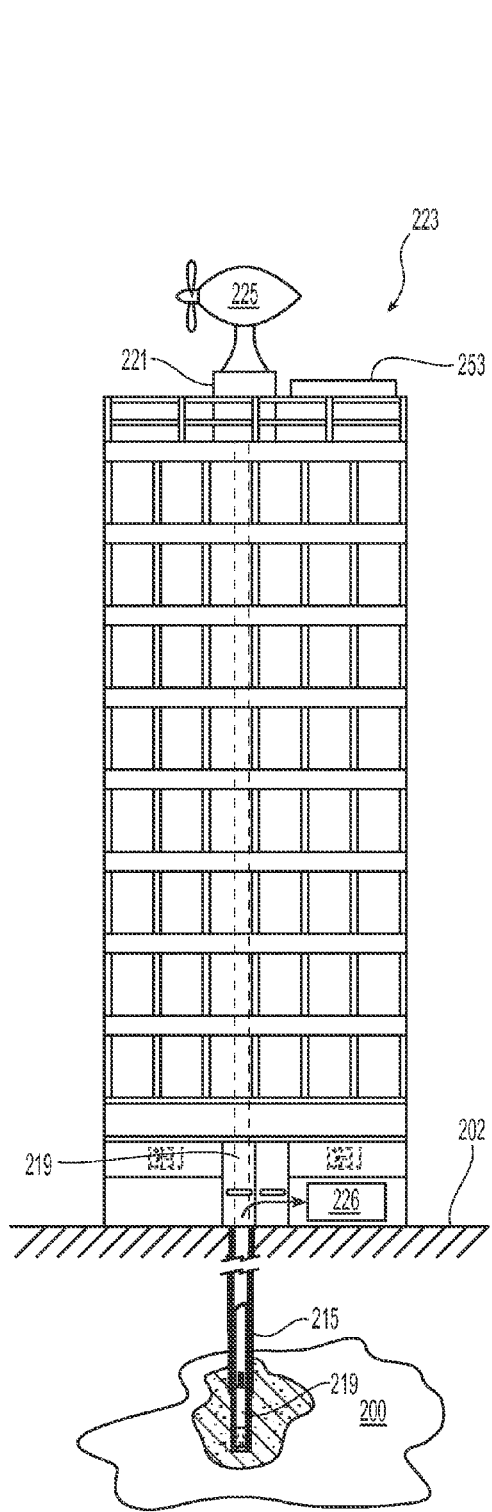
FIG. 2C is a partially schematic illustration of a closed system extending between an underground geothermal source and an elevated location on a representative building in accordance with an embodiment of the presently disclosed technology.
Figure 2D:
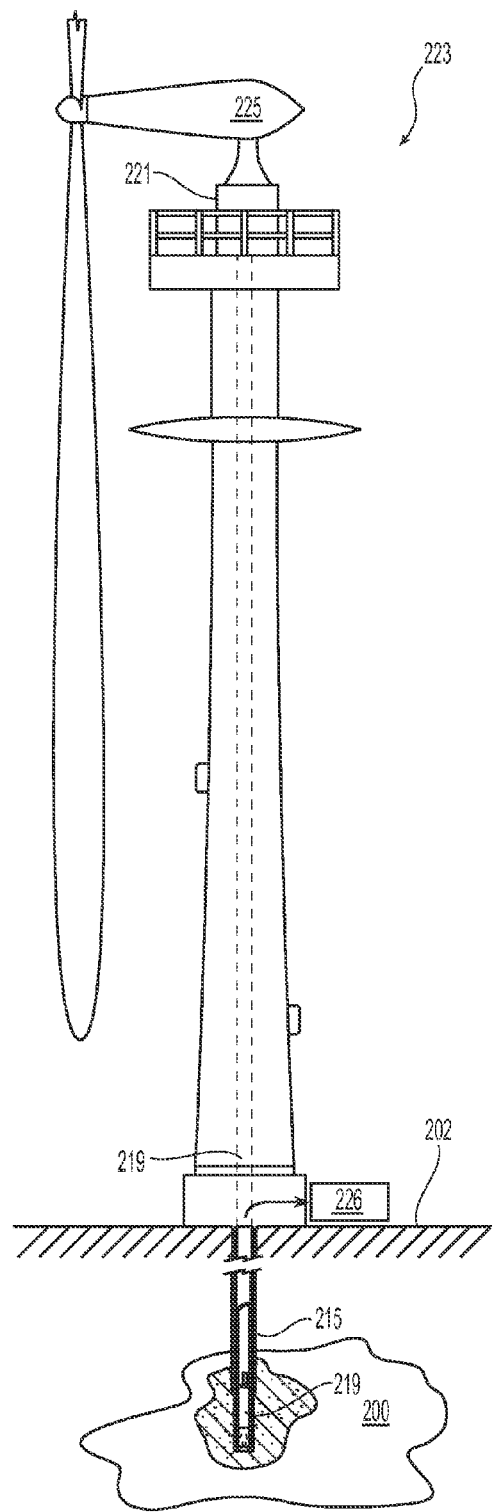
FIG. 2D is a partially schematic illustration of a closed system extending between an underground geothermal source and an elevated location on a representative tower in accordance with an embodiment of the presently disclosed technology.

FIG. 2C illustrates an elevated site 223 having the form of a tall building (optionally including a greenhouse 253), with the conduit 219 extending from the geothermal heat source 200 to the condenser or radiator 221 positioned on the elevated site 223. Heat transferred from the condenser 221 can be used to warm crops at the greenhouse 253, e.g., to extend the local growing season and/or increase productivity. FIG. 2D illustrates an elevated site 223 having the form of a tower (e.g., a wind turbine tower), with the conduit 219 extending from the geothermal heat source 200 to the condenser or radiator 221 carried by the tower. FIG. 2E illustrates an elevated site 223 having a suitable form, such as an offshore oil platform, with the conduit 219 extending from a submerged geothermal heat source 200 beneath the ocean bottom 237 to the condenser or radiator 221 positioned at an elevation on the platform at, near or above sea level 239. FIG. 2F illustrates an elevated site 223 having a suitable form, such as an electrical tower. In other embodiments, the elevated site 223 can be a natural formation, such as a hill or mountain. As can be appreciated, the elevated sites 223 shown in FIGS. 2C, 2D, 2E, and 2F each include the conduit 215 communicating with one or more TCP reactors 226 similar to those shown in the embodiment illustrated in FIGS. 2A and 2B, and can in at least some embodiments include a solar collector or a wind turbine 225 to provide additional power to the geothermally-heated TCP reactor system 201 illustrated in FIG. 2A.

Figure 3:
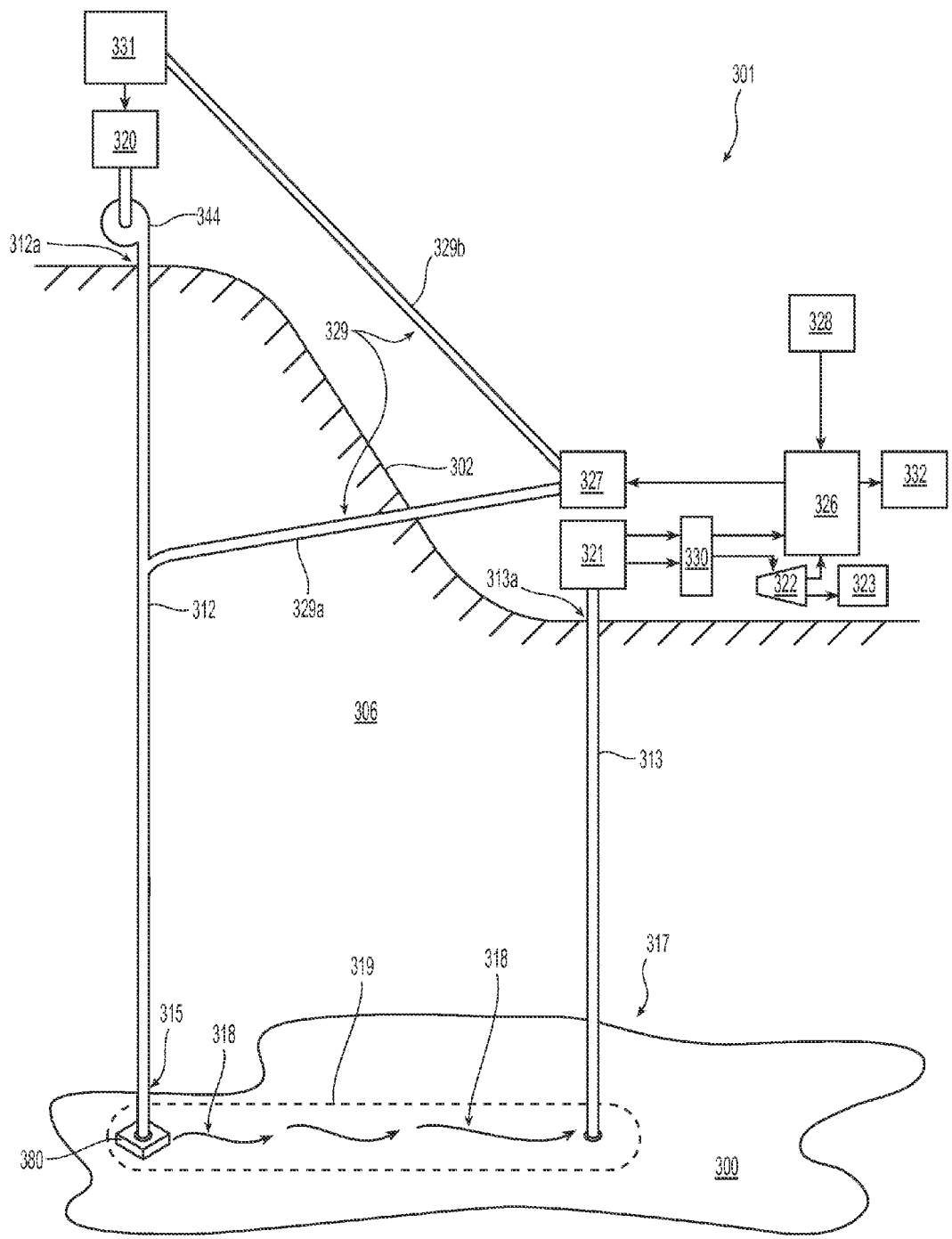
FIG. 3 is a partially schematic illustration of a thermochemical reactor heated by an open system having an elevated portion and communicating with a geothermal source in accordance with an embodiment of the presently disclosed technology.

FIG. 3 is a partially schematic illustration of another representative embodiment of a geothermally-heated TCP reactor system 301 in which a working fluid 318 is directed through a geo-formation via an open loop arrangement. For purposes of illustration, several of the valves (e.g., check valves) and other fluid control components used to control and/or regulate the flow of the working fluid 318 and/or other constituents are not shown in FIG. 3. The reactor system 301 can include a reactor 326 positioned to utilize a geothermal source 300 generally similar to the geothermal source 200 shown in FIG. 2A. In a representative embodiment shown in FIG. 3, a downflow pipe 312 extends through a bore in the ground 306 from the surface 302 to an entry portion 315 of the geothermal source 300. An upflow pipe 313 can be spaced apart from the downflow pipe 312 and can extend through a (different) bore in the ground 306 from the surface 302 to an exit portion 317 of the geothermal source 300. A geo-formation open flow path 319 is located between the entrance and exit portions 315, 317. The working fluid 318 (e.g., water, carbon dioxide or ammonia) passes along the flow path 319 when the geothermally-heated TCP reactor system 301 is operational. Accordingly, the downflow and upflow pipes 312, 313 and the flowpath 319 in part define an at least partially open loop. The working fluid 318 circulates around the loop through the geothermal source 300 to collect thermal energy and return the thermal energy to the reactor 326. Optionally, in certain embodiments the working fluid 318 can pass through one or more work extraction devices 322, 344, and 380 (e.g., turbines, turbo-generators, reversible pumps), that extract energy from the working fluid and provide the energy (e.g., in the form of electrical or shaft power) to the reactor 326.

In particular embodiments, the working fluid 318 intermixes with materials located at the geothermal source 300. Accordingly, the working fluid 318 may carry with it materials that can serve as a donor substance (e.g., a reactant) in the TCP reactor 326. In a representative embodiment, the material at the geothermal source 300 is petroleum from an oil or natural gas well or an oil deposit, with the hydrocarbons of the petroleum being carried by the working fluid 318 to the TCP reactor for processing as a donor substance.

In other embodiments, the working fluid can release and carry other constituents from the geothermal source 300 and/ or the proximate area, and can be particularly selected to release and carry such constituents. For example, hydrogen can be used as the working fluid and, due to its relatively high specific heat and low viscosity, can mobilize (e.g., release and carry) constituents that other working fluids (e.g., steam) may not. In a particular embodiment, hydrogen can be delivered to the geothermal source 300 and/or regions adjacent to the geothermal source 300, and can release and carry sulfur or other constituents. The sulfur can subsequently be retrieved (e.g., separated) from the working fluid and used for any of a number of suitable purposes. In another embodiment, the working fluid can include carbon dioxide, which can release and carry metals. Representative metals include carboneals, cobalt, and/or nickel. In a particular embodiment, a working fluid containing carbon dioxide and/or carbon monoxide can react underground with nickel to form $Ni_5CO$ which is then brought to the surface. At the surface, the nickel can be separated from the nickel-carbon compound and the carbon monoxide can be used as fuel. For example, the carbon monoxide can be further oxidized to form carbon dioxide, which can be combined with hydrogen to produce methanol or another suitable fuel. In still further embodiments, a carbon compound can be combined with iron located at the geothermal source 300 to produce iron carbonate, which is also removed from the geothermal source 300 and processed to remove the iron for other purposes. Other suitable metals, in addition to sulfur, nickel, iron, and cobalt include zinc and/or rare earth metals such as samarium and neodymium.

The system 301 can include a separator 330 that separates metals and/or other retrieved constituents from the working fluid e.g., before the working fluid enters the reactor 326. In other embodiments, the reactor 326 can be used to separate such constituents. In any of these embodiments, the working fluid can be used not only to retrieve energy from a geothermal source, but to retrieve minerals, metals, and/or other suitable constituents without the need for strip mining and/or other more destructive mining processes.

The working fluid 318 can be stored in a reservoir 320. At the reservoir 320, the working fluid 318 can be a vapor or liquid that is unpressurized and relatively cool as compared to the working fluid 318 within the upflow pipe 313. The reservoir 320 can have a higher elevation than an upper end 313a of the upflow pipe 313, which creates a pressure head that forces the working fluid 318 downward in the downflow pipe 312, which can include one or more check valves. The head can be supplemented with additional pressure provided by a reversible motor-generator or pump 344 if the additional pressure is necessary to drive the working fluid 318 downward. Accordingly, one or more pumps 344 can be located near an upper end 312a of the downflow pipe 312, and/or at other points along the working fluid loop.

In particular embodiments, the system 301 can also include a working fluid collector or buffer tank 321 that is located at the surface 302 and that collects and contains pressurized working fluid 318 that is relatively hot as compared to the working fluid 318 within downflow pipe 312. The working fluid 318 in the buffer tank 321 is typically pressurized as a result of the delivery head and the heat the working fluid 318 gains from the geothermal source 300, which can be sufficient to vaporize the working fluid 318. The elevated temperature and pressure in the buffer tank 321 are also in part due to the head pressure created by the elevation of the reservoir 320 relative to the buffer tank 321. To the extent the working fluid 318 in the buffer tank 321 has excess pressure, the excess can be provided to run a work extraction device 322 (e.g., a mixed-phase compatible turbine that operates a generator 323) which provides power to the TCP reactor system 301. In other embodiments, heat remaining in the expanded working fluid exiting the work extraction device 322 can be directed to the reactor 326, and/or heat can be provided from the buffer tank 321 directly to the reactor 326 (bypassing the work extraction device 322) as described below.

As shown in FIG. 3, the pressurized working fluid 318 in the buffer tank 321 is provided to the TCP reactor 326 to heat the reactor 326 and, in at least some cases provide a reactant to the reactor 326. The heat is conveyed to the TCP reactor 326 directing the working fluid 318 through a heat exchanger in the TCP reactor 326, as discussed above with reference to FIG. 2A. The working fluid 318 can then be returned up to the higher elevation reservoir 320 via one or more conduits or channels 329b. If, as a result of losing heat in the reactor 326, the working fluid 318 does not have enough energy to make the elevation change, the working fluid 318 can enter a separator or evaporator 327 after exiting the reactor 326. The working fluid 318 may be separated into a liquid portion and a gas or vapor portion that expands within the evaporator 327, with the liquid portion provided to a first channel 329a which may include one or more check valves and the gas or vapor portion provided to a second channel 329b which may also include one or more check valves. The second channel 329b delivers the vaporous working fluid 318 to a condenser 331. At the condenser 331, the working fluid 318 cools and condenses into a denser substance (e.g., a liquid) before entering the reservoir 320. The evaporator 327 and the second channel 329b may be heated to transform/maintain the working fluid 318 as a gas. In a representative embodiment, the evaporator 327 and/or the second channel 329b are heated by a solar concentrator and/or are colored black and/or include a selective surface to absorb and trap solar radiation and heat the working fluid 318.

As discussed above with reference to FIG. 2A, the TCP reactor 326 may be provided with supplemental heat by other heating sources, e.g., solar, wind, surplus electricity, and/or combustion heat sources. The TCP reactor 326 receives one or more reactant substances from one or more reactant sources 328. In a particular embodiment, the reactant source 328 is a storage tank, and the reactant substance is a hydrocarbon (e.g., methane or another petroleum substance). The reactant substance may be preheated by a heat exchanger that carries the working fluid 318. Reaction products exit the TCP reactor and are conveyed to a products collector 332. In the representative embodiment of FIG. 3, the reaction products may include hydrogen and carbon, and the products collector for the hydrogen is a storage tank. As discussed above with reference to FIG. 2A, any of the reaction products can also transfer heat to the incoming reactant substance via one or more heat exchangers. Any of the foregoing operations can be controlled by a controller, e.g., a controller similar to the controller 190 described above with reference to FIG. 2A.

Figure 4:
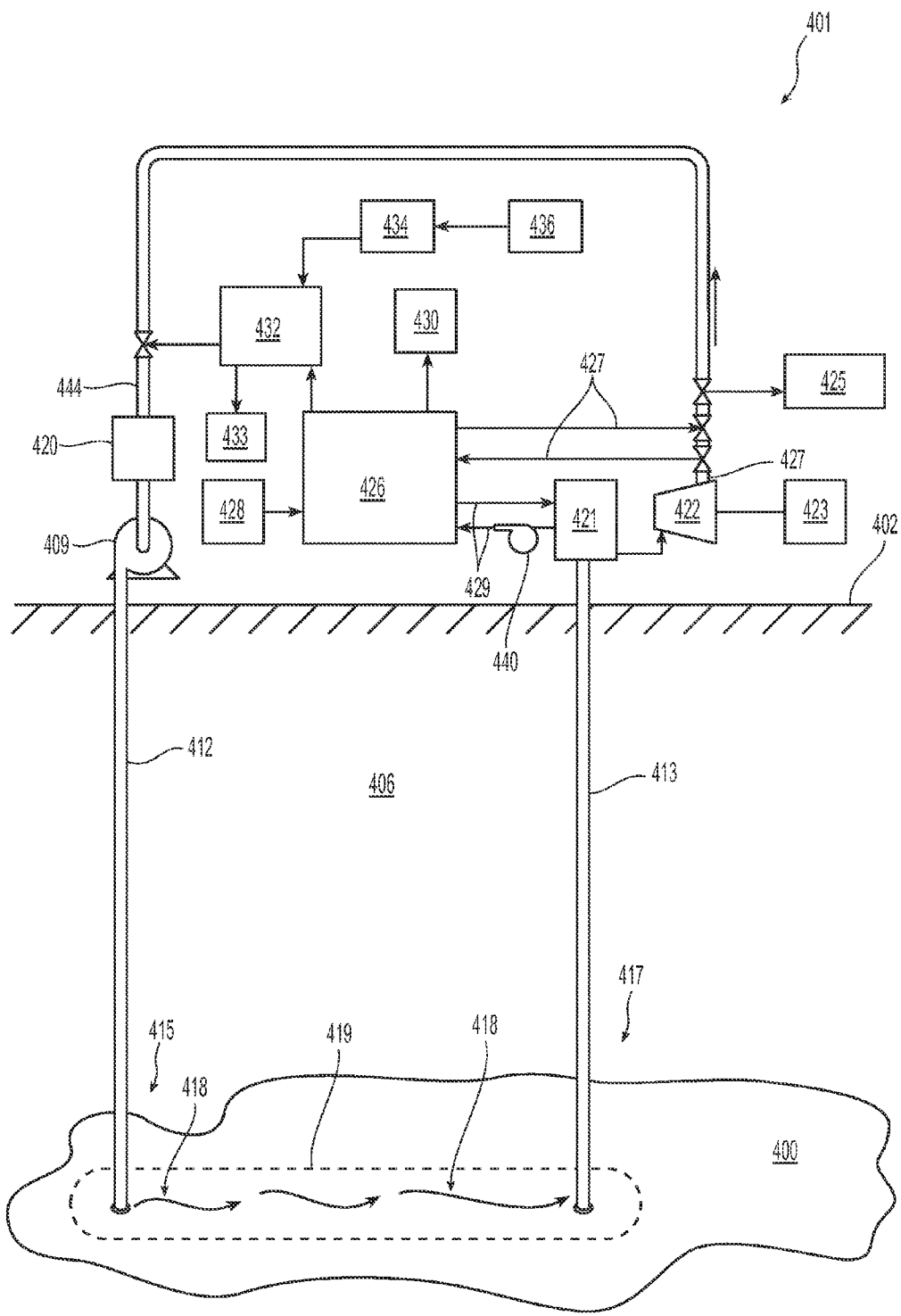
FIG. 4 is a partially schematic illustration of a thermochemical reactor heated by an open system communicating with a geothermal source in accordance with an embodiment of the presently disclosed technology.

FIG. 4 is a partially schematic illustration of another representative embodiment of a geothermally-heated TCP reactor system 401 positioned near a geothermal source 400 and configured to synthesize various substances, including a non-carbon compound, e.g., ammonia. In this embodiment, the geothermal source includes dry subterranean rock with relatively little or no water. A downflow pipe 412 (which may include one or more check valves) extends through a bore in the ground 406 from the surface 402 to an entrance portion 415 of the geothermal source 400, and an upflow pipe 413 extends through a bore in the ground 406 from the surface 402 to an exit portion 417 of the geothermal source 400. A flowpath 419 is positioned between the entrance and exit portions 415, 417, and a working fluid 418 (e.g., water, methanol, propane, or ammonia) passes along the flowpath 419 when the geothermally-heated TCP reactor system 401 is operational. The downflow and upflow pipes 412, 413 and the flowpath 419 define at least in part an open loop through which the working fluid 418 circulates through the geothermal source 400.

The system 401 can include a reservoir 420 that is located at, above or near the surface 402 and that contains unpressurized working fluid 418 that is relatively cool compared to the working fluid 418 within the upflow pipe 413. The reservoir 420 can be coupled to a reversible motor-generator or pump 409 that produces work or creates a pressure head driving the working fluid 418 downward in the downflow pipe 412. A buffer tank 421 contains pressurized working fluid 418 that is relatively hot as compared to the working fluid 418 within downflow pipe 412. The working fluid 418 in the buffer tank 421 is pressurized as a result of receiving heat from the geothermal source 400 and/or as a result of pressure applied by the head in the downflow pipe 412 and/or by the pump 409.

As shown in FIG. 4, the pressurized working fluid 418 in the buffer tank 421 is provided to a TCP reactor 426 to heat the reactor. For example, a portion of the working fluid 418 can be routed through a turbine 422, which drives a load such as generator 423, and then to the TCP reactor 426 via a relatively low-pressure loop 427 exiting the turbine 422. The generator 423 provides power to the TCP reactor system 401. The working fluid 418 can also be routed through the TCP reactor 426 via a pump 440 that drives the working fluid 418 from the buffer tank 421 to the TCP reactor 426 and back to the buffer tank 421 in a higher pressure return loop 429. The high pressure loop 429 can be provided in addition to or in lieu of the low pressure loop 427. A storage tank 425 can store excess working fluid 418. Similar to embodiments described above with reference to FIG. 2A, the TCP reactor 426 of FIG. 4 may be provided with supplemental heat by other heat sources, such as solar, electric, and/or combustion heat.

The TCP reactor 426 receives a reactant substance from a reactant source 428 (e.g., a storage tank). In a particular embodiment, the reactant substance is a hydrocarbon and/or includes water as a hydrogen donor. Accordingly, the reactor 426 dissociates the hydrocarbon into carbon and hydrogen, and/or the water into hydrogen and oxygen, and/or produces a compound of oxygen. The reactant substance may be preheated by the working fluid 418 supplied by buffer tank 421 or by routing the reactant substance through a heat exchanger (not shown) coupled to the buffer tank 421. The reaction products (e.g., hydrogen and oxygen or a compound of oxygen) exit the TCP reactor 426 and can preheat the incoming reactant substance, as discussed above with reference to FIG. 2A. In the representative embodiment of FIG. 4, the oxygen (or oxygen compound) portion of the reaction product is conveyed to an oxygen storage tank 430 or vented from the TCP reactor system 401, and the hydrogen is conveyed to a synthesizer 432. At the synthesizer 432, the hydrogen is combined with nitrogen by processes that can include but are not limited to catalytic processes or plasma synthesis using a spark or corona process. Any of these processes can produce ammonia which is conveyed to the low-pressure line 444 and/or to a storage tank 433. The nitrogen can be produced by an engine that depletes oxygen from air (e.g. for production of water or carbon dioxide) and/or by a separator or membrane 434 that removes oxygen from air received from a compressor 436.

Figure 5:
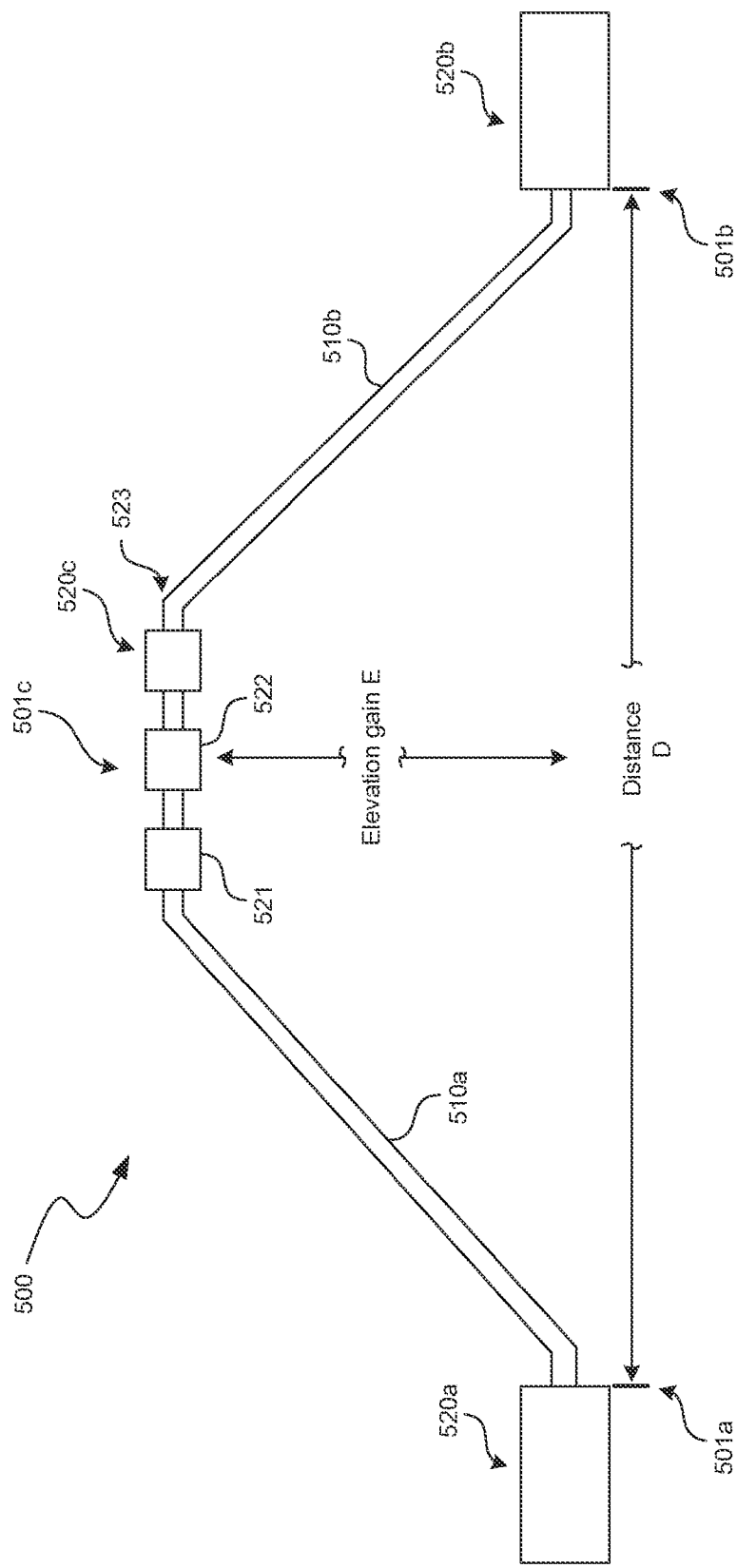
FIG. 5 is a partially schematic illustration of a system for transporting fluids from one site to another using elevation gain and phase change to assist in the transport, in accordance with an embodiment of the presently disclosed technology.

FIG. 5 is a partially schematic illustration of a system or subsystem 500 that can be used to transport fluids over a distance D, using phase change and an elevation gain E to facilitate the fluid transport. Accordingly, this arrangement can be used to transport fluids between, within, and/or among the geothermal sources and/or reactors described above. In a particular embodiment, the system 500 transports fluids from a first location 501a to a second location 501b. The first location 501a can include first location components 520a, and the second location 501b can include second location components 520b. The components at each location can include pumps, chemical reactors, expanders, work extraction devices, and/or other elements used to facilitate transporting and/or using the fluid. In particular embodiments, arrangements having these configurations can be used in place of the first and second channels 329a, 329b (shown in FIG. 3) to transport a working fluid used to capture geothermal energy. Accordingly, the first location 501a can correspond to a site where a gas-phase working fluid is removed from the ground (e.g., the upper end 313a of the upflow pipe 313 shown in FIG. 3), and the second location 501b can correspond to the upper end 312a of the downflow pipe 312 shown in FIG. 3.

As shown in FIG. 5, an arrangement of conduits or other fluid conveyances transports a fluid (e.g., a working fluid) from the first location 501a to the second location 501b, via the elevation gain E. For purposes of illustration, the first and second locations 501a, 501b are shown at the same elevation. In other embodiments, the first and second locations 501a, 501b can be at different elevations, but in general, have an intermediate location 501c positioned between them. Accordingly, the conduits can include a first conduit portion 510a that connects the first location 501a with an intermediate location 501c having an elevation greater than that of the first location 501a and the second location 501b. The conduits can further include a second conduit portion 510b connected between the intermediate location 501c and the second location 501b. A gaseous fluid at the first location 501a can be stored in and/or expand and rise through the first conduit portion 510a to the intermediate location 501c, thus traveling over a portion of the distance D separating the first and second locations 501a, 501b. At the intermediate location 501c, one or more intermediate location components (e.g., phase change devices) 520c can be used to change the phase of the fluid from vapor to liquid, thus allowing the fluid to flow to the second location 501b via the second conduit portion 510b under the force of gravity. The phase change devices 520c can include an expander 521 that cools the fluid sufficiently to condense it, and/or a compressor that compresses the vapor to condense it. In particular embodiments, the phase change devices 502 and/or other devices can extract energy from the fluid, in addition to changing the phase of the fluid. For example, the fluid can be expanded through a turbine. Other intermediate location components 520c, in addition to or in lieu of the expander and/or compressor can include a heat exchanger 522 (e.g., a condenser) that dissipates heat from the fluid to the environment, causing it to cool and condense. In still a further embodiment, the intermediate location components 520c can include a mixer 523 that introduces another constituent to the fluid passing through the intermediate location 501c. For example, gaseous hydrogen can travel from the first location 501a to the intermediate location 501c and at the intermediate location 501c, can be combined with nitrogen to form ammonia. The liquid ammonia can then flow downhill from the intermediate location 501c to the second location 501b. At the second location 501b, the ammonia can be reintroduced as a working fluid to the geothermal source. In particular embodiments, the ammonia can be expanded, e.g., through a gas turbine to provide additional power. In other embodiments, the second location 501b can include other components (e.g., liquid-powered turbines) that extract the "head" energy from the fluid resulting from elevation drop from the intermediate location 501c to the second location 501b. Other representative combinations, without limitation, include combining hydrogen with chlorine to form HCl, combining hydrogen with oxygen to form water, combining hydrogen with SO2 to form H2SO2 and combining hydrogen with nitrogen to form ammonia.

In yet a further embodiment, the mixer 523 can be replaced with a separator, e.g., to separate constituents brought up by the working fluid as it passes through the geothermal source 300 (FIG. 3). While particular embodiments of the system 500 were described above in the context of the open loop working fluid arrangement show in FIG. 3, the system can also be applied in the context of a closed loop system, e.g., as shown in FIGS. 2A-2F.

Systems of the type shown in FIG. 5 can be used in any of a variety of contexts, and can be combined to provide still further benefits. For example, in some embodiments, the heat exchanger 522 can be integrated with the first conduit portion 510a and/or the second conduit portion 510b. For example, the conduit portion(s) can be fitted with cooling fins or other features that cool the fluid inside without the need for a separate heat exchanger. Several systems of the type shown in FIG. 5 can be connected in series to increase the distance over which the fluid is transported. While a particular example was described above in the context of hydrogen, with an optional addition of carbon to produce methanol, in other embodiments, the system can be used to transport other fluids, with or without constituent mixing at the intermediate location 501c.

In representative embodiments, the elevation gain E can have a value of at least 50 feet. In particular embodiments, the elevation gain can have a value of at least 500 feet, at least 1,000 feet, at least 2,000 feet or at least 3,000 feet. In any of these embodiments, it is expected that the increase in elevation allows the liquefied fluid to flow "downhill" to the second location 501b under the force of gravity. In operation, the first conduit portion 510a can be filled with fluid at an elevated pressure, e.g., 100 psi. Accordingly, the first conduit portion 510a can operate as a reservoir or storage site for the fluid, in addition to a fluid transport device. As fluid is drawn off the first conduit portion 510a for delivery to the second location 501b (which may be on an intermittent basis, depending upon need), the first location components 520a replenish the supply of liquid in the first conduit portion 510a.

4. Further Representative Reactors

The following sections describe representative reactors and associated systems that may be used alone or in any of a variety of suitable combinations for carrying out one or more of the foregoing processes described above with reference to FIGS. 1-4. In particular, any suitable component of the systems described in the following sections may replace or supplement a suitable component described in the foregoing sections.

In some embodiments, the reactants may be obtained on a local scale, the reactions may be conducted on a local scale, and the products may be used on a local scale to produce a localized result. In other embodiments, the reactants, reactions, products and overall effect of the process can have a much larger effect. For example, the technology can have continental and/or extra-continental scope. In particular embodiments, the technology can be deployed to preserve vast regions of permafrost, on a continental scale, and or preserve ecosystems located offshore from the preserved areas. In other embodiments, the technology can be deployed offshore to produce effects over large tracts of ocean waters. In still further, embodiments, the technology can be deployed on mobile systems that convey the benefits of the technology to a wide range of areas around the globe.

In general, the disclosed reactors dissociate, reform and/or respeciate a donor material (reactant) into multiple constituents (e.g., a first constituent and a second constituent). Particular aspects of the representative reactors described below are described in the context of specific reactants and products, e.g., a hydrogen and carbon bearing donor, a hydrogen-bearing product or constituent, and a carbon-bearing product or constituent. In certain other embodiments of the disclosed technology, the same or similar reactors may be used to process other reactants and/or form other products. For example, non-hydrogen feedstock materials (reactants) are used in at least some embodiments. In particular examples, sulfur dioxide can be processed in a non-combustion thermal reactor to produce sulfur and oxygen, and/or carbon dioxide can be processed to produce carbon and oxygen. In many of these embodiments, the resulting dissociation products can include a structural building block and/or a hydrogen-based fuel or other dissociated constituent. The structural building block includes compositions that may be further processed to produce architectural constructs. For example, the structural building blocks can include compounds or molecules resulting from the dissociation process and can include carbon, various organics (e.g. methyl, ethyl, or butyl groups or various alkenes), boron, nitrogen, oxygen, silicon, sulfur, halogens, and/or transition metals. In many applications the building block element does not include hydrogen. In a specific example, methane is dissociated to form hydrogen (or another hydrogen-bearing constituent) and carbon and/or carbon dioxide and/or carbon monoxide (structural building blocks). The carbon and/or carbon dioxide and/or carbon monoxide can be further processed to form polymers, graphene, carbon fiber, and/or another architectural construct. The architectural construct can include a self-organized structure (e.g., a crystal) formed from any of a variety of suitable elements, including the elements described above (carbon, nitrogen, boron, silicon, sulfur, and/or transition metals). In any of these embodiments, the architectural construct can form durable goods, e.g., graphene or carbon composites, and/or other structures.

Many embodiments are described in the context of hydrocarbons, e.g., methane. In other embodiments, suitable hydrogen-bearing feedstocks (e.g., reactants) include boranes (e.g., diborane), silanes (e.g., monosilane), nitrogen-containing compounds (e.g., ammonia), sulfides (e.g., hydrogen sulfide), alcohols (e.g., methanol), alkyl halides (e.g., carbon tetrachloride), aryl halides (e.g., chlorobenzene), and hydrogen halides (e.g., hydrochloric acid), among others. For example, silane can be thermally decomposed to form hydrogen as a gaseous product and silicon as a non-gaseous product. When the non-gaseous product includes silicon, the silicon can be reacted with nitrogen (e.g., from air) or with a halogen gas (e.g., recycled from a separate industrial process) to form useful materials, such as silicon nitride (e.g., as a structural material) or a silicon halide (e.g., as a non-structural material). In other embodiments, the feedstock material can be reacted to form only gaseous products or only non-gaseous products. For example, suitable hydrogen halides can be thermally decomposed to form a combination of hydrogen and halogen gas as the gaseous product with no accompanying non-gaseous product. In some embodiments, the gaseous product can include a gaseous fuel (e.g., hydrogen) and/or the non-gaseous product can include an elemental material (e.g., carbon or silicon). In some embodiments, the system can be configured for use in close proximity to a suitable source of the feedstock material. For example, the system can be configured for use near landfills and for processing methane that would otherwise be flared or released into the atmosphere. In other embodiments, the system can be configured for processing stranded well gas at oil fields, methane hydrates from the ocean floors or permafrost sources, and/or other feedstock materials 180 that would otherwise be wasted.

In some embodiments, the non-gaseous product can be further processed in a reactor. For example, the non-gaseous product can be a structural building block that can be further processed in the reactor to produce a structural material, e.g., a ceramic, a carbon structure, a polymeric structure, a film, a fiber (e.g., a carbon fiber or a silicon fiber), or a filter. Highly pure forms of the non-gaseous product can be especially well suited for forming semiconductor devices, photo-optical sensors, and filaments for optical transmission, among other products. The non-gaseous product can also be used without further processing and/or can be reacted to form materials useful for non-structural applications.

In other embodiments, the carbon can be used as a structural material or used as a reactant for producing a structural material. For example, the carbon can be a reactant for extracting silicon from silica as shown in Equations R1 and/or R2 below.

$$C+SiO_2 \rightarrow CO_2+Si \qquad \text{Equation R1}$$

$$2C+SiO_2 \rightarrow 2CO+Si \qquad \text{Equation R2}$$

Silicon from the reactions shown in Equations R1 and R2 or as the non-gaseous product may be formed, for example, in a granular (e.g., powder) form, which can include controlled amounts of amorphous and/or crystalline material. For example, the operating temperature of the reactor can be programmed or otherwise controlled to control when, where, and/or whether the silicon is deposited in amorphous or crystalline form.

In some embodiments, silicon from the system can be reacted to form halogenated silanes or silicon halides, e.g., $SiBrH_3$, $SiBrFH_2$, $SiBrH_3$, $SiBr_3H$, $SiCl_2H_2$, $SiBr_4$, or $SiCl_4$, among others. Furthermore, silicon from the system may be made into various useful products and materials, such as products that are produced from or based on specialized forms of silicon (e.g., fumed silica), silicon-containing organic intermediates, and silicon-containing polymers, among others. Such products can be formed, for example, using suitable processes disclosed in U.S. Pat. Nos. 4,814,155, 4,414,364, 4,243,779, and 4,458,087, which are incorporated herein by reference. Silicon from the system 100 can also be used in the production of various substances, such as silicon carbide or silicon nitride, e.g., as shown in Equation R3.

$$3Si+2N_2 \rightarrow Si_3N_4 \qquad \text{Equation R3}$$

Silicon nitride articles can be formed, for example, using silicon powders that are slip cast, pressure compacted, or injection molded and then converted into silicon nitride. The resulting articles can have density, fatigue, endurance, dielectric, and/or other properties well suited for a variety of high-performance applications. Silicon-nitride-based durable goods can be used, for example, in thermally and electrically insulating components that have lower densities and can operate at higher operating temperatures than metal alloys typically used in rocket engines, gas turbines, and positive-displacement combustion engines. Replacing such metal alloys, which typically consume critical supplies of cobalt, nickel, refractory metals, and rare earths with silicon nitride and/or carbon components, can enable far more cost-effective production of engines, fuel cells, and other equipment.

In addition to forming inorganic materials, the system can form a variety of useful organic materials. For example, the feedstock material can include propane or propylene, which can be reacted with ammonia in the first mode according to the reactions shown in Equations R4 and R5 to form acrylonitrile and hydrogen as the gaseous products or electrolytically disassociated in the second mode to generate electricity.

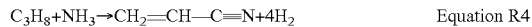

Equation R4

Equation R5

Subsequent processing of the gaseous products including acrylonitrile can include reacting the acrylonitrile to form polymers, rubbers, carbon fiber, and/or other materials well suited for use in durable goods (e.g., equipment to harness solar, wind, moving water, or geothermal energy). Accordingly, the overall energetics of processing propane or propylene using the system can be significantly more favorable than simple combustion. Furthermore, in some cases, processing propane or propylene using the system can produce little or no harmful pollution (e.g., environmentally released carbon dioxide, oxides of nitrogen, or particulates) or significantly less harmful pollution relative to simple combustion.

In some embodiments, one or more chemical reaction products from operation of the system can be used to form dielectric materials for use in durable goods. For example, the reaction products can be used to form polymers (e.g., polyimides, polyetherimides, parylenes, or fluoropolymers) and/or inorganic dielectrics (e.g., silicon dioxide or silicon nitride) that can incorporated into polymer-based nanodielectrics. Composites of inorganic and organic materials (one or both of which can be produced by operation of the system) can provide relatively high dielectric and mechanical strengths along with flexibility. Such materials can be well suited for use at a wide range of temperatures, such as temperatures ranging from cryogenic temperatures (e.g., about −200° C.) to heat-engine exhaust temperatures (e.g., about 500° C.). In other embodiments, the reaction products can be used to form thin films of inorganic amorphous carbon, silicon oxynitride, aluminum oxynitride, or other suitable materials. In some embodiments, the system can have dual-beam deposition and/or web-handling capabilities useful for processing suitable chemical reaction products (e.g., to form amorphous or crystalline carbon films).

In at least some embodiments, nitrogen can be obtained as a product or an exhaust stream. The nitrogen can be combined with hydrogen to produce ammonia and/or can be otherwise processed to form other useful materials such as $Si_3N_4$, AlN, BN, TiN, ZrN, $TiCSi_3N_4$, and/or suitable sialons.

While any one or more of the following representative reactors and associated components, devices and methodologies may be used in conjunction with the systems described above, certain reactors may have particularly synergistic and/or otherwise beneficial effects in such embodiments. For example, one or more heat pipes described below under heading 4.3 may be used to transfer fluid and heat between a subterranean heat source and the surface to facilitate dissociation or respeciation of methane or another hydrogen donor.

4.1 Representative Reactors with Transmissive Surfaces

Figure 16:
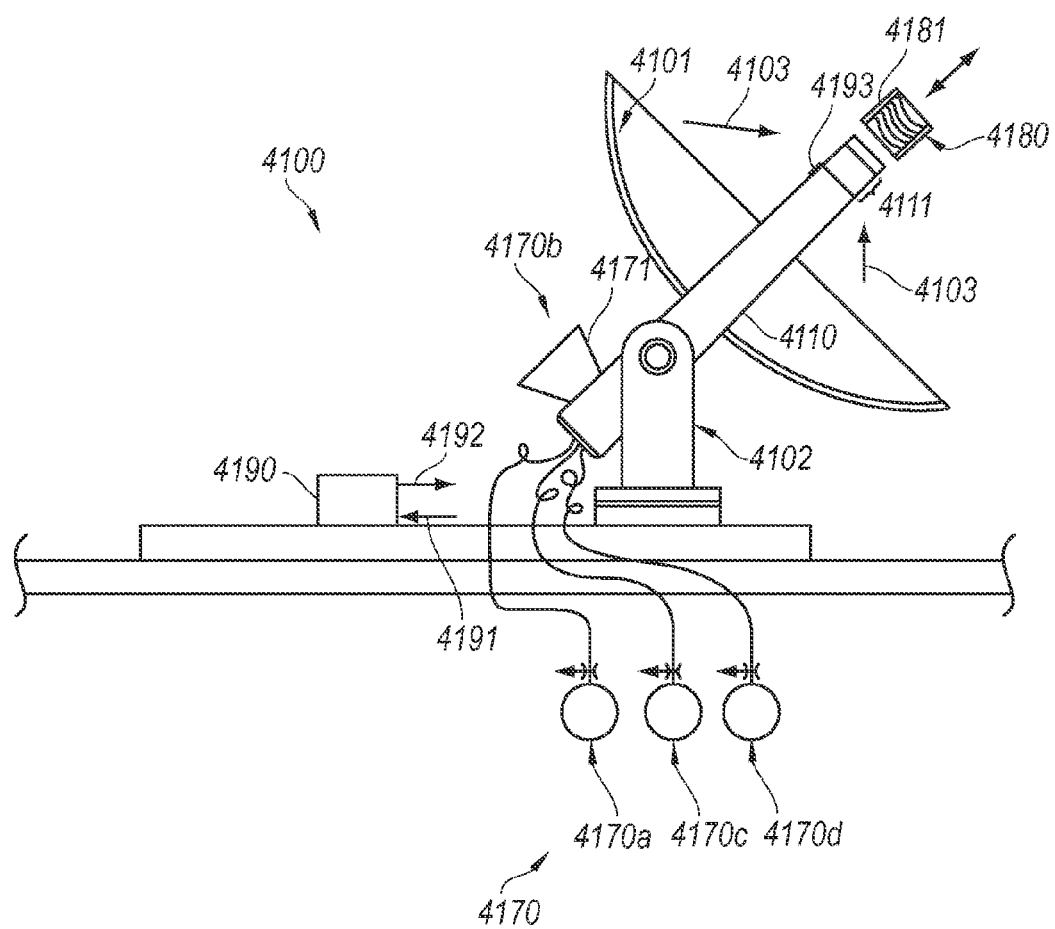
FIG. 16 is a partially schematic illustration of a system having a solar concentrator that directs heat to a reactor vessel in accordance with an embodiment of the disclosed technology.

FIG. 16 is a partially schematic illustration of a system 1100 that includes a reactor 1110. The reactor 1110 further includes a reactor vessel 1111 that encloses or partially encloses a reaction zone 1112. The reactor vessel 1111 has one or more transmissive surfaces positioned to facilitate the chemical reaction taking place within the reaction zone 1112.

In a representative example, the reactor vessel 1111 receives a hydrogen donor provided by a donor source 1130 to a donor entry port 1113. For example, the hydrogen donor can include a nitrogenous compound such as ammonia or a compound containing carbon and hydrogen such as methane or another hydrocarbon. The hydrogen donor can be suitably filtered before entering the reaction zone 1112 to remove contaminants, e.g., sulfur. A donor distributor or manifold 1115 within the reactor vessel 1111 disperses or distributes the hydrogen donor into the reaction zone 1112. The reactor vessel 1111 also receives an oxygen donor such as an alcohol or steam from a steam/water source 1140 via a steam entry port 1114. A steam distributor 1116 in the reactor vessel 1111 distributes the steam into the reaction zone 1112. The reactor vessel 1111 can further include a heater 1123 that supplies heat to the reaction zone 1112 to facilitate endothermic reactions. Such reactions can include dissociating a compound such as a nitrogenous compound, or a compound containing hydrogen and carbon such as methane or another hydrocarbon into hydrogen or a hydrogen compound, and carbon or a carbon compound. The products of the reaction exit the reactor vessel 1111 via an exit port 1117 and are collected at a reaction product collector 1160a.

The system 1100 can further include a source 1150 of radiant energy and/or additional reactants, which provides constituents to a passage 1118 within the reactor vessel 1111. For example, the radiant energy/reactant source 1150 can include a combustion chamber 1151 that provides hot combustion products 1152 to the passage 1118, as indicated by arrow A. A combustion products collector 1160b collects combustion products exiting the reactor vessel 1111 for recycling and/or other uses. In a particular embodiment, the combustion products 1152 can include carbon dioxide, carbon monoxide, water vapor, and other constituents. One or more transmissive surfaces 1119 are positioned between the reaction zone 1112 (which can be disposed annularly around the passage 1118) and an interior region 1120 of the passage 1118. The transmissive surface 1119 can accordingly allow radiant energy and/or a chemical constituent to pass radially outwardly from the passage 1118 into the reaction zone 1112, as indicated by arrows B. By delivering the radiant energy and/or chemical constituent(s) provided by the flow of combustion products 1152, the system 1100 can enhance the reaction taking place in the reaction zone 1112, for example, by increasing the reaction zone temperature and/or pressure, and therefore the reaction rate, and/or the thermodynamic efficiency of the reaction. Similarly, a chemical constituent such as water or steam can be recycled or otherwise added from the passage 1118 to replace water or steam that is consumed in the reaction zone 1112. In a particular aspect of this embodiment, the combustion products and/or other constituents provided by the source 1150 can be waste products from another chemical process (e.g., an internal combustion process). Accordingly, the foregoing process can recycle or reuse energy and/or constituents that would otherwise be wasted, in addition to facilitating the reaction at the reaction zone 1112.

The composition and structure of the transmissive surface 1119 can be selected to allow radiant energy to readily pass from the interior region 1120 of the passage 1118 to the reaction zone 1112. For example, the transmissive surface 1119 can include glass or another material that is transparent or at least partially transparent to infrared energy and/or radiant energy at other wavelengths that are useful for facilitating the reaction in the reaction zone 1112. In many cases, the radiant energy is present in the combustion product 1152 as an inherent result of the combustion process. In other embodiments, an operator can introduce additives into the stream of combustion products 1152 to increase the amount of energy extracted from the stream and delivered to the reaction zone 1112 in the form of radiant energy. For example, the combustion products 1152 can be seeded with sodium, potassium, and/or magnesium, which can absorb energy from the combustion products 1152 and radiate the energy outwardly through the transmissive surface 1119. In particular embodiments, the walls of the reaction zone 1112 can be dark and/or can have other treatments that facilitate drawing radiant energy into the reaction zone 1112. However, it is also generally desirable to avoid forming particulates and/or tars, which may be more likely to form on dark surfaces. Accordingly, the temperature on the reaction zone 1112 and the level of darkness can be controlled/selected to produce or to prevent tar/particulate formation.

In particular embodiments, the process performed at the reaction zone includes a conditioning process to produce darkened radiation receiver zones, for example, by initially providing heat to particular regions of the reaction zone 1112. After these zones have been heated sufficiently to cause dissociation, a small amount of a hydrogen donor containing carbon is introduced to cause carbon deposition or deposition of carbon-rich material. Such operations may be repeated as needed to restore darkened zones as desired.

In another particular aspect of this embodiment, the process can further includes preventing undesirable solids or liquids, such as particles and/or tars produced by dissociation of carbon donors, from forming at certain areas and/or blocking passageways including the entry port 1113 and the distributor 1115. This can be accomplished by supplying heat from the heater 1123 and/or the transmissive surface 1119 to an oxygen donor (such as steam) to heat the oxygen donor. When the oxygen donor is heated sufficiently, it can supply the required endothermic heat and react with the carbon donor without allowing particles or tar to be formed. For example, a carbon donor such as methane or another compound containing carbon and hydrogen receives heat from steam to form carbon monoxide and hydrogen and thus avoids forming of undesirable particles and/or tar.

As noted above, the combustion products 1152 can include steam and/or other constituents that may serve as reactants in the reaction zone 1112. Accordingly, the transmissive surface 1119 can be manufactured to selectively allow such constituents into the reaction zone 1112, in addition to or in lieu of admitting radiant energy into the reaction zone 1112. In a particular embodiment, the transmissive surface 1119 can be formed from a carbon crystal structure, for example, a layered graphene structure. The carbon-based crystal structure can include spacings (e.g., between parallel layers oriented transverse to the flow direction A) that are deliberately selected to allow water molecules to pass through. At the same time, the spacings can be selected to prevent useful reaction products produced in the reaction zone 1112 from passing out of the reaction zone. Suitable structures and associated methods are further disclosed in pending U.S. patent application Ser. No. 12/857,228 titled "ARCHITECTURAL CONSTRUCT HAVING FOR EXAMPLE A PLURALITY OF ARCHITECTURAL CRYSTALS" filed Feb. 14, 2011 and incorporated herein by reference. The structure used to form the transmissive surface 1119 can be carbon-based, as discussed above, and/or can be based on other elements capable of forming a self-organized structures, or constituents capable of modifying the surface of 1119 to pass or re-radiate particular radiation frequencies, and/or block or pass selected molecules. Such elements can include transition metals, boron, nitrogen, silicon, and sulfur, among others. In particular embodiments, the transmissive surface 1119 can include re-radiating materials selected to re-radiate energy at a wavelength that is particularly likely to be absorbed by one or more reactants in the reaction zone 1112. The walls of the reaction zone 1112 can include such material treatments in addition to or in lieu of providing such treatments to the transmissive surface 1119. Further details of such structures, materials and treatments are disclosed below in Section 4.2.

The system 1100 can further include a controller 1190 that receives input signals 1191 (e.g., from sensors) and provides output signals 1192 (e.g., control instructions) based at least in part on the inputs 1191. Accordingly, the controller 1190 can include suitable processor, memory and I/O capabilities. The controller 1190 can receive signals corresponding to measured or sensed pressures, temperatures, flow rates, chemical concentrations and/or other suitable parameters, and can issue instructions controlling reactant delivery rates, pressures and temperatures, heater activation, valve settings and/or other suitable actively controllable parameters. An operator can provide additional inputs to modify, adjust and/or override the instructions carried out autonomously by the controller 1190.

One feature of forming the transmissive surface 1119 from graphene or other crystal structures is that it can allow both radiant energy and useful constituents (e.g., water) to pass into the reaction zone 1112. In a particular embodiment, the spacing between graphene layers can be selected to "squeeze" or otherwise orient water molecules in a manner that tends to present the oxygen atom preferentially at the reaction zone 1112. Accordingly, those portions of the reaction that use the oxygen (e.g., oxidation or oxygenation steps) can proceed more readily than they otherwise would. As a result, this mechanism can provide a further avenue for facilitating the process of dissociating elements or compounds from the hydrogen donor and water, (and/or other reactants) and reforming suitable end products.

Figure 7:
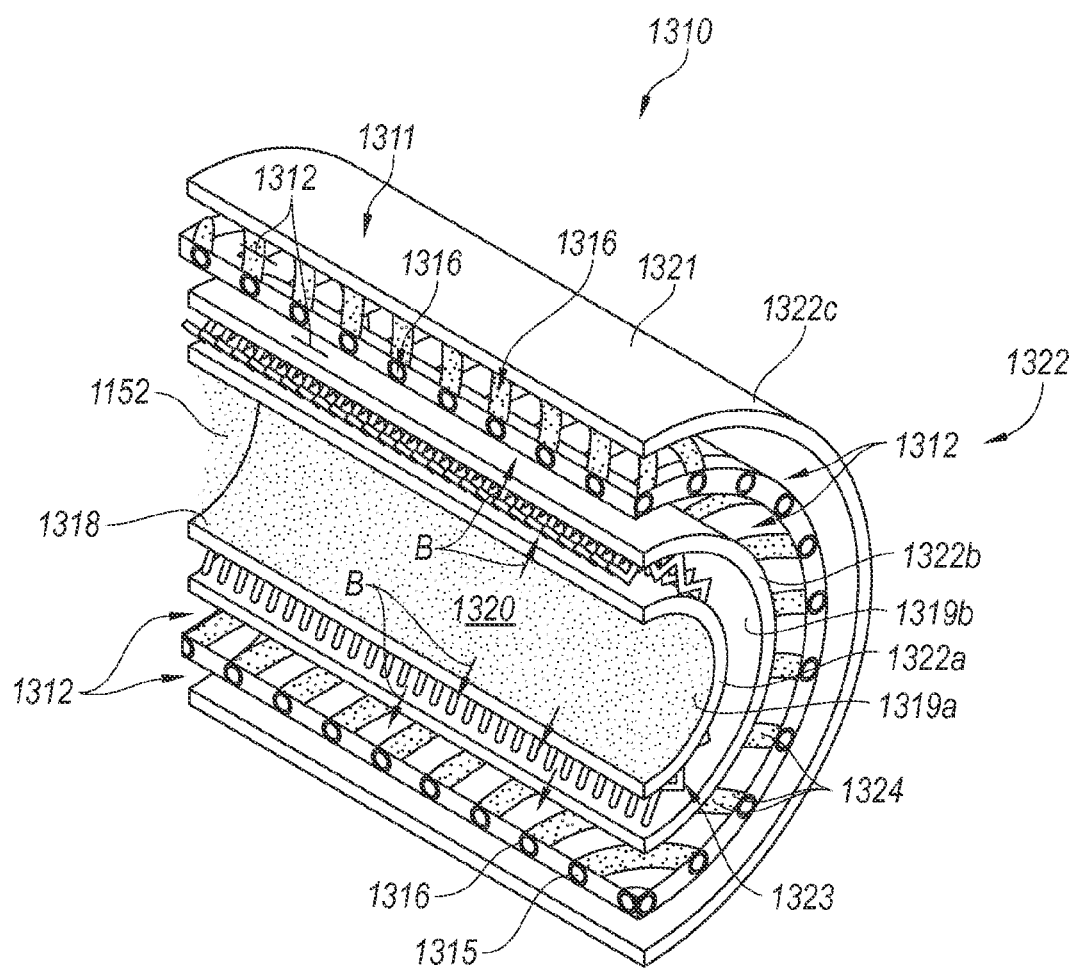
FIG. 7 is a partially schematic, cut-away illustration of a portion of a reactor having transmissive surfaces positioned annularly in accordance with an embodiment of the disclosed technology.

FIG. 7 is a partially schematic, partially cut-away illustration of a reactor 1310 that includes a vessel 1311 formed from three annularly (e.g., concentrically) positioned conduits 1322. Accordingly, the reactor 1310 can operate in a continuous flow manner. As used herein, "continuous flow" refers generally to a process in which reactants and products can be provided to and removed from the reactor vessel continuously without halting the reaction to reload the reaction zone with reactants. In other embodiments, the reactor 1310 can operate in a batch manner during which reactants are intermittently supplied to the reaction zone and products are intermittently removed from the reaction zone. The three conduits 1322 include a first or inner conduit 1322*a*, a second or intermediate conduit 1322*b*, and a third or outer conduit 1322*c*. The first conduit 1322*a* bounds a combustion products passage 1318 and accordingly has an interior region 1320 through which the combustion products 1152 pass. The first conduit 1322*a* has a first transmissive surface 1319*a* through which radiant energy passes in a radially outward direction, as indicated by arrows B. In a particular aspect of this embodiment, the annular region between the first conduit 1322*a* and the second conduit 1322*b* houses a heater 1323, and the annular region between the second conduit 1322*b* and the third conduit 1322*c* houses a reaction zone 1312. The heater 1323 together with the radiant heat from the combustion products 1152 provides heat to the reaction zone 1312. Accordingly, the second conduit 1322*b* can include a second transmissive surface 1319*b* that allows radiant energy from both the combustion products 1152 and the heater 1323 to pass radially outwardly into the reaction zone 1312. In a particular aspect of this embodiment, the first transmissive surface 1319*a* and the second transmissive surface 1319*b* are not transmissible to chemical constituents of the combustion products 1152, in order to avoid contact (e.g., corrosive or other damaging contact) between the combustion products 1152 and the heater 1323. In another embodiment, the heater 1323 can be manufactured (e.g., with appropriate coatings, treatments, or other features) in a manner that protects it from chemical constituents passing through the first and second transmissive surfaces 1319a, 1319b. In still another embodiment, the heater 1323 can be positioned outwardly from the reaction zone 1312. In any of these embodiments, the heater 1323 can include an electrical resistance heater, an induction heater or another suitable device. In at least some instances, the heater 1323 is powered by combusting a portion of the hydrogen produced in the reaction zone 1312. In other embodiments, combustion is performed in the reactor itself, for example, with the second conduit 1322b serving as a gas mantle for radiating energy at frequencies selected to accelerate the desired reactions in reaction zone 1312.

Figure 6:
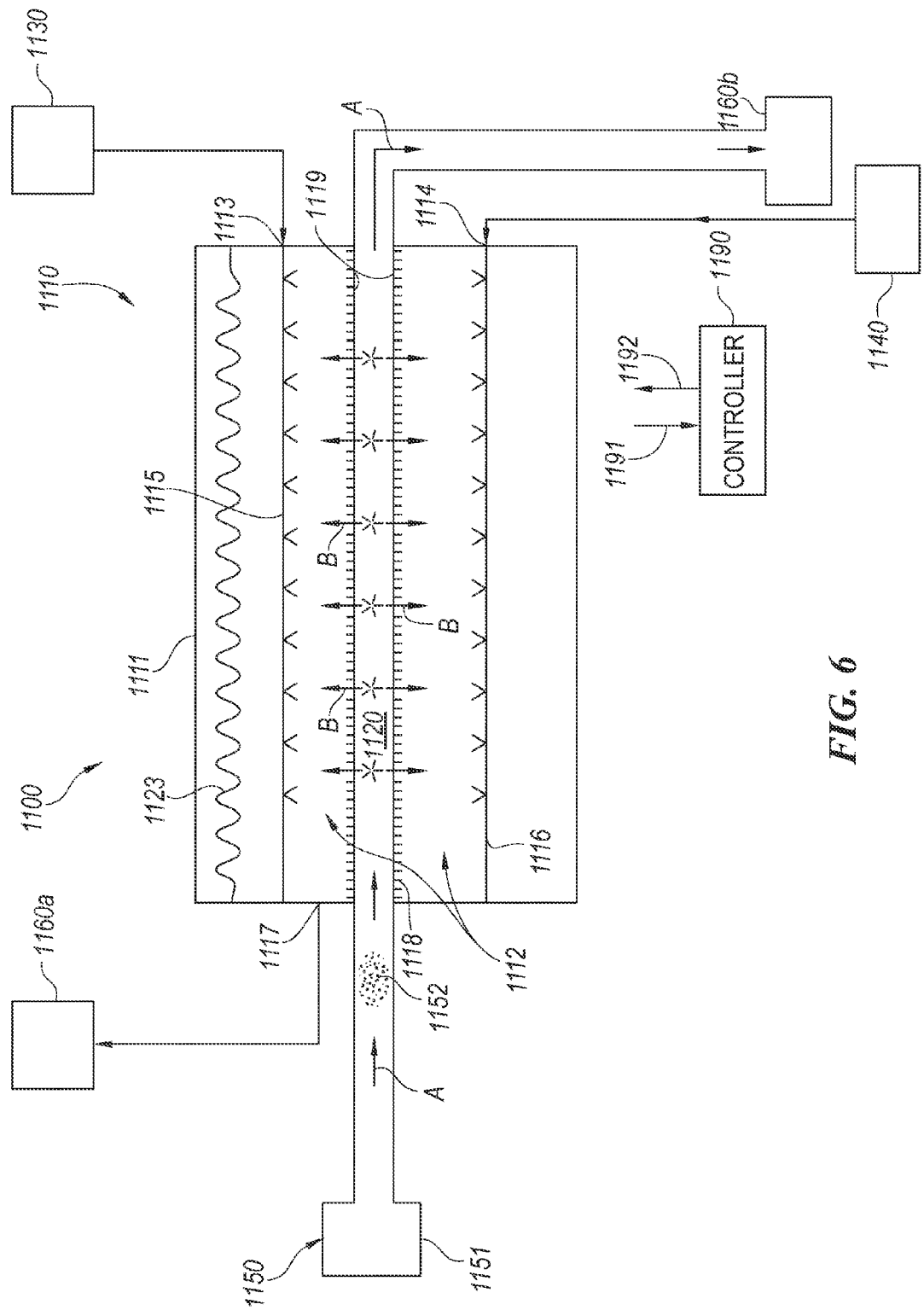
FIG. 6 is a partially schematic, partially cross-sectional illustration of a system having a reactor with transmissive surfaces in accordance with an embodiment of the disclosed technology.

In any of the forgoing embodiments, the reaction zone 1312 can house one or more steam distributors 1316 and one or more hydrogen donor distributors 1315. Each of the distributors 1315, 1316 can include pores 1324 and/or other apertures, openings or passages that allow chemical reactants to enter the reaction zone 1312. The donor distributors 1315, 1316 can include one or more spiral conduits, including, e.g., conduits arranged in a braided fashion to distribute reactants into the reaction zone uniformly in the axial, radial and circumferential directions. The reaction zone 1312 is bounded by the third conduit 1322c which can have an insulated reactor outer surface 1321 to conserve heat within the reaction zone 1312. During operation, the reaction taking place in the reaction zone 1312 can be controlled by adjusting the rate at which steam and the hydrogen donor enter the reaction zone 1312, the rate at which heat enters the reaction zone 1312 (via the combustion product passage 1318 and/or the heater 1323) and other variables, including the pressure at the reaction zone 1312. Appropriate sensors and control feedback loops carry out these processes autonomously, with optional controller intervention, as described above with reference to FIG. 6.

Still further embodiments of suitable reactors with transmissive surfaces are disclosed in pending U.S. application Ser. No. 13/026,996, filed Feb. 14, 2011, and incorporated herein by reference.

4.2 Representative Reactors with Re-Radiative Components

Figure 8:
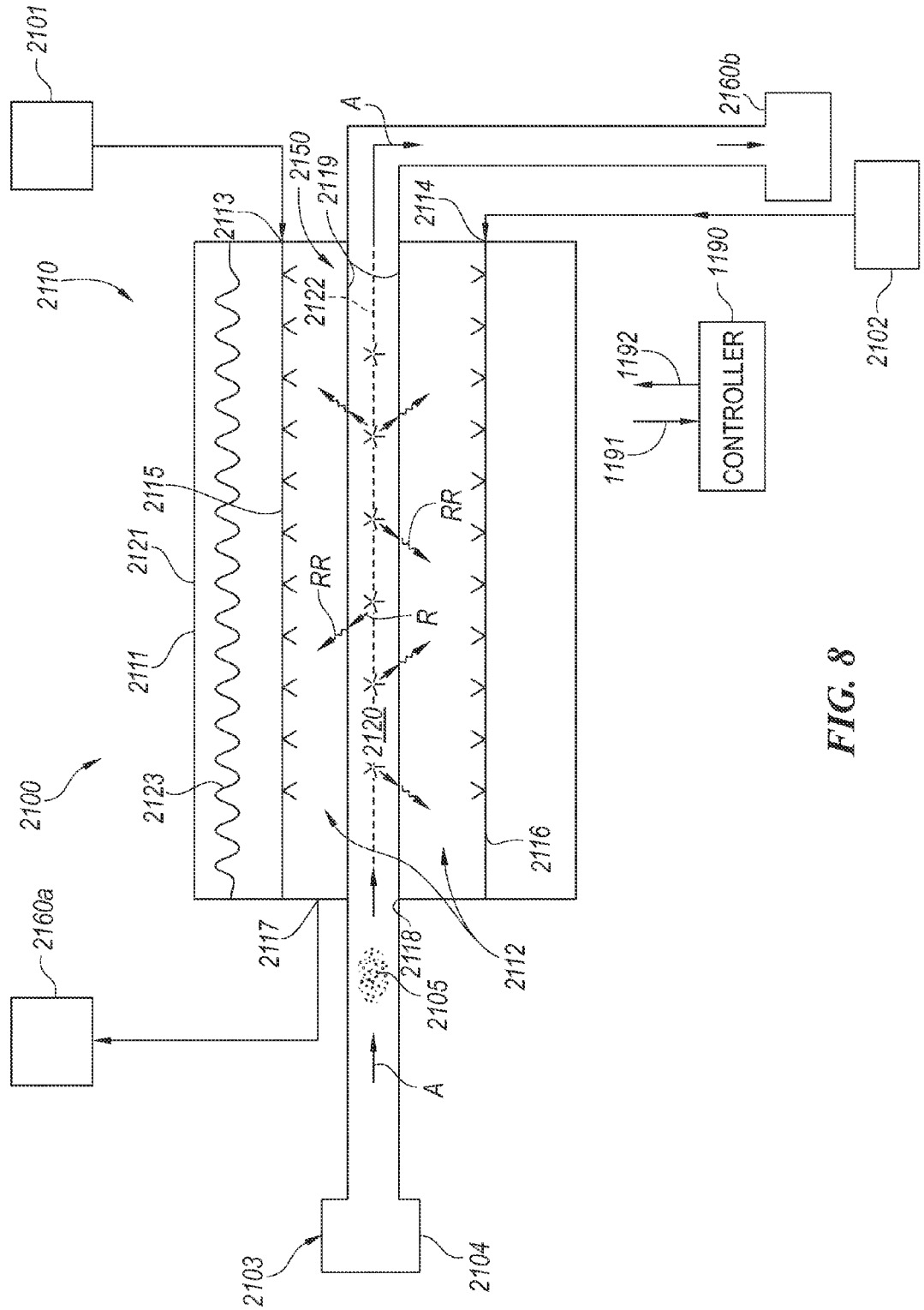
FIG. 8 is a partially schematic, partially cross-sectional illustration of a system having a reactor with a re-radiation component in accordance with an embodiment of the presently disclosed technology.

FIG. 8 is a partially schematic illustration of a system 2100 that includes a reactor 2110 having one or more selective (e.g., re-radiative) surfaces in accordance with embodiments of the disclosure. The reactor 2110 further includes a reactor vessel 2111 having an outer surface 2121 that encloses or partially encloses a reaction zone 2112. In a representative example, the reactor vessel 2111 receives a hydrogen donor provided by a donor source 2101 to a donor entry port 2113. For example, the hydrogen donor can include methane or another hydrocarbon. A donor distributor or manifold 2115 within the reactor vessel 2111 disperses or distributes the hydrogen donor into the reaction zone 2112. The reactor vessel 2111 also receives steam from a steam/water source 2102 via a steam entry port 2114. A steam distributor 2116 in the reactor vessel 2111 distributes the steam into the reaction zone 2112. The reactor vessel 2111 can still further include a heater 2123 that supplies heat to the reaction zone 2112 to facilitate endothermic reactions. Such reactions can include dissociating methane or another hydrocarbon into hydrogen or a hydrogen compound, and carbon or a carbon compound. The products of the reaction (e.g., carbon and hydrogen) exit the reactor vessel 2111 via an exit port 2117 and are collected at a reaction product collector 2160a.

The system 2100 can further include a source 2103 of radiant energy and/or additional reactants, which provides constituents to a passage 2118 within the reactor vessel 2111. For example, the radiant energy/reactant source 2103 can include a combustion chamber 2104 that provides hot combustion products 2105 to the passage 2118, as indicated by arrow A. In a particular embodiment, the passage 2118 is concentric relative to a passage centerline 2122. In other embodiments, the passage 2118 can have other geometries. A combustion products collector 2160b collects combustion products exiting the reactor vessel 2111 for recycling and/or other uses. In a particular embodiment, the combustion products 2105 can include carbon monoxide, water vapor, and other constituents.

One or more re-radiation components 2150 are positioned between the reaction zone 2112 (which can be disposed annularly around the passage 2118) and an interior region 2120 of the passage 2118. The re-radiation component 2150 can accordingly absorb incident radiation R from the passage 2118 and direct re-radiated energy RR into the reaction zone 2112. The re-radiated energy RR can have a wavelength spectrum or distribution that more closely matches, approaches, overlaps and/or corresponds to the absorption spectrum of at least one of the reactants and/or at least one of the resulting products. By delivering the radiant energy at a favorably shifted wavelength, the system 2100 can enhance the reaction taking place in the reaction zone 2112, for example, by increasing the efficiency with which energy is absorbed by the reactants, thus increasing the reaction zone temperature and/or pressure, and therefore the reaction rate, and/or the thermodynamic efficiency of the reaction. In a particular aspect of this embodiment, the combustion products 2105 and/or other constituents provided by the source 2103 can be waste products from another chemical process (e.g., an internal combustion process). Accordingly, the foregoing process can recycle or reuse energy and/or constituents that would otherwise be wasted, in addition to facilitating the reaction at the reaction zone 2112.

In at least some embodiments, the re-radiation component 2150 can be used in conjunction with, and/or integrated with, a transmissive surface 2119 that allows chemical constituents (e.g., reactants) to readily pass from the interior region 2120 of the passage 2118 to the reaction zone 2112. Further details of representative transmissive surfaces were discussed above under heading 4.1. In other embodiments, the reactor 2110 can include one or more re-radiation components 2150 without also including a transmissive surface 2119. In any of these embodiments, the radiant energy present in the combustion product 2105 may be present as an inherent result of the combustion process. In other embodiments, an operator can introduce additives into the stream of combustion products 2105 (and/or the fuel that produces the combustion products) to increase the amount of energy extracted from the stream and delivered to the reaction zone 2112 in the form of radiant energy. For example, the combustion products 2105 (and/or fuel) can be seeded with sources of sodium, potassium, and/or magnesium, which can absorb energy from the combustion products 2105 and radiate the energy outwardly into the reaction zone 2112 at desirable frequencies. These illuminant additives can be used in addition to the re-radiation component 2150.

Figure 9:
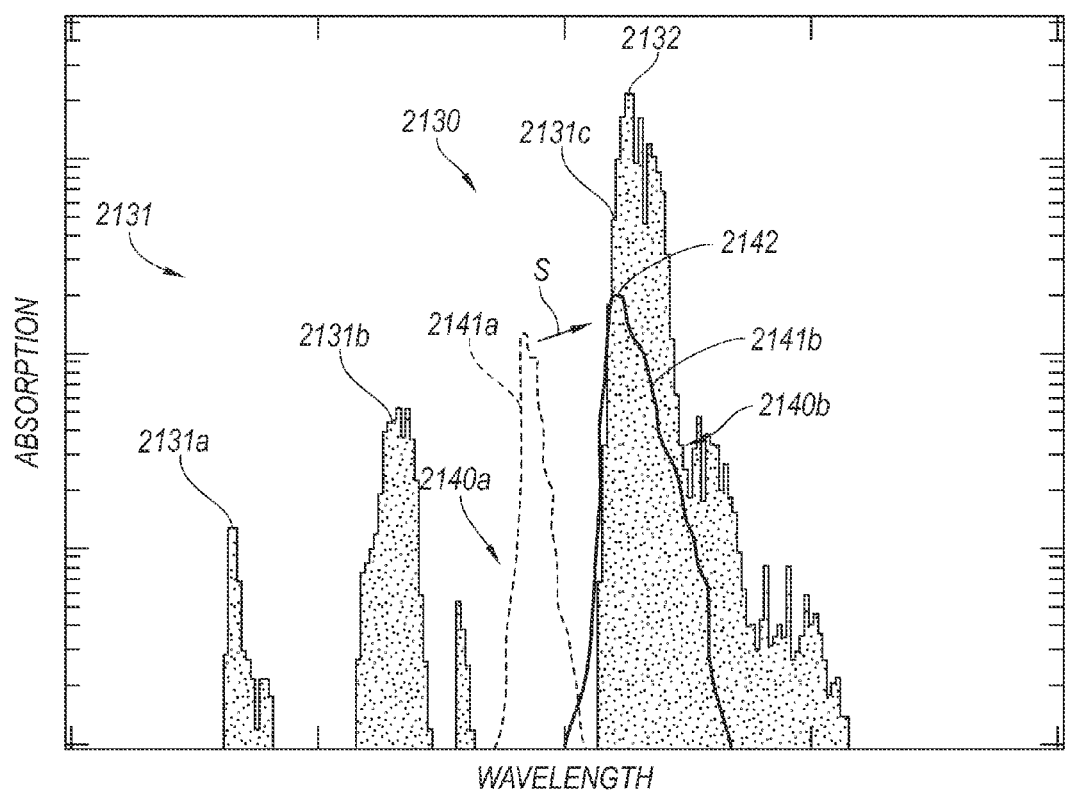
FIG. 9 illustrates absorption characteristics as a function of wavelength for a representative reactant and re-radiation material, in accordance with an embodiment of the presently disclosed technology.

FIG. 9 is a graph presenting absorption as a function of wavelength for a representative reactant (e.g., methane) and a representative re-radiation component. FIG. R2-2 illustrates a reactant absorption spectrum 2130 that includes multiple reactant peak absorption ranges 2131, three of which are highlighted in FIG. 9 as first, second and third peak absorption ranges 2131a, 2131b, 2131c. The peak absorption ranges 2131 represent wavelengths for which the reactant absorbs more energy than at other portions of the spectrum 2130. The spectrum 2130 can include a peak absorption wavelength 2132 within a particular range, e.g., the third peak absorption range 2131c.

FIG. 9 also illustrates a first radiant energy spectrum 2140a having a first peak wavelength range 2141a. For example, the first radiant energy spectrum 2140a can be representative of the emission from the combustion products 2105 described above with reference to FIG. 8. After the radiant energy has been absorbed and re-emitted by the re-radiation component 2150 described above, it can produce a second radiant energy spectrum 2140b having a second peak wavelength range 2141b, which in turn includes a re-radiation peak value 2142. In general terms, the function of the re-radiation component 2150 is to shift the spectrum of the radiant energy from the first radiant energy spectrum 2140a and peak wavelength range 2141a to the second radiant energy spectrum 2140b and peak wavelength range 2141b, as indicated by arrow S. As a result of the shift, the second peak wavelength range 2141b is closer to the third peak absorption range 2131c of the reactant than is the first peak wavelength range 2141a. For example, the second peak wavelength range 2141b can overlap with the third peak absorption range 2131c and in a particular embodiment, the re-radiation peak value 2142 can be at, or approximately at the same wavelength as the reactant peak absorption wavelength 2132. In this manner, the re-radiation component more closely aligns the spectrum of the radiant energy with the peaks at which the reactant efficiently absorbs energy. Representative structures for performing this function are described in further detail below with reference to FIG. 10.

Figure 10:
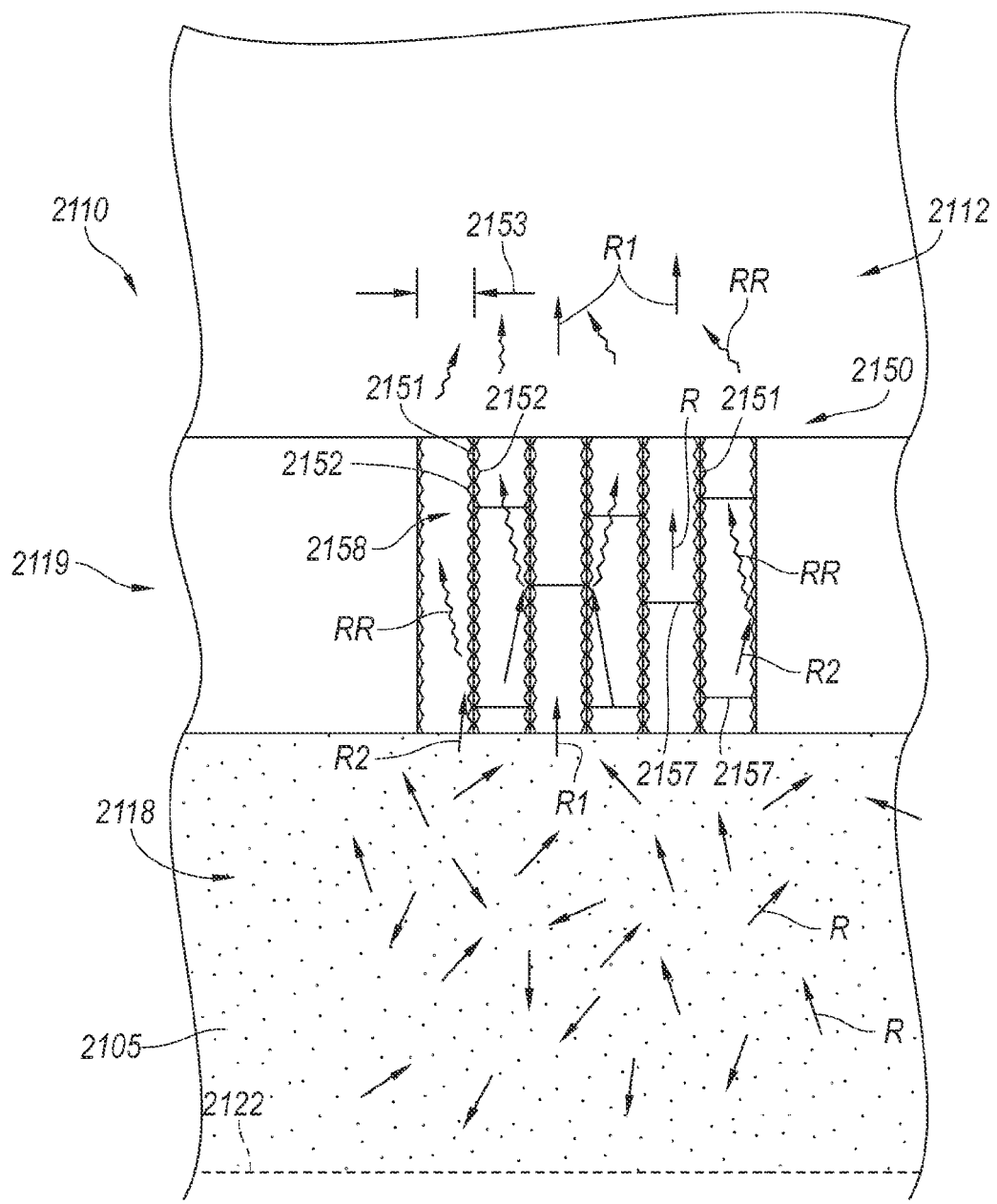
FIG. 10 is an enlarged, partially schematic illustration of a portion of the reactor shown in FIG. 9 having a re-radiation component configured in accordance with a particular embodiment of the presently disclosed technology.

FIG. 10 is a partially schematic, enlarged cross-sectional illustration of a portion of the reactor 2110 described above with reference to FIG. 8, having a re-radiation component 2150 configured in accordance with a particular embodiment of the technology. The re-radiation component 2150 is positioned between the passage 2118 (and the radiation energy R in the passage 2118), and the reaction zone 2112. The re-radiation component 2150 can include layers 2151 of material that form spaced-apart structures 2158, which in turn carry a re-radiative material 2152. For example, the layers 2151 can include graphene layers or other crystal or self-orienting layers made from suitable building block elements such as carbon, boron, nitrogen, silicon, transition metals, and/or sulfur. Carbon is a particularly suitable constituent because it is relatively inexpensive and readily available. In fact, it is a target output product of reactions that can be completed in the reaction zone 2112. Further details of suitable structures are disclosed in co-pending U.S. application Ser. No. 12/857,228 previously incorporated herein by reference. Each structure 2158 can be separated from its neighbor by a gap 2153. The gap 2153 can be maintained by spacers 2157 extending between neighboring structures 2158. In particular embodiments, the gaps 2153 between the structures 2158 can be from about 2.5 microns to about 25 microns wide. In other embodiments, the gap 2153 can have other values, depending, for example, on the wavelength of the incident radiative energy R. The spacers 2157 are positioned at spaced-apart locations both within and perpendicular to the plane of FIG. 10 so as not to block the passage of radiation and/or chemical constituents through the component 2150.

The radiative energy R can include a first portion R1 that is generally aligned parallel with the spaced-apart layered structures 2158 and accordingly passes entirely through the re-radiation component 2150 via the gaps 2153 and enters the reaction zone 2112 without contacting the re-radiative material 2152. The radiative energy R can also include a second portion R2 that impinges upon the re-radiative material 2152 and is accordingly re-radiated as a re-radiated portion RR into the reaction zone 2112. The reaction zone 2112 can accordingly include radiation having different energy spectra and/or different peak wavelength ranges, depending upon whether the incident radiation R impinged upon the re-radiative material 2152 or not. This combination of energies in the reaction zone 2112 can be beneficial for at least some reactions. For example, the shorter wavelength, higher frequency (higher energy) portion of the radiative energy can facilitate the basic reaction taking place in the reaction zone 2112, e.g., disassociating methane in the presence of steam to form carbon monoxide and hydrogen. The longer wavelength, lower frequency (lower energy) portion can prevent the reaction products from adhering to surfaces of the reactor 2110, and/or can separate such products from the reactor surfaces. In particular embodiments, the radiative energy can be absorbed by methane in the reaction zone 2112, and in other embodiments, the radiative energy can be absorbed by other reactants, for example, the steam in the reaction zone 2112, or the products. In at least some cases, it is preferable to absorb the radiative energy with the steam. In this manner, the steam receives sufficient energy to be hot enough to complete the endothermic reaction within the reaction zone 2112, without unnecessarily heating the carbon atoms, which may potentially create particulates or tar if they are not quickly oxygenated after dissociation.

The re-radiative material 2152 can include a variety of suitable constituents, including iron carbide, tungsten carbide, titanium carbide, boron carbide, and/or boron nitride. These materials, as well as the materials forming the spaced-apart structures 2158, can be selected on the basis of several properties including corrosion resistance and/or compressive loading. For example, loading a carbon structure with any of the foregoing carbides or nitrides can produce a compressive structure. An advantage of a compressive structure is that it is less subject to corrosion than is a structure that is under tensile forces. In addition, the inherent corrosion resistance of the constituents of the structure (e.g., the foregoing carbides and nitrides) can be enhanced because, under compression, the structure is less permeable to corrosive agents, including steam which may well be present as a reactant in the reaction zone 2112 and as a constituent of the combustion products 2105 in the passage 2118. The foregoing constituents can be used alone or in combination with phosphorus, calcium fluoride and/or another phosphorescent material so that the energy re-radiated by the re-radiative material 2152 may be delayed. This feature can smooth out at least some irregularities or intermittencies with which the radiant energy is supplied to the reaction zone 2112.

Another suitable re-radiative material 2152 includes spinel or another composite of magnesium and/or aluminum oxides. Spinel can provide the compressive stresses described above and can shift absorbed radiation to the infrared so as to facilitate heating the reaction zone 2112. For example, sodium or potassium can emit visible radiation (e.g., red/orange/yellow radiation) that can be shifted by spinel or another alumina-bearing material to the IR band. If both magnesium and aluminum oxides, including compositions with colorant additives such as magnesium, aluminum, titanium, chromium, nickel, copper and/or vanadium, are present in the re-radiative material 2152, the re-radiative material 2152 can emit radiation having multiple peaks, which can in turn allow multiple constituents within the reaction zone 2112 to absorb the radiative energy.

The particular structure of the re-radiation component 2150 shown in FIG. 10 includes gaps 2153 that can allow not only radiation to pass through, but can also allow constituents to pass through. Accordingly, the re-radiation component 2150 can also form the transmissive surface 2119, which, as described above with reference to FIG. 8, can further facilitate the reaction in the reaction zone 2112 by admitting reactants.

Still further embodiments of suitable reactors with re-radiative components are disclosed in pending U.S. application Ser. No. 13/027,015, filed Feb. 14, 2011, and incorporated herein by reference.

4.3 Representative Reactors with Heat Pipes and Heat Pumps

Figure 11:
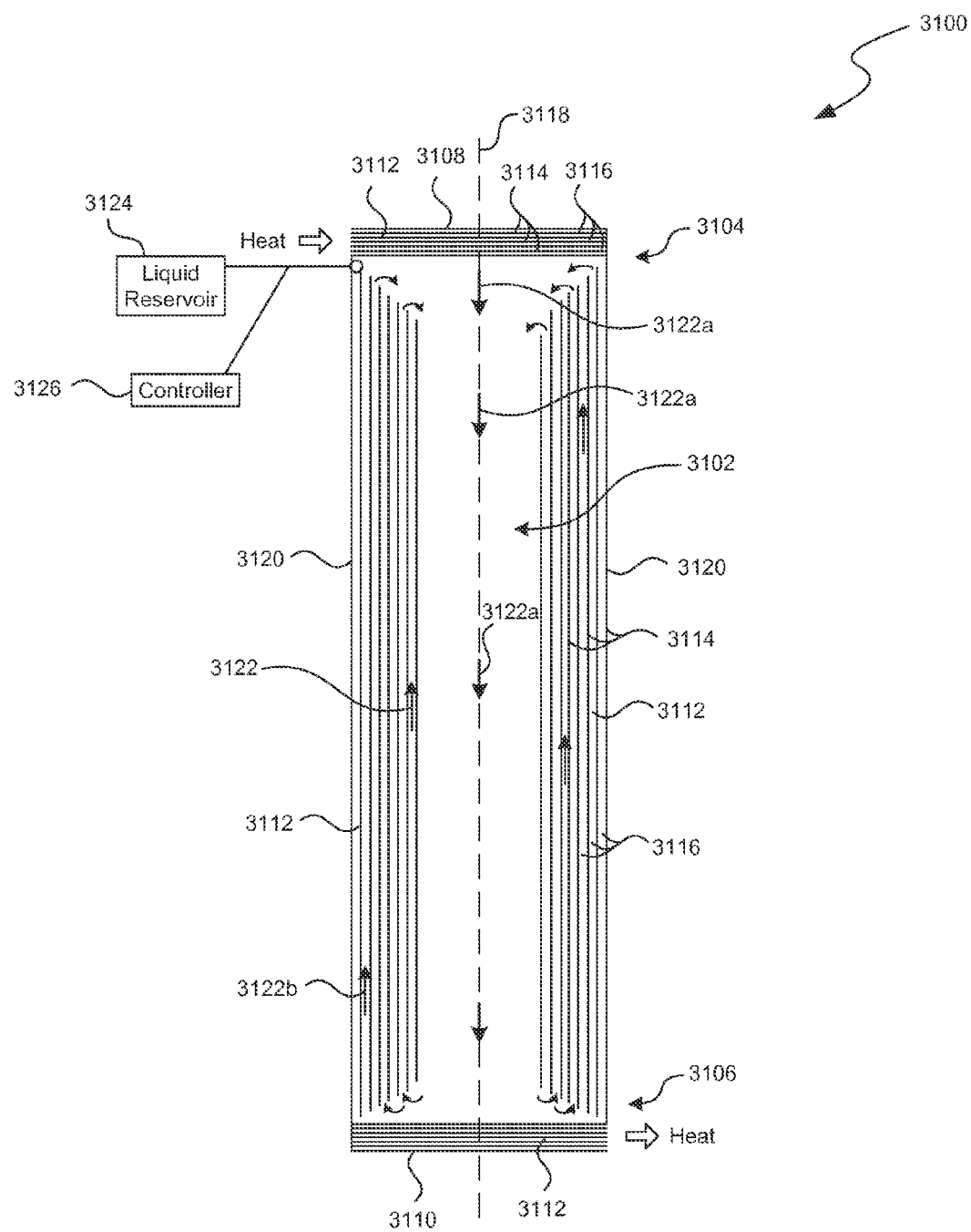
FIG. 11 is a schematic cross-sectional view of a thermal transfer device configured in accordance with an embodiment of the present technology.

FIG. 11 is a schematic cross-sectional view of a thermal transfer device 3100 ("device 3100") configured in accordance with an embodiment of the present technology. As shown in FIG. 11, the device 3100 can include a conduit 3102 that has an input portion 3104, an output portion 3106 opposite the input portion 3104, and a sidewall 3120 between the input and output portions 3104 and 3106. The device 3100 can further include a first end cap 3108 at the input portion 3104 and a second end cap 3110 at the output portion 3106. The device 3100 can enclose a working fluid 3122 (illustrated by arrows) that changes between a vapor phase 3122a and a liquid phase 3122b during a vaporization-condensation cycle.

In selected embodiments, the device 3100 can also include one or more architectural constructs 3112. Architectural constructs 3112 are synthetic matrix characterizations of crystals that are primarily comprised of graphene, graphite, boron nitride, and/or another suitable crystal. The configuration and the treatment of these crystals heavily influence the properties that the architectural construct 3112 will exhibit when it experiences certain conditions. For example, as explained in further detail below, the device 3100 can utilize architectural constructs 3112 for their thermal properties, capillary properties, sorbtive properties, catalytic properties, and electromagnetic, optical, and acoustic properties. As shown in FIG. 11, the architectural construct 3112 can be arranged as a plurality of substantially parallel layers 3114 spaced apart from one another by a gap 3116. In various embodiments, the layers 3114 can be as thin as one atom. In other embodiments, the thickness of the individual layers 3114 can be greater and/or less than one atom and the width of the gaps 3116 between the layers 3114 can vary. Methods of fabricating and configuring architectural constructs, such as the architectural constructs 3112 shown in FIG. 11, are described in U.S. patent application Ser. No. 12/857,228 previously incorporated herein by reference.

As shown in FIG. 11, the first end cap 3108 can be installed proximate to a heat source (not shown) such that the first end cap 3108 serves as a hot interface that vaporizes the working fluid 3122. Accordingly, the first end cap 3108 can include a material with a high thermal conductivity and/or transmissivity to absorb or deliver heat from the heat source. In the embodiment illustrated in FIG. 11, for example, the first end cap 3108 includes the architectural construct 3112 made from a thermally conductive crystal (e.g., graphene). The architectural construct 3112 can be arranged to increase its thermal conductively by configuring the layers 3114 to have a high concentration of thermally conductive pathways (e.g., formed by the layers 3114) substantially parallel to the influx of heat. For example, in the illustrated embodiment, the layers 3114 generally align with the incoming heat flow such that heat enters the architectural construct 3112 between the layers 3114. This configuration exposes the greatest surface area of the layers 3114 to the heat and thereby increases the heat absorbed by the architectural construct 3112. Advantageously, despite having a much lower density than metal, the architectural construct 3112 can conductively and/or radiatively transfer a greater amount of heat per unit area than solid silver, raw graphite, copper, or aluminum.

As further shown in FIG. 11, the second end cap 3110 can expel heat from the device 3100 to a heat sink (not shown) such that the second end cap 3110 serves as a cold interface that condenses the working fluid 3122. The second end cap 3110, like the first end cap 3108, can include a material with a high thermal conductivity (e.g., copper, aluminum) and/or transmissivity to absorb and/or transmit latent heat from the working fluid 3122. Accordingly, like the first end cap 3108, the second end cap 3110 can include the architectural construct 3112. However, rather than bringing heat into the device 3100 like the first end cap 3108, the second end cap 3110 can convey latent heat out of the device 3100. In various embodiments, the architectural constructs 3112 of the first and second end caps 3108 and 3110 can be made from the similar materials and/or arranged to have substantially similar thermal conductivities. In other embodiments, the architectural constructs 3112 can include different materials, can be arranged in differing directions, and/or otherwise configured to provide differing thermal conveyance capabilities including desired conductivities and transmissivities. In further embodiments, neither the first end cap 3108 nor the second end cap 3110 includes the architectural construct 3112.

In selected embodiments, the first end cap 3108 and/or the second end cap 3110 can include portions with varying thermal conductivities. For example, a portion of the first end cap 3108 proximate to the conduit 3102 can include a highly thermally conductive material (e.g., the architectural construct 3112 configured to promote thermal conductivity, copper, etc.) such that it absorbs heat from the heat source and vaporizes the working fluid 3122. Another portion of the first end cap 3108 spaced apart from the conduit 3102 can include a less thermally conductive material to insulate the high conductivity portion. In certain embodiments, for example, the insulative portion can include ceramic fibers, sealed dead air space, and/or other materials or structures with high radiant absorptivities and/or low thermal conductivities. In other embodiments, the insulative portion of the first end cap 3108 can include the architectural construct 3112 arranged to include a low concentration of thermally conductive pathways (e.g., the layers 3114 are spaced apart by large gaps 3116) such that it has a low availability for conductively transferring heat.

In other embodiments, the configurations of the architectural constructs 3112 may vary from those shown in FIG. 11 based on the dimensions of the device 3100, the temperature differential between the heat source and the heat sink, the desired heat transfer, the working fluid 3122, and/or other suitable thermal transfer characteristics. For example, architectural constructs 3112 having smaller surface areas may be suited for microscopic applications of the device 3100 and/or high temperature differentials, whereas architectural constructs 3112 having higher surface areas may be better suited for macroscopic applications of the device 3100 and/or higher rates of heat transfer. The thermal conductivities of the architectural constructs 3112 can also be altered by coating the layers 3114 with dark colored coatings to increase heat absorption and with light colored coatings to reflect heat away and thereby decrease heat absorption.

Referring still to FIG. 11, the device 3100 can return the liquid phase 3122b of the working fluid 3122 to the input portion 3104 by capillary action. The sidewall 3120 of the conduit 3102 can thus include a wick structure that exerts a capillary pressure on the liquid phase 3122b to drive it toward a desired location (e.g., the input portion 3104). For example, the sidewall 3120 can include cellulose, ceramic wicking materials, sintered or glued metal powder, nanofibers, and/or other suitable wick structures or materials that provide capillary action.

In the embodiment shown in FIG. 11, the architectural construct 3112 is aligned with the longitudinal axis 3118 of the conduit 3102 and configured to exert the necessary capillary pressure to direct the liquid phase 3122b of the working fluid 3122 to the input portion 3104. The composition, dopants, spacing, and/or thicknesses of the layers 3114 can be selected based on the surface tension required to provide capillary action for the working fluid 3122. Advantageously, the architectural construct 3112 can apply sufficient capillary pressure on the liquid phase 3122b to drive the working fluid 3122 short and long distances (e.g., millimeters to kilometers). Additionally, in selected embodiments, the surface tension of the layers 3114 can be manipulated such that the architectural construct 3112 rejects a preselected fluid. For example, the architectural construct 3112 can be configured to have a surface tension that rejects any liquid other than the liquid phase 3122b of the working fluid 3122. In such an embodiment, the architectural construct 3112 can function as a filter that prevents any fluid other than the working fluid 3122 (e.g., fluids tainted by impurities that diffused into the conduit 3102) from interfering with the vaporization-condensation cycle.

In other embodiments, the selective capillary action of the architectural construct 3112 separates substances at far lower temperatures than conventional distillation technologies. The faster separation of substances by the architectural construct 3112 can reduce or eliminates substance degradation caused if the substance reaches higher temperatures within the device 3100. For example, a potentially harmful substance can be removed from the working fluid 3122 by the selective capillary action of the architectural construct 3112 before the working fluid 3122 reaches the higher temperatures proximate to the input portion 3104.

The conduit 3102 and the first and second end caps 3108 and 3110 can be sealed together using suitable fasteners able to withstand the temperature differentials of the device 3100. In other embodiments, the device 3100 is formed integrally. For example, the device 3100 can be molded using one or more materials. A vacuum can be used to remove any air within the conduit 3102, and then the conduit 3102 can be filled with a small volume of the working fluid 3122 chosen to match the operating temperatures.

In operation, the device 3100 utilizes a vaporization-condensation cycle of the working fluid 3122 to transfer heat. More specifically, the first end cap 3108 can absorb heat from the heat source, and the working fluid 3122 can in turn absorb the heat from the first end cap 3108 to produce the vapor phase 3122a. The pressure differential caused by the phase change of the working fluid 3122 can drive the vapor phase 3122a of the working fluid 3122 to fill the space available and thus deliver the working fluid 3122 through the conduit 3102 to the output portion 3104. At the output portion 3104, the second end cap 3110 can absorb heat from the working fluid 3122 to change the working fluid 3122 to the liquid phase 3122b. The latent heat from the condensation of the working fluid 3122 can be transferred out of the device 3100 via the second end cap 3110. In general, the heat influx to the first end cap 3108 substantially equals the heat removed by the second end cap 3110. As further shown in FIG. 11, capillary action provided by the architectural construct 3112 or other wick structure can return the liquid phase 3122b of the working fluid 3122 to the input portion 3104. In selected embodiments, the termini of the layers 3114 can be staggered or angled toward the conduit 3102 to facilitate entry of the liquid phase 3122b between the layers 3114 and/or to facilitate conversion of the liquid phase 3122b to the vapor phase 3122b at the input portion 3104. At the input portion 3104, the working fluid 3122 can again vaporize and continue to circulate through the conduit 3102 by means of the vaporization-condensation cycle.

The device 3100 can also operate the vaporization-condensation cycle described above in the reverse direction. For example, when the heat source and heat sink are reversed, the first end cap 3108 can serve as the cold interface and the second end cap 3110 can serve as the hot interface. Accordingly, the input and output portions 3104 and 3106 are inverted such that the working fluid 3122 vaporizes proximate to the second end cap 3110, condenses proximate to the first end cap 3108, and returns to the second end cap 3110 using the capillary action provided by the sidewall 3120. The reversibility of the device 3100 allows the device 3100 to be installed irrespective of the positions of the heat source and heat sink. Additionally, the device 3100 can accommodate environments in which the locations of the heat source and the heat sink may reverse. For example, as described further below, the device 3100 can operate in one direction during the summer to utilize solar energy and the device 3100 can reverse direction during the winter to utilize heat stored during the previous summer.

Embodiments of the device 3100 including the architectural construct 3112 at the first end cap 3108 and/or second end cap 3110 have higher thermal conductivity per unit area than conventional conductors. This increased thermal conductivity can increase process rate and the temperature differential between the first and second end caps 3108 and 3110 to produce greater and more efficient heat transfer. Additionally, embodiments including the architectural construct 3112 at the first and/or second end caps 3108 and 3110 require less surface area to absorb the heat necessary to effectuate the vaporization-condensation cycle. Thus, the device 3100 can be more compact than a conventional heat pipe that transfers an equivalent amount of heat and provide considerable cost reduction.

Referring still to FIG. 11, in various embodiments, the device 3100 can further include a liquid reservoir 3124 in fluid communication with the conduit 3102 such that the liquid reservoir 3124 can collect and store at least a portion of the working fluid 3122. As shown in FIG. 11, the liquid reservoir 3124 can be coupled to the input portion 3104 of the conduit 3102 via a pipe or other suitable tubular shaped structure. The liquid phase 3122b can thus flow from the sidewall 3102 (e.g., the architectural construct 3112, wick structure, etc.) into the liquid reservoir 3124. In other embodiments, the liquid reservoir 3124 is in fluid communication with another portion of the conduit 3102 (e.g., the output portion 3106) such that the liquid reservoir 3124 collects the working fluid 3122 in the vapor phase 3122a or in mixed phases.

The liquid reservoir 3124 allows the device 3100 to operate in at least two modes: a heat accumulation mode and a heat transfer mode. During the heat accumulation mode, the vaporization-condensation cycle of the working fluid 3122 can be slowed or halted by funneling the working fluid 3122 from the conduit 3102 to the liquid reservoir 3124. The first end cap 3108 can then function as a thermal accumulator that absorbs heat without the vaporization-condensation cycle dissipating the accumulated heat. After the first end cap 3108 accumulates a desired amount of heat and/or the heat source (e.g., the sun) no longer supplies heat, the device 3100 can change to the heat transfer mode by funneling the working fluid 3122 into the conduit 3102. The heat stored in first end cap 3108 can vaporize the incoming working fluid 3122 and the pressure differential can drive the vapor phase 3122a toward the output portion 3106 of the conduit 3102 to restart the vaporization-condensation cycle described above. In certain embodiments, the restart of the vaporization-condensation cycle can be monitored to analyze characteristics (e.g., composition, vapor pressure, latent heat, efficiency) of the working fluid 3122.

As shown in FIG. 11, a controller 3126 can be operably coupled to the liquid reservoir 3124 to modulate the rate at which the working fluid 3122 enters the conduit 3102 and/or adjust the volume of the working fluid 3122 flowing into or out of the conduit 3102. The controller 3126 can thereby change the pressure within the conduit 3102 such that the device 3100 can operate at varying temperature differentials between the heat source and sink. Thus, the device 3100 can provide a constant heat flux despite a degrading heat source (e.g., first end cap 3108) or intermittent vaporization-condensation cycles.

Figure 12:
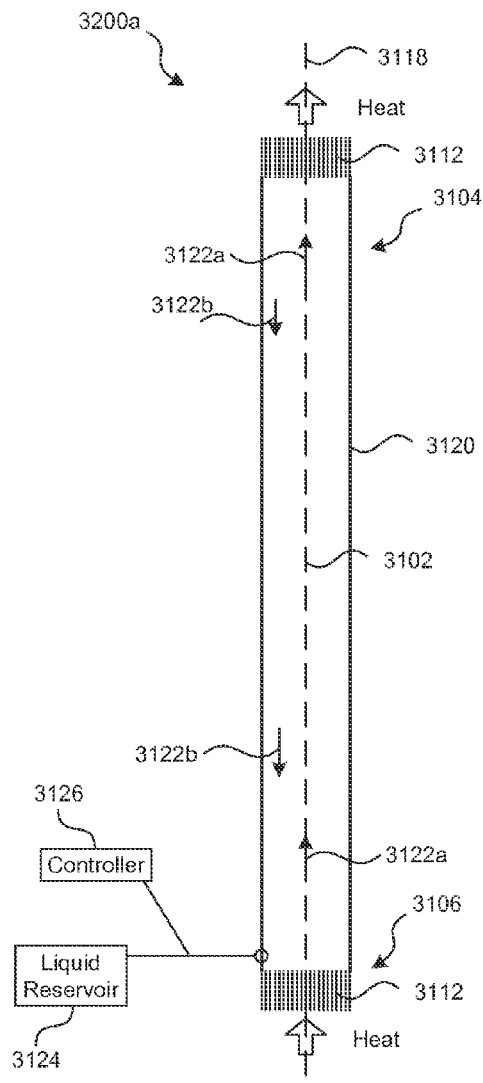
FIGS. 12 and 13 are schematic cross-sectional views of thermal transfer devices configured in accordance with other embodiments of the present technology.
Figure 13:
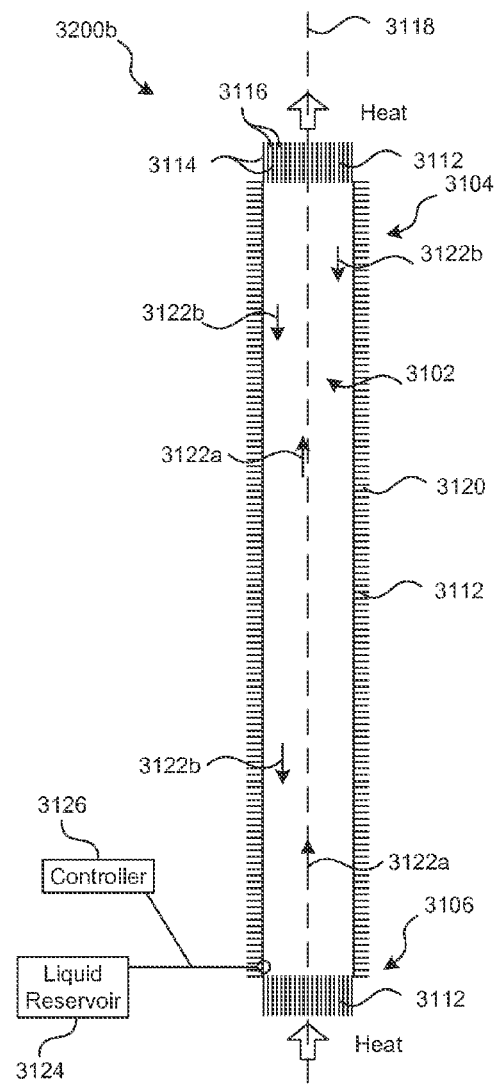

FIGS. 12 and 13 are schematic cross-sectional views of thermal transfer devices 3200a, 3200b ("devices 3200") in accordance with other embodiments of the present technology. Several features of the devices 3200 are generally similar to the features of the device 3100 shown in FIG. 11. For example, each device 3200 can include the conduit 3102, the sidewall 3120, and the first and second end caps 3108 and 3110. The device 3200 also transfers heat from a heat source to a heat sink utilizing a vaporization-condensation cycle of the working fluid 3122 generally similar to that described with reference to FIG. 11. Additionally, as shown in FIGS. 12 and 13, the device 3200 can further include the liquid reservoir 3124 and the controller 3126 such that the device 3200 can operate in the heat accumulation mode and the heat transfer mode.

The devices 3200 shown in FIGS. 12 and 13 can utilize gravity, rather than the capillary action described in FIG. 11, to return the liquid phase 3122b of the working fluid 3122 to the input portion 3104. Thus, as shown in FIGS. 12 and 13, the heat inflow is below the heat output such that gravity can drive the liquid phase 3122b down the sidewall 3120 to the input portion 3104. Thus, as shown in FIG. R3-2A, the sidewall 3120 need only include an impermeable membrane 3228, rather than a wick structure necessary for capillary action, to seal the working fluid 3122 within the conduit 3102. The impermeable membrane 3228 can be made from a polymer such as polyethylene, a metal or metal alloy such as copper and stainless steel, and/or other suitable impermeable materials. In other embodiments, the devices 3200 can utilize other sources of acceleration (e.g., centrifugal force, capillary action) to return the liquid phase 3122b to the input portion 3104 such that the positions of the input and output portions 3104 and 3106 are not gravitationally dependent.

As shown in FIG. 13, in other embodiments, the sidewall 3120 can further include the architectural construct 3112. For example, the architectural construct 3112 can be arranged such that the layers 3114 are oriented orthogonal to the longitudinal axis 3118 of the conduit 3102 to form thermally conductive passageways that transfer heat away from the conduit 3102. Thus, as the liquid phase 3122b flows along the sidewall 3120, the architectural construct 3112 can draw heat from the liquid phase 3122b, along the layers 3114, and away from the sidewall 3120 of the device 3200. This can increase the temperature differential between the input and output portions 3104 and 3106 to increase the rate of heat transfer and/or facilitate the vaporization-condensation cycle when the temperature gradient would otherwise be insufficient. In other embodiments, the layers 3114 can be oriented at a different angle with respect to the longitudinal axis 3118 to transfer heat in a different direction. In certain embodiments, the architectural construct 3112 can be positioned radially outward of the impermeable membrane 3228. In other embodiments, the impermeable membrane 3228 can be radially outward of architectural construct 3112 or the architectural construct 3112 itself can provide a sufficiently impervious wall to seal the working fluid 3122 within the conduit 3102.

The first and second end caps 3108 and 3110 shown in FIGS. 12 and 13 can also include the architectural construct 3112. As shown in FIGS. 12 and 13, the layers 3114 of the architectural constructs 3112 are generally aligned with the direction heat input and heat output to provide thermally conductive passageways that efficiently transfer heat. Additionally, the architectural constructs 3112 of the first and/or second end caps 3108 and 3110 can be configured to apply a capillary pressure for a particular substance entering or exiting the conduit. For example, the composition, spacing, dopants, and/or thicknesses of the layers 3114 of the architectural constructs 3112 can be modulated to selectively draw a particular substance between the layers 3114. In selected embodiments, the architectural construct 3112 can include a first zone of layers 3114 that are configured for a first substance and a second zone of layers 3114 that are configured for a second substance to selectively remove and/or add two or more desired substances from the conduit 3102.

In further embodiments, the second end cap 3110 can utilize the sorbtive properties of the architectural constructs 3112 to selectively load a desired constituent of the working fluid 3122 between the layers 3114. The construction of the architectural construct 3112 can be manipulated to obtain the requisite surface tension to load almost any element or soluble. For example, the layers 3114 can be preloaded with predetermined dopants or materials to adjust the surface tension of adsorption along these surfaces. In certain embodiments, the layers 3114 can be preloaded with $CO_2$ such that the architectural construct 3112 can selectively mine $CO_2$ from the working fluid 3122 as heat releases through the second end cap 3110. In other embodiments, the layers 3114 can be spaced apart from one another by a predetermined distance, include a certain coating, and/or otherwise be arranged to selectively load the desired constituent. In some embodiments, the desired constituent adsorbs onto the surfaces of individual layers 3114, while in other embodiments the desired constituent absorbs into zones between the layers 3114. In further embodiments, substances can be purposefully fed into the conduit 3102 from the input portion 3104 (e.g., through the first end cap 3108) such that the added substance can combine or react with the working fluid 3122 to produce the desired constituent. Thus, the architectural construct 3112 at the second end cap 3110 can facilitate selective mining of constituents. Additionally, the architectural construct 3112 can remove impurities and/or other undesirable solubles that may have entered the conduit 3102 and potentially interfere with the efficiency of the device 3200.

Similarly, in selected embodiments, the architectural construct 3112 at the first end cap 3110 can also selectively load desired compounds and/or elements to prevent them from ever entering the conduit 3102. For example, the architectural construct 3112 can filter out paraffins that can impede or otherwise interfere with the heat transfer of the device 3200. In other embodiments, the devices 3200 can include other filters that may be used to prevent certain materials from entering the conduit 3102.

Moreover, similar to selective loading of compounds and elements, the architectural construct 3112 at the first and second end caps 3108 and 3110 may also be configured to absorb radiant energy of a desired wavelength. For example, the layers 3114 can have a certain thickness, composition, spacing to absorb a particular wavelength of radiant energy. In selected embodiments, the architectural construct 3112 absorbs radiant energy of a first wavelength and converts it into radiant energy of a second wavelength, retransmitting at least some of the absorbed energy. For example, the layers 3114 may be configured to absorb ultraviolet radiation and convert the ultraviolet radiation into infrared radiation.

Additionally, the layers 3114 can also catalyze a reaction by transferring heat to a zone where the reaction is to occur. In other implementations, the layers 3114 catalyze a reaction by transferring heat away from a zone where a reaction is to occur. For example, heat may be conductively transferred into the layers 3114 (e.g., as discussed in U.S. patent application Ser. No. 12/857,515, filed Aug. 16, 2010, entitled "APPARATUSES AND METHODS FOR STORING AND/OR FILTERING A SUBSTANCE" which is incorporated by reference herein in its entirety) to supply heat to an endothermic reaction within a support tube of the layers 3114. In some implementations, the layers 3114 catalyze a reaction by removing a product of the reaction from the zone where the reaction is to occur. For example, the layers 3114 may absorb alcohol from a biochemical reaction within a central support tube in which alcohol is a byproduct, thereby expelling the alcohol on outer edges of the layers 3114, and prolonging the life of a microbe involved in the biochemical reaction.

FIG. 12 is schematic cross-sectional view of a thermal transfer device 3300 ("device 3300") operating in a first direction in accordance with a further embodiment of the present technology, and FIG. 13 is a schematic cross-sectional view of the device 3300 of FIG. 12 operating in a second direction opposite the first direction. Several features of the device 3300 are generally similar to the features of the devices 3100 and 3200 shown in FIGS. 11, 12 and 13. For example, the device 3300 can include the conduit 3102, the first and second end caps 3108 and 3110, and the architectural construct 3112. As shown in FIGS. 12 and 13, the sidewall 3120 of the device 3300 can include two architectural constructs 3112: a first architectural construct 3112a having layers 3114 oriented parallel to the longitudinal axis 3118 of the conduit 3102 and a second architectural construct 3112b radially inward from the first architectural construct 3112a and having layers 3114 oriented perpendicular to the longitudinal axis 3118. The layers 3114 of the first architectural construct 3112a can perform a capillary action, and the layers 3114 of the second architectural construct 3112b can form thermally conductive passageways that transfer heat away from the side of the conduit 3102 and thereby increase the temperature differential between the input and output portions 3104 and 3106.

Figure 14A:
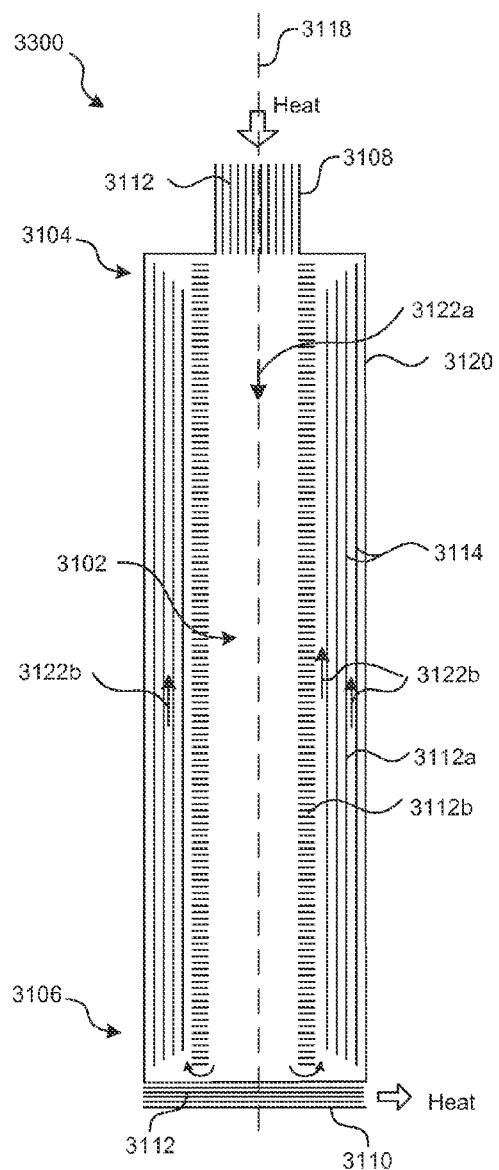
FIG. 14A is a schematic cross-sectional view of a thermal transfer device operating in a first direction in accordance with a further embodiment of the present technology.

Similar to the device 3100 shown in FIG. 11, the device 3300 can also operate when the direction of heat flow changes and the input and output portions 3104 and 3106 are inverted. As shown in FIG. 14A, for example, the device 3300 can absorb heat at the first end cap 3108 to vaporize the working fluid 3122 at the input portion 3104, transfer the heat via the vapor phase 3122a of the working fluid 3122 through the conduit 3102, and expel heat from the second end cap 3110 to condense the working fluid 3122 at the output portion 3106.

Figure 14B:
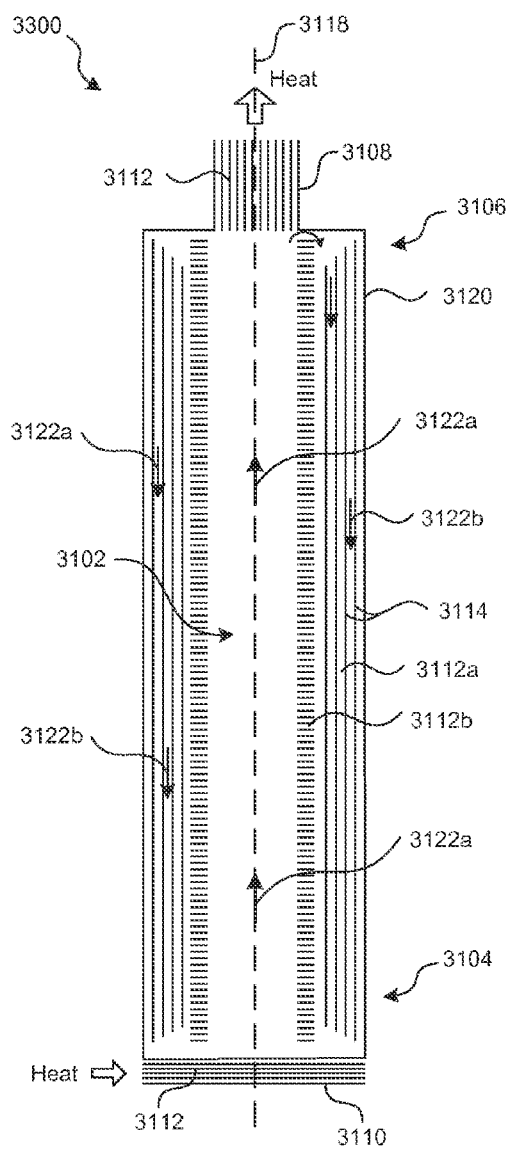
FIG. 14B is a schematic cross-sectional view of the thermal transfer device of FIG. 14A operating in a second direction opposite the first direction.

As further shown in FIG. 14A, the liquid phase 3122b of the working fluid 3122 can move between the layers 3114 of the first architectural construct 3112b by capillary action as described above with reference to FIG. 11. In other embodiments, the sidewall 3120 can include a different capillary structure (e.g., cellulose) that can drive the liquid phase 3122b from the output portion 3106 to the input portion 3104. As shown in FIG. 14B, the conditions can be reversed such that heat enters the device 3300 proximate to the second end cap 3110 and exits the device 3300 proximate to the first end cap 3108. Advantageously, as discussed above, the dual-direction vapor-condensation cycle of the working fluid 3122 accommodates environments in which the locations of the heat source and the heat sink reverse.

Figure 15:
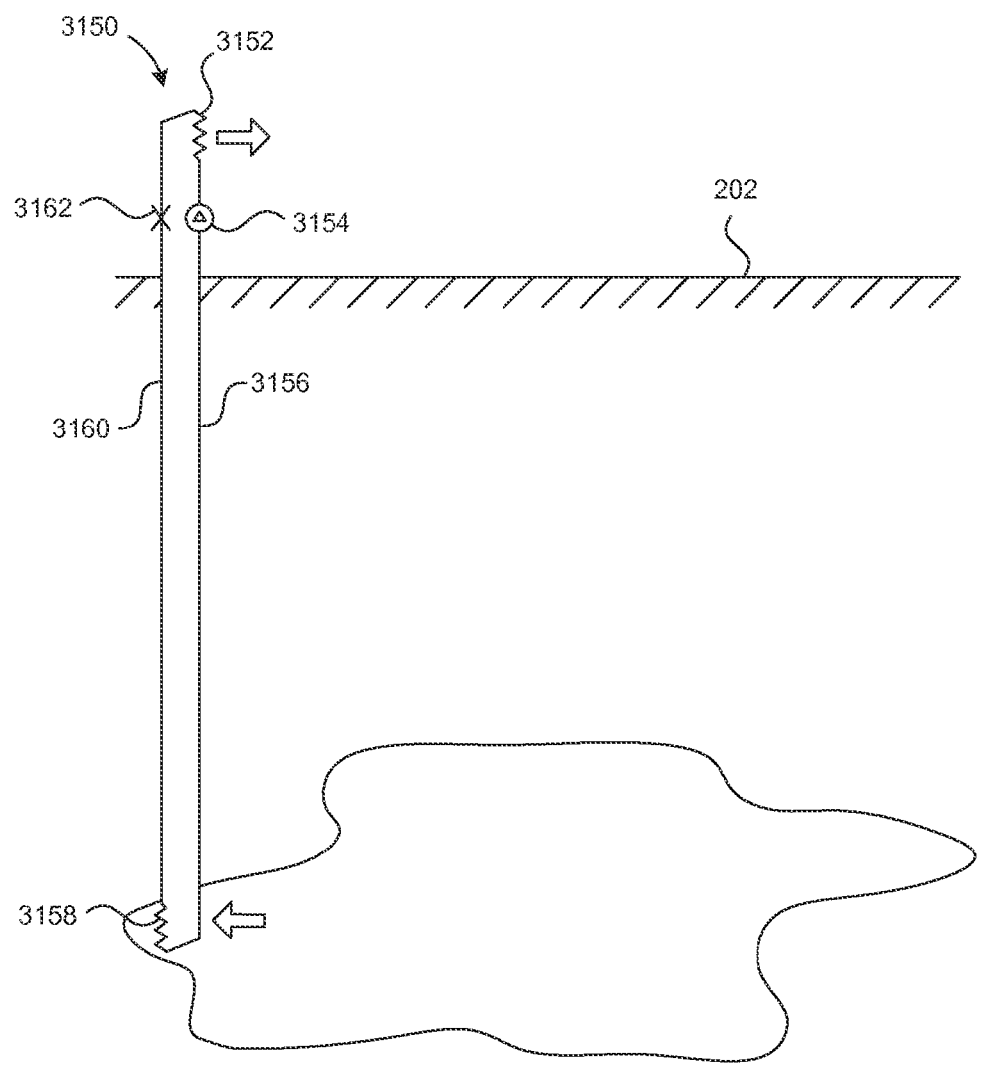
FIG. 15 is a partially schematic illustration of a heat pump suitable for transferring heat in accordance with an embodiment of the present technology.

In at least some embodiments, a heat pump can be used to transfer heat, in addition to or in lieu of a heat pipe, and the transferred heat can be used to enhance the efficiency and/or performance of a reactor to which the heat pump is coupled. In particular embodiments, the heat is extracted from a permafrost, geothermal, ocean and/or other source. FIG. 15 is a partially schematic illustration of a reversible heat pump 3150 positioned to receive heat from a source 3200 (e.g., a geothermal source), as indicated by arrow H1, and deliver the heat at a higher temperature than that of the source, as indicated by arrow H2. The heat pump 3150 transfers heat via a working fluid that can operate in a closed loop refrigeration cycle. Accordingly, the heat pump 3150 can include a compressor 3154, an expansion valve 3162, supply and return conduits 3156, 3160, and first and second heat exchangers 3152, 3158. In operation, the working fluid receives heat from the source 3200 via the second heat exchanger 3158. The working fluid passes through the supply conduit 3156 to the compressor 3154 where it is compressed, and delivers heat (e.g., to a non-combustion reactor) at the first heat exchanger 3152. The working fluid then expands through the expansion valve 3162 and returns to the second heat exchanger 3158 via the return conduit 3160.

The working fluid can be selected based at least in part on the temperature of the source 3200 and the required delivery temperature. For example, the working fluid can be a relatively inert fluid such as Freon, ammonia, or carbon dioxide. Such fluids are compatible with various polymer and metal components. These components can include tube liner polymers such as fluorinated ethylene-propylene, perfluoroalkoxy, polyvinylidene fluoride, tetrafluoroethylene, an ethylene-propylene dimer, and/or many other materials that may be reinforced with fibers such as graphite, E-glass, S-glass, glass-ceramic or various organic filaments to form the conduits 3156, 3160. The heat exchangers 3158 can be made from metal alloys, e.g., Type 304 or other "300" series austenitic stainless steels, aluminum alloys, brass or bronze selections. The compressor 3154 can be a positive displacement or turbine type compressor depending upon factors that include the scale of the application. The expansion valve 3162 can be selected to meet the pressure drop and flow requirements of a particular application.

In a representative embodiment for which the source 3200 is at a moderate temperature (e.g., 125° F. (52° C.)), the working fluid can include carbon dioxide that is expanded through the valve 3162 to a reduced temperature (e.g., 115° F. (46° C.)). The working fluid receives heat at the source 3200 to achieve a representative temperature of 120° F. (49° C.). At the compressor 3154, the temperature of the working fluid is elevated to a representative value of 325° F. (163° C.) or higher. In particular embodiments, one or more additional heat pump cycles (not shown) can be used to further elevate the delivery temperature. It can be particularly advantageous to use heat pump cycles to deliver heat at a higher temperature than the source 3200 because such cycles typically deliver two to ten times more heat energy compared to the energy required for operation of the compressor 3154.

In a generally similar manner, it can be advantageous to use one or more heat pump cycles in reverse to cool a working fluid to a temperature below the ambient temperature and thus "refrigerate" the substance being cooled. For example, permafrost or methane hydrates in lake bottoms or ocean deposits can be cooled to a temperature far below the ambient temperature of the air or surrounding water in such applications.

Still further embodiments of suitable reactors with transmissive surfaces are disclosed in pending U.S. application Ser. No. 13/027,244, filed Feb. 14, 2011, and incorporated herein by reference.

4.4 Representative Reactors with Solar Conveyors

FIG. 16 is a partially schematic illustration of a system 4100 including a reactor vessel 4110 having a reaction zone 4111. The system 4100 further includes a solar collector 4101 that directs solar energy 4103 to the reaction zone 4111. The solar collector 4103 can include a dish, trough, heliostat arrangement, fresnel lens and/or other radiation-focusing element. The reactor vessel 4110 and the solar collector 4101 can be mounted to a pedestal 4102 that allows the solar collector 4101 to rotate about at least two orthogonal axes in order to continue efficiently focusing the solar energy 4103 as the earth rotates. The system 4100 can further include multiple reactant/product vessels 4170, including first and second reactant vessels 4170a, 4170b, and first and second product vessels, 4170c, 4170d. In particular embodiments, the first reactant vessel 4170a can provide a reactant that contains hydrogen and carbon, such as methane, which is processed at the reaction zone 4111 in an endothermic reaction to produce hydrogen and carbon which is provided to the first and second product vessels 4170c, 4170d, respectively. In other embodiments, other reactants, for example, municipal solid waste streams, biomass reactants, and/or other waste streams can be provided at a hopper 4171 forming a portion of the second reactant vessel 4170b. In any of these embodiments, an internal reactant delivery system and product removal system provide the reactants to the reaction zone 4111 and remove the products from the reaction zone 4111, as will be described in further detail later with reference to FIG. 18.

The system 4100 can further include a supplemental heat source 4180 that provides heat to the reaction zone 4111 when the available solar energy 4103 is insufficient to sustain the endothermic reaction at the reaction zone 4111. In a particular embodiment, the supplemental heat source 4180 can include an inductive heater 4181 that is positioned away from the reaction zone 4111 during the day to allow the concentrated solar energy 4103 to enter the reaction zone 4111, and can slide over the reaction zone 4111 at night to provide heat to the reaction zone 4111. The inductive heater 4181 can be powered by a renewable clean energy source, for example, hydrogen produced by the reactor vessel 4110 during the day, or falling water, geothermal energy, wind energy, or other suitable sources.

In any of the foregoing embodiments, the system 4100 can further include a controller 4190 that receives input signals 4191 and directs the operation of the devices making up the system 4100 via control signals or other outputs 4192. For example, the controller 4190 can receive a signal from a radiation sensor 4193 indicating when the incident solar radiation is insufficient to sustain the reaction at the reaction zone 4111. In response, the controller 4190 can issue a command to activate the supplemental heat source 4180. The controller 4190 can also direct the reactant delivery and product removal systems, described further below with reference to FIG. 18.

Figure 17:
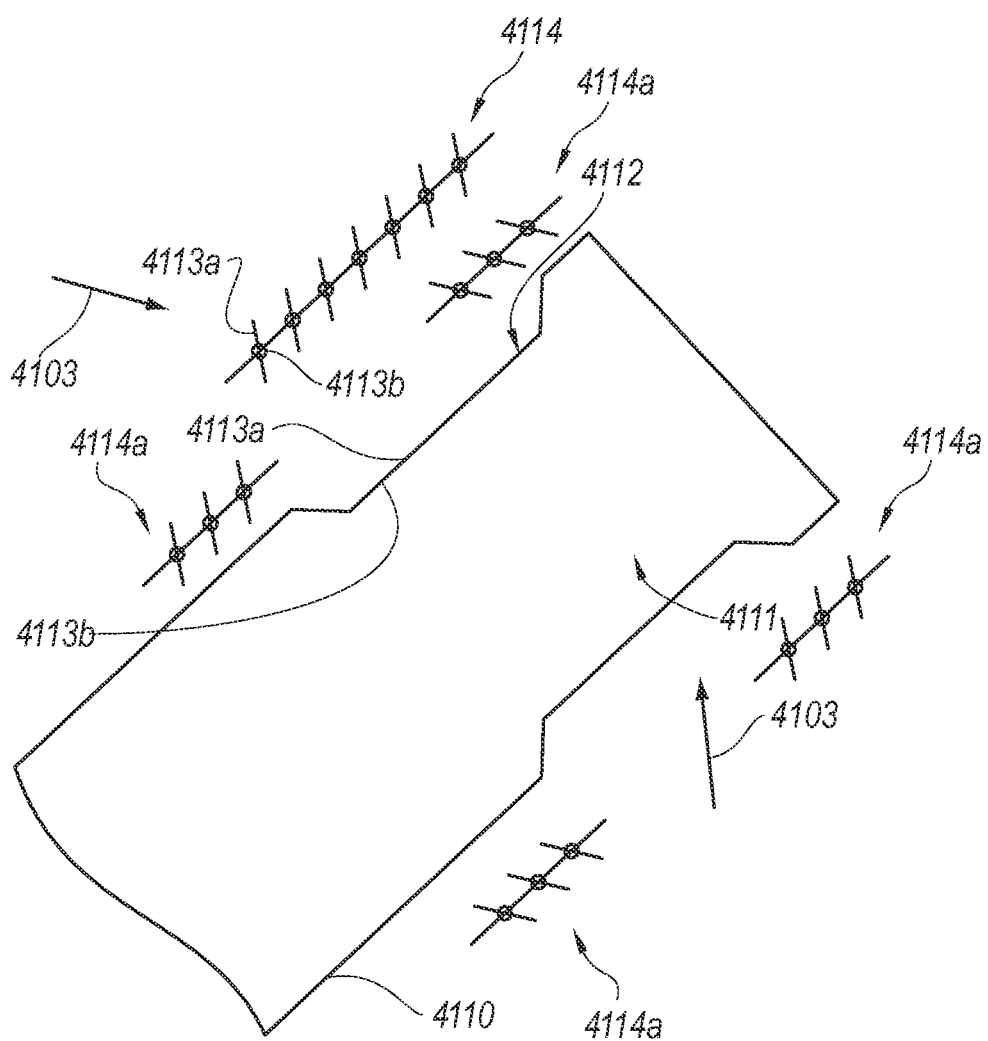
FIG. 17 is a partially schematic, enlarged illustration of a portion of a reactor vessel, including additional features for controlling the delivery of solar energy to the reaction zone in accordance with an embodiment of the disclosed technology.

FIG. 17 is a partially schematic illustration of an embodiment of the reactor vessel 4110 shown in FIG. 16, illustrating a transmissive component 4112 positioned to allow the incident solar energy 4103 to enter the reaction zone 4111. In a particular embodiment, the transmissive component 4112 can include a glass or other suitably transparent, high temperature material that is easily transmissible to solar radiation, and configured to withstand the high temperatures in the reaction zone 4111. For example, temperatures at the reaction zone 4111 are in some embodiments expected to reach 44000° F., and can be higher for the reactants and/or products.

In other embodiments, the transmissive component 4112 can include one or more elements that absorb radiation at one wavelength and re-radiate it at another. For example, the transmissive component 4112 can include a first surface 4113a that receives incident solar energy at one wavelength and a second surface 4113b that re-radiates the energy at another wavelength into the reaction zone 4111. In this manner, the energy provided to the reaction zone 4111 can be specifically tailored to match or approximate the absorption characteristics of the reactants and/or products placed within the reaction zone 4111. Further details of representative re-radiation devices were described above in Section 4.2.

In other embodiments, the reactor vessel 4110 can include other structures that perform related functions. For example, the reactor vessel 4110 can include a Venetian blind arrangement 4114 having first and second surfaces 4113a, 4113b that can be pivoted to present one surface or the other depending upon external conditions, e.g., the level of incident solar energy 4103. In a particular aspect of this embodiment, the first surface 4113a can have a relatively high absorptivity and a relatively low emissivity. This surface can accordingly readily absorb radiation during the day. The second surface 4113b can have a relatively low absorptivity and a relatively high emissivity and can accordingly operate to cool the reaction zone 4111 (or another component of the reactor 4110), e.g., at night. A representative application of this arrangement is a reactor that conducts both endothermic and exothermic reactions, as is described further in Section 4.8 below. Further details of other arrangements for operating the solar collector 4101 (FIG. R4-1) in a cooling mode are described in Section 4.5 below.

In still further embodiments, the reactor 4110 can include features that redirect radiation that "spills" (e.g., is not precisely focused on the transmissive component 4112) due to collector surface aberrations, environmental defects, non-parallel radiation, wind and/or other disturbances or distortions. These features can include additional Venetian blinds 4114a that can be positioned and/or adjusted to redirect radiation (with or without wavelength shifting) into the reaction zone 4111.

Figure 18:
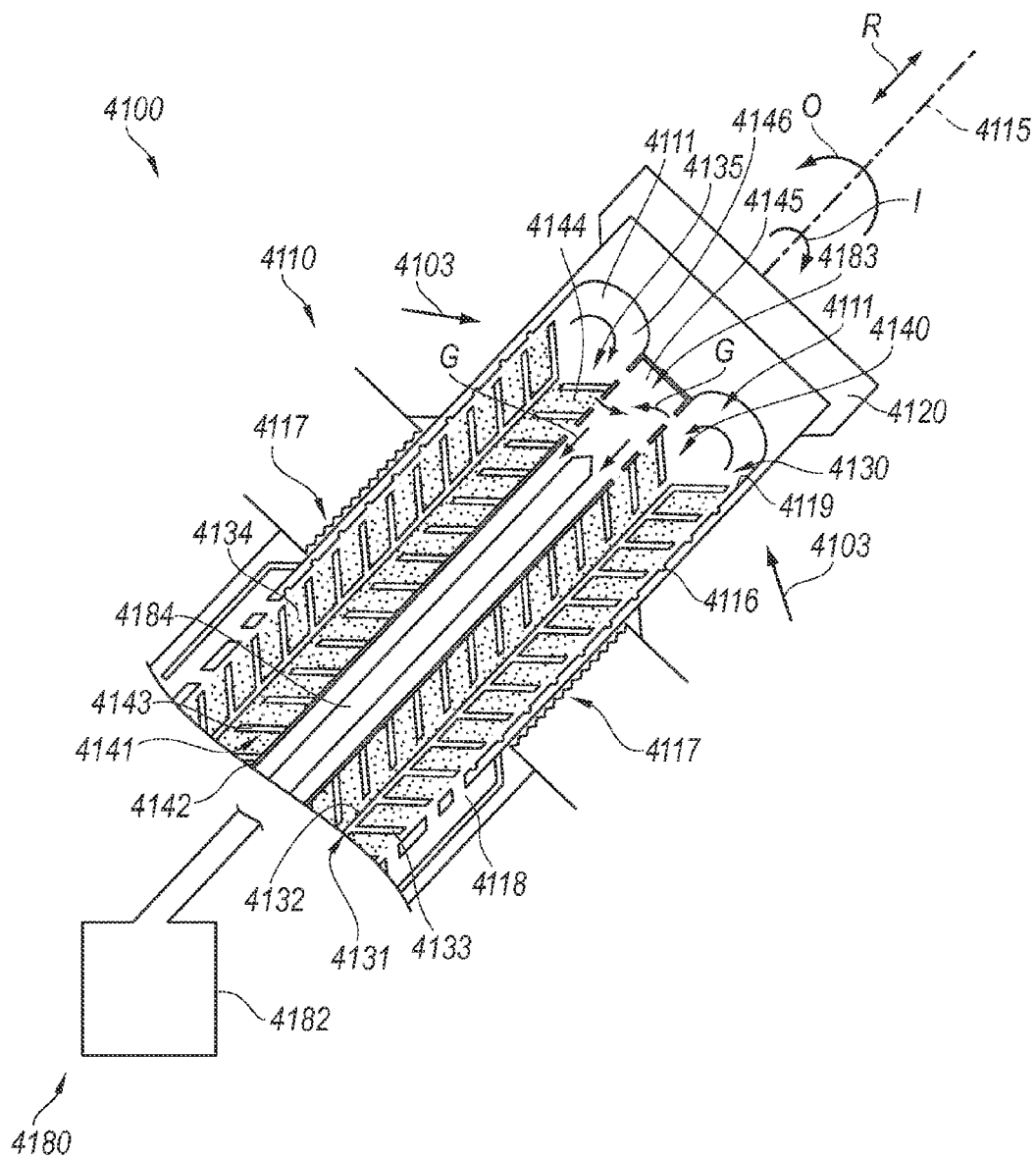
FIG. 18 is a partially schematic, cross-sectional illustration of an embodiment of a reactor vessel having annularly positioned product removal and reactant delivery systems in accordance with an embodiment of the disclosure.

FIG. 18 is a partially schematic, cross-sectional illustration of a portion of a reactor vessel 4110 configured in accordance with an embodiment of the present disclosure. In one aspect of this embodiment, the reactor 4110 includes a reactant delivery system 4130 that is positioned within a generally cylindrical, barrel-shaped reactor vessel 4110, and a product removal system 4140 positioned annularly inwardly from the reactant delivery system 4130. For example, the reactant delivery system 4130 can include an outer screw 4131, which in turn includes an outer screw shaft 4132 and outwardly extending outer screw threads 4133. The outer screw 4131 has an axially extending first axial opening 4135 in which the product removal system 4140 is positioned. The outer screw 4131 rotates about a central rotation axis 4115, as indicated by arrow O. As it does so, it carries at least one reactant 4134 (e.g., a gaseous, liquid, and/or solid reactant) upwardly and to the right as shown in FIG. R4-3, toward the reaction zone 4111. As the reactant 4134 is carried within the outer screw threads 4133, it is also compacted, potentially releasing gases and/or liquids, which can escape through louvers and/or other openings 4118 located annularly outwardly from the outer screw 4131. As the reactant 4134 becomes compacted in the outer screw threads 4133, it forms a seal against an inner wall 4119 of the vessel 4110. This arrangement can prevent losing the reactant 4134, and can instead force the reactant 4134 to move toward the reaction zone 4111. The reactant delivery system 4130 can include other features, in addition to the outer screw threads 4133, to force the reactant 4134 toward the reaction zone 4111. For example, the inner wall 4119 of the reactor vessel 4110 can include one or more spiral rifle grooves 4116 that tend to force the reactant 4134 axially as the outer screw 4131 rotates. In addition to, or in lieu of this feature, the entire outer screw 4131 can reciprocate back and forth, as indicated by arrow R to prevent the reactant 4134 from sticking to the inner wall 4119, and/or to release reactant 4134 that may stick to the inner wall 4119. A barrel heater 4117 placed near the inner wall 4119 can also reduce reactant sticking, in addition to or in lieu of the foregoing features. In a least some embodiments, it is expected that the reactant 4134 will be less likely to stick when warm.

The reactant 4134 can include a variety of suitable compositions, e.g., compositions that provide a hydrogen donor to the reaction zone 4111. In representative embodiments, the reactant 4134 can include biomass constituents, e.g., municipal solid waste, commercial waste, forest product waste or slash, cellulose, lignocellulose, hydrocarbon waste (e.g., tires), and/or others. After being compacted, these waste products can be highly subdivided, meaning that they can readily absorb incident radiation due to rough surface features and/or surface features that re-reflect and ultimately absorb incident radiation. This property can further improve the efficiency with which the reactant 4134 heats up in the reaction zone 4111.

Once the reactant 4134 has been delivered to the reaction zone 4111, it receives heat from the incident solar energy 4103 or another source, and undergoes an endothermic reaction. The reaction zone 4111 can have an annular shape and can include insulation 4120 to prevent heat from escaping from the vessel 4110. In one embodiment, the endothermic reaction taking place at the reaction zone 4111 includes dissociating methane, and reforming the carbon and hydrogen constituents into elemental carbon and diatomic hydrogen, or other carbon compounds (e.g., oxygenated carbon in the form of carbon monoxide or carbon dioxide) and hydrogen compounds. The resulting product 4146 can include gaseous portions (indicated by arrow G), which passed annularly inwardly from the reaction zone 4111 to be collected by the product removal system 4140. Solid portions 4144 (e.g., ash and/or other byproducts) of the product 4146 are also collected by the product removal system 4140.

The product removal system 4140 can include an inner screw 4141 positioned in the first axial opening 4135 within the outer screw 4131. The inner screw 4141 can include an inner screw shaft 4142 and inner screw threads 4143. The inner screw 4141 can also rotate about the rotation axis 4115, as indicated by arrow I, in the same direction as the outer screw 4131 or in the opposite direction. The inner screw 4141 includes a second axial passage 4145 having openings that allow the gaseous product G to enter. The gaseous product G travels down the second axial opening 4145 to be collected and, in at least some instances, further processed (e.g., to isolate the carbon produced in the reaction from the hydrogen produced in the reaction). In particular embodiments, the gaseous product G can exchange additional heat with the incoming reactant 4134 via an additional heat exchanger (not shown in FIG. 18) to cool the product G and heat the reactant 4134. In other embodiments, the gaseous product G can be cooled by driving a Stirling engine or other device to generate mechanical and/or electric power. As the inner screw 4141 rotates, it carries the solid portions 4144 of the product 4146 downwardly and to the left as shown in FIG. 18. The solid products 4144 (and the gaseous product G) can convey heat via conduction to the outer screw 4130 to heat the incoming reactant 4134, after which the solid portions 4144 can be removed for use. For example, nitrogenous and/or sulfurous products from the reaction performed at the reaction zone 4111 can be used in agricultural or industrial processes. The products and therefore the chemical and physical composition of the solid portions can depend on the characteristics of the incoming reactants, which can vary widely, e.g., from municipal solid waste to industrial waste to biomass.

As discussed above with reference to FIGS. 16 and 17, the system 4100 can include features that direct energy (e.g., heat) into the reaction zone 4111 even when the available solar energy is insufficient to sustain the reaction. In an embodiment shown in FIG. 18, the supplemental heat source 4180 can include combustion reactants 4182 (e.g., an oxidizer and/or a hydrogen-containing combustible material) that is directed through a delivery tube 4184 positioned in the second axial opening 4145 to a combustor or combustor zone 4183 that is in thermal communication with the reaction zone 4111. During the night or other periods of time when the incident solar energy is low, the supplemental heat source 4180 can provide additional heat to the reaction zone 4111 to sustain the endothermic reaction taking place therein.

One feature of an embodiment described above with reference to FIG. 18 is that the incoming reactant 4134 can be in close or intimate thermal communication with the solid product 4144 leaving the reaction zone. In particular, the outer screw shaft 4132 and outer screw threads 4133 can be formed from a highly thermally conductive material, so as to receive heat from the solid product 4144 carried by the inner screw 4141, and deliver the heat to the incoming reactant 4134. An advantage of this arrangement is that it is thermally efficient because it removes heat from products that would otherwise be cooled in a manner that wastes the heat, and at the same time heats the incoming reactants 4134, thus reducing the amount of heat that must be produced by the solar concentrator 4101 (FIG. 16) and/or the supplemental heat source 4180. By improving the efficiency with which hydrogen and/or carbon or other building blocks are produced in the reactor vessel 4110, the reactor system 4100 can increase the commercial viability of the renewable reactants and energy sources used to produce the products.

Still further embodiments of suitable reactors with solar conveyors are disclosed in issued U.S. Pat. No. 8,187,549, incorporated herein by reference.

4.5 Representative Reactors with Solar Concentrators

Figure 19:
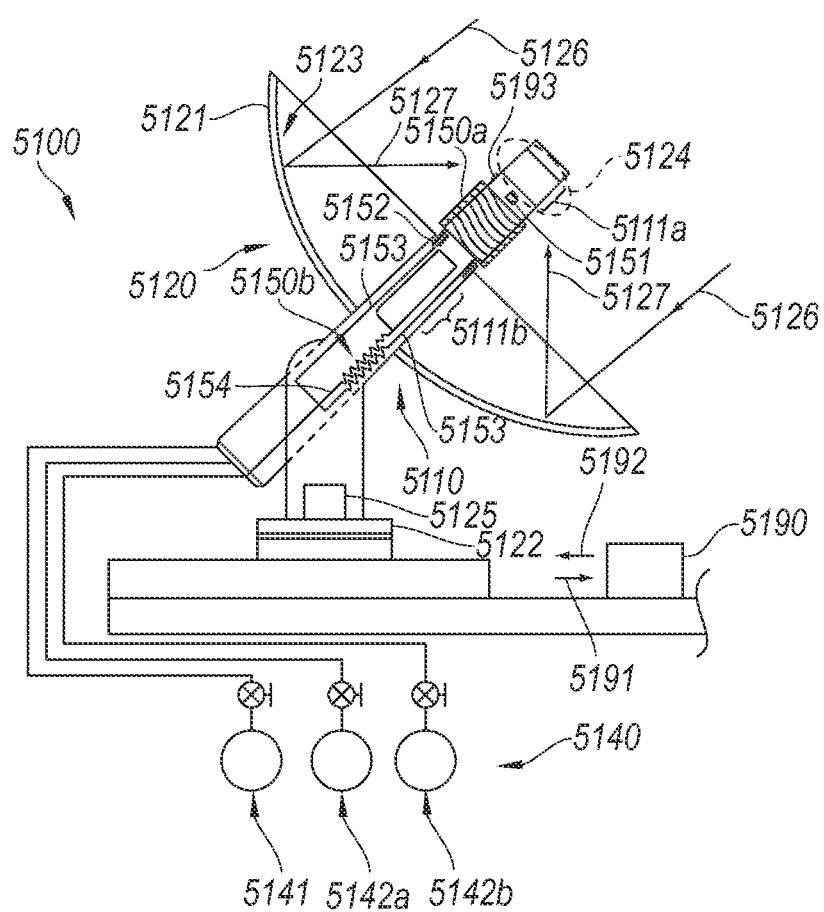
FIG. 19 is a partially schematic, partial cross-sectional illustration of a system having a solar concentrator configured in accordance with an embodiment of the present technology.

FIG. 19 is a partially schematic, partial cross-sectional illustration of a system 5100 having a reactor 5110 coupled to a solar concentrator 5120 in accordance with the particular embodiment of the technology. In one aspect of this embodiment, the solar concentrator 5120 includes a dish 5121 mounted to pedestal 5122. The dish 5121 can include a concentrator surface 5123 that receives incident solar energy 5126, and directs the solar energy as focused solar energy 5127 toward a focal area 5124. The dish 5121 can be coupled to a concentrator actuator 5125 that moves the dish 5121 about at least two orthogonal axes in order to efficiently focus the solar energy 5126 as the earth rotates. As will be described in further detail below, the concentrator actuator 5125 can also be configured to deliberately position the dish 5121 to face away from the sun during a cooling operation.

The reactor 5110 can include one or more reaction zones 5111, shown in FIG. R5-1 as a first reaction zone 5111a and second reaction zone 5111b. In a particular embodiment, the first reaction zone 5111a is positioned at the focal area 5124 to receive the focused solar energy 5127 and facilitate a dissociation reaction or other endothermic reaction. Accordingly, the system 5100 can further include a distribution/collection system 5140 that provides reactants to the reactor 5110 and collects products received from the reactor 5110. In one aspect of this embodiment, the distribution/collection system 5140 includes a reactant source 5141 that directs a reactant to the first reaction zone 5111a, and one or more product collectors 5142 (two are shown in FIG. R5-1 as a first product collector 5142a and a second product collector 5142b) that collect products from the reactor 5110. When the reactor 5110 includes a single reaction zone (e.g. the first reaction zone 5111a) the product collectors 5142a, 5142b can collect products directly from the first reaction zone 5111a. In another embodiment, intermediate products produced at the first reaction zone 5111a are directed to the second reaction zone 5111b. At the second reaction zone 5111b, the intermediate products can undergo an exothermic reaction, and the resulting products are then delivered to the product collectors 5142a, 5142b along a product flow path 5154. For example, in a representative embodiment, the reactant source 5141 can include methane and carbon dioxide, which are provided (e.g., in an individually controlled manner) to the first reaction zone 5111a and heated to produce carbon monoxide and hydrogen. The carbon monoxide and hydrogen are then provided to the second reaction zone 5111b to produce methanol in an exothermic reaction. Further details of this arrangement and associated heat transfer processes between the first reaction zone 5111a and second reaction zone 5111b are described in more detail below in Section 4.8.

In at least some instances, it is desirable to provide cooling to the reactor 5110, in addition to the solar heating described above. For example, cooling can be used to remove heat produced by the exothermic reaction being conducted at the second reaction zone 5111b and thus allow the reaction to continue. When the product produced at the second reaction zone 5111b includes methanol, it may desirable to further cool the methanol to a liquid to provide for convenient storage and transportation. Accordingly, the system 5100 can include features that facilitate using the concentrator surface 5123 to cool components or constituents at the reactor 5110. In a particular embodiment, the system 5100 includes a first heat exchanger 5150a operatively coupled to a heat exchanger actuator 5151b that moves the first heat exchanger 5150a relative to the focal area 5124. The first heat exchanger 5150a can include a heat exchanger fluid that communicates thermally with the constituents in the reactor 5110, but is in fluid isolation from these constituents to avoid contaminating the constituents and/or interfering with the reactions taking place in the reactor 5110. The heat exchanger fluid travels around a heat exchanger fluid flow path 5153 in a circuit from the first heat exchanger 5150a to a second heat exchanger 5150b and back. At the second heat exchanger 5150b, the heat exchanger fluid receives heat from the product (e.g. methanol) produced by the reactor 5110 as the product proceeds from the second reaction zone 5111b to the distribution/collection system 5140. The heat exchanger fluid flow path 5153 delivers the heated heat exchanger fluid back to the first heat exchanger 5150a for cooling. One or more strain relief features 5152 in the heat exchanger fluid flow path 5153 (e.g., coiled conduits) facilitate the movement of the first heat exchanger 5150a. The system 5100 can also include a controller 5190 that receives input signals 5191 from any of a variety of sensors, transducers, and/or other elements of the system 5100, and, in response to information received from these elements, delivers control signals 5192 to adjust operational parameters of the system 5100.

Figure 20:
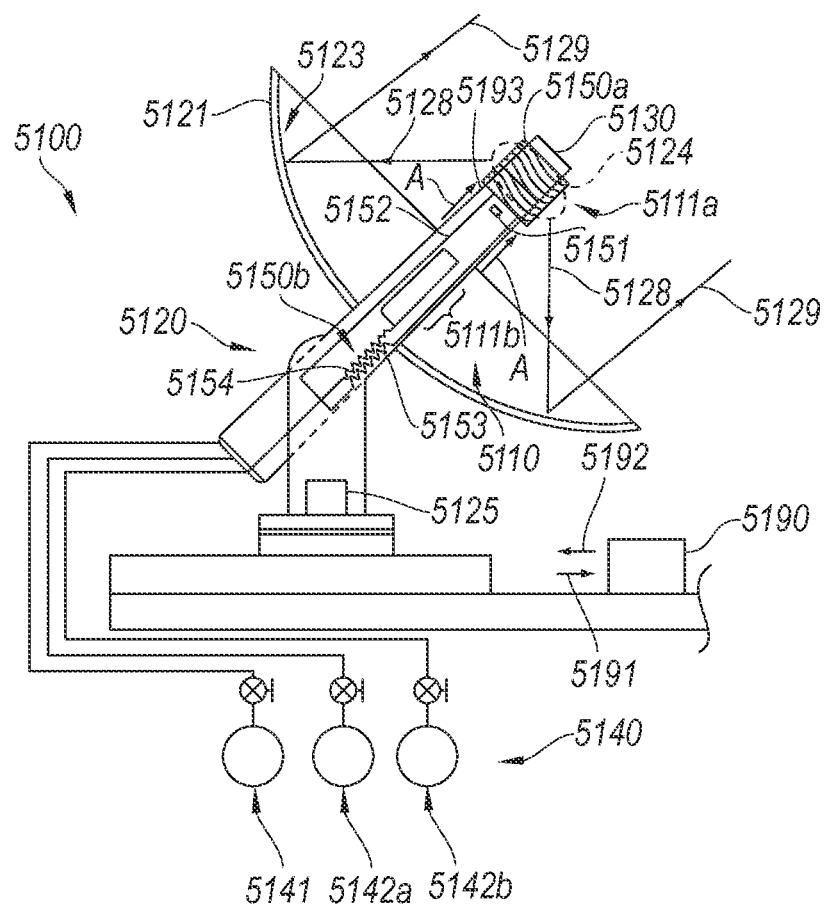
FIG. 20 is a partially schematic, partial cross-sectional illustration of an embodiment of the system shown in FIG. 1 with the solar concentrator configured to emit energy in a cooling process, in accordance with an embodiment of the disclosure.

FIG. 20 illustrates one mechanism by which the heat exchanger fluid provided to the first heat exchanger 5150a is cooled. In this embodiment, the controller 5190 directs the heat exchanger actuator 5151 to drive the first heat exchanger 5150a from the position shown in FIG. 19 to the focal area 5124, as indicated by arrows A. In addition, the controller 5190 can direct the concentrator actuator 5125 to position the dish 5121 so that the concentrator surface 5123 points away from the sun and to an area of the sky having very little radiant energy. In general, this process can be completed at night, when it is easier to avoid the radiant energy of the sun and the local environment, but in at least some embodiments, this process can be conducted during the daytime as well. A radiant energy sensor 5193 coupled to the controller 5190 can detect when the incoming solar radiation passes below a threshold level, indicating a suitable time for positioning the first heat exchanger 5150a in the location shown in FIG. 20.

With the first heat exchanger 5150a in the position shown in FIG. 20, the hot heat transfer fluid in the heat exchanger 5150a radiates emitted energy 5128 that is collected by the dish 5121 at the concentrator surface 5123 and redirected outwardly as directed emitted energy 5129. An insulator 5130 positioned adjacent to the focal area 5124 can prevent the radiant energy from being emitted in direction other than toward the concentrator surface 5123. By positioning the concentrator surface 5123 to point to a region in space having very little radiative energy, the region in space can operate as a heat sink, and can accordingly receive the directed emitted energy 5129 rejected by the first heat exchanger 5150a. The heat exchanger fluid, after being cooled at the first heat exchanger 5150a returns to the second heat exchanger 5150b to absorb more heat from the product flowing along the product flow path 5154. Accordingly, the concentrator surface 5123 can be used to cool as well as to heat elements of the reactor 5110.

In a particular embodiment, the first heat exchanger 5150a is positioned as shown in FIG. 19 during the day, and as positioned as shown in FIG. 20 during the night. In other embodiments, multiple systems 5100 can be coupled together, some with the corresponding first heat exchanger 5150a positioned as shown in FIG. 19, and others with the first heat exchanger 5150a positioned as shown in FIG. 20, to provide simultaneous heating and cooling. In any of these embodiments, the cooling process can be used to liquefy methanol, and/or provide other functions. Such functions can include liquefying or solidifying other substances, e.g., carbon dioxide, ethanol, butanol or hydrogen.

In particular embodiments, the reactants delivered to the reactor 5110 are selected to include hydrogen, which is dissociated from the other elements of the reactant (e.g. carbon, nitrogen, boron, silicon, a transition metal, and/or sulfur) to produce a hydrogen-based fuel (e.g. diatomic hydrogen) and a structural building block that can be further processed to produce durable goods. Such durable goods include graphite, graphene, and/or polymers, which may produced from carbon structural building blocks, and other suitable compounds formed from hydrogenous or other structural building blocks.

Further details of suitable processes and products are disclosed in the following co-pending U.S. patent applications: Ser. No. 13/027,208 titled "CHEMICAL PROCESSES AND REACTORS FOR EFFICIENTLY PRODUCING HYDROGEN FUELS AND STRUCTURAL MATERIALS, AND ASSOCIATED SYSTEMS AND METHODS"; Ser. No. 13/027,214 titled "ARCHITECTURAL CONSTRUCT HAVING FOR EXAMPLE A PLURALITY OF ARCHITECTURAL CRYSTALS"; and Ser. No. 12/027,068 titled "CARBON-BASED DURABLE GOODS AND RENEWABLE FUEL FROM BIOMASS WASTE DISSOCIATION", all of which were filed Feb. 14, 2011 and are incorporated herein by reference.

Figure 21:
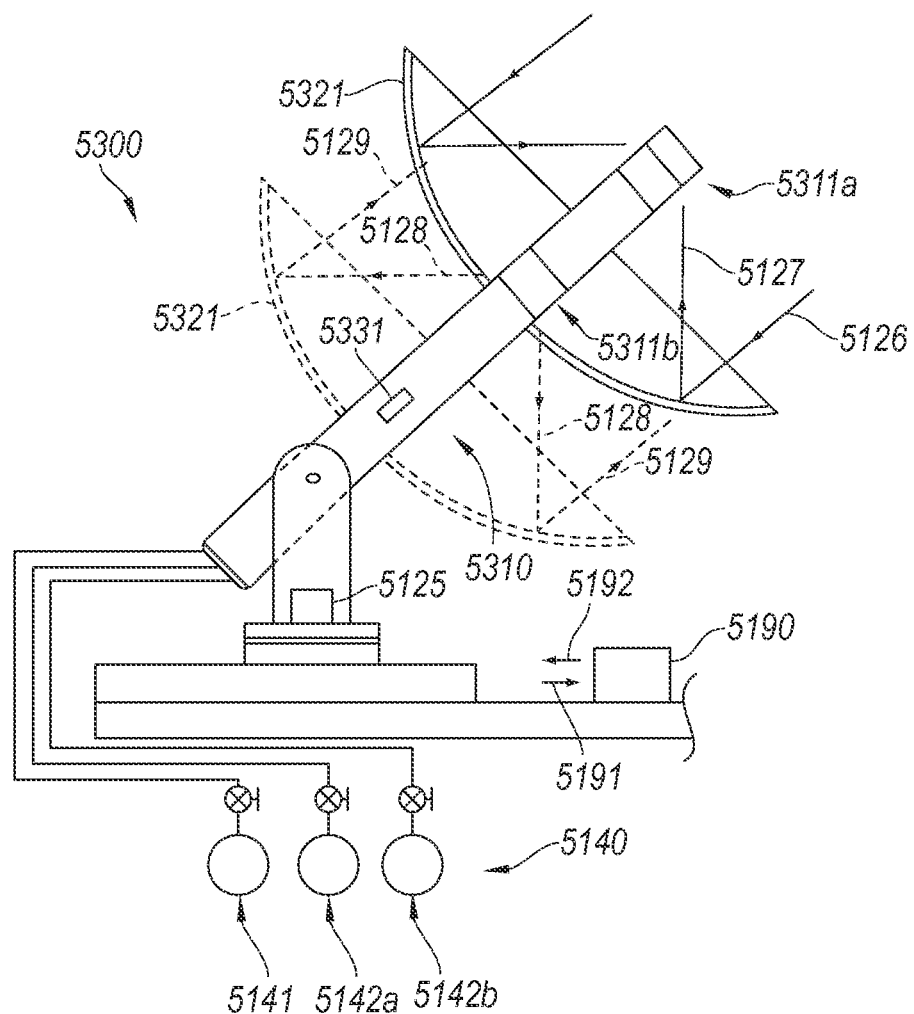
FIG. 21 is a partially schematic, partial cross-sectional illustration of a system having a movable solar concentrator dish in accordance with an embodiment of the disclosure.

FIG. 21 illustrates a system 5300 having a reactor 5310 with a movable dish 5321 configured in accordance another embodiment of the disclosed technology. In a particular aspect of this embodiment, the reactor 5310 includes a first reaction zone 5311a and a second reaction zone 5311b, with the first reaction zone 5311a receiving focused solar energy 5127 when the dish 5321 has a first position, shown in solid lines in FIG. 21. The dish 5321 is coupled to a dish actuator 5331 that moves the dish 5321 relative to the reaction zones 5311a, 5311b. Accordingly, during a second phase of operation, the controller 5190 directs the dish actuator 5331 to move the dish 5321 to the second position shown in dashed lines in FIG. 21. In one embodiment, this arrangement can be used to provide heat to the second reaction zone 5311b when the dish 5321 is in the second position. In another embodiment, this arrangement can be used to cool the second reaction zone 5311b. Accordingly, the controller 5190 can direct the concentrator actuator 5125 to point the dish 5321 to a position in the sky having little or no radiant energy, thus allowing the second reaction zone 5311b to reject heat to the dish 5321 and ultimately to space, in a manner generally similar to that described above with reference to FIGS. 19 and 20.

Still further embodiments of suitable reactors with solar concentrators are disclosed in issued U.S. Pat. No. 8,187,550, incorporated herein by reference.

4.6 Representative Reactors with Induction Heating

Figure 22:
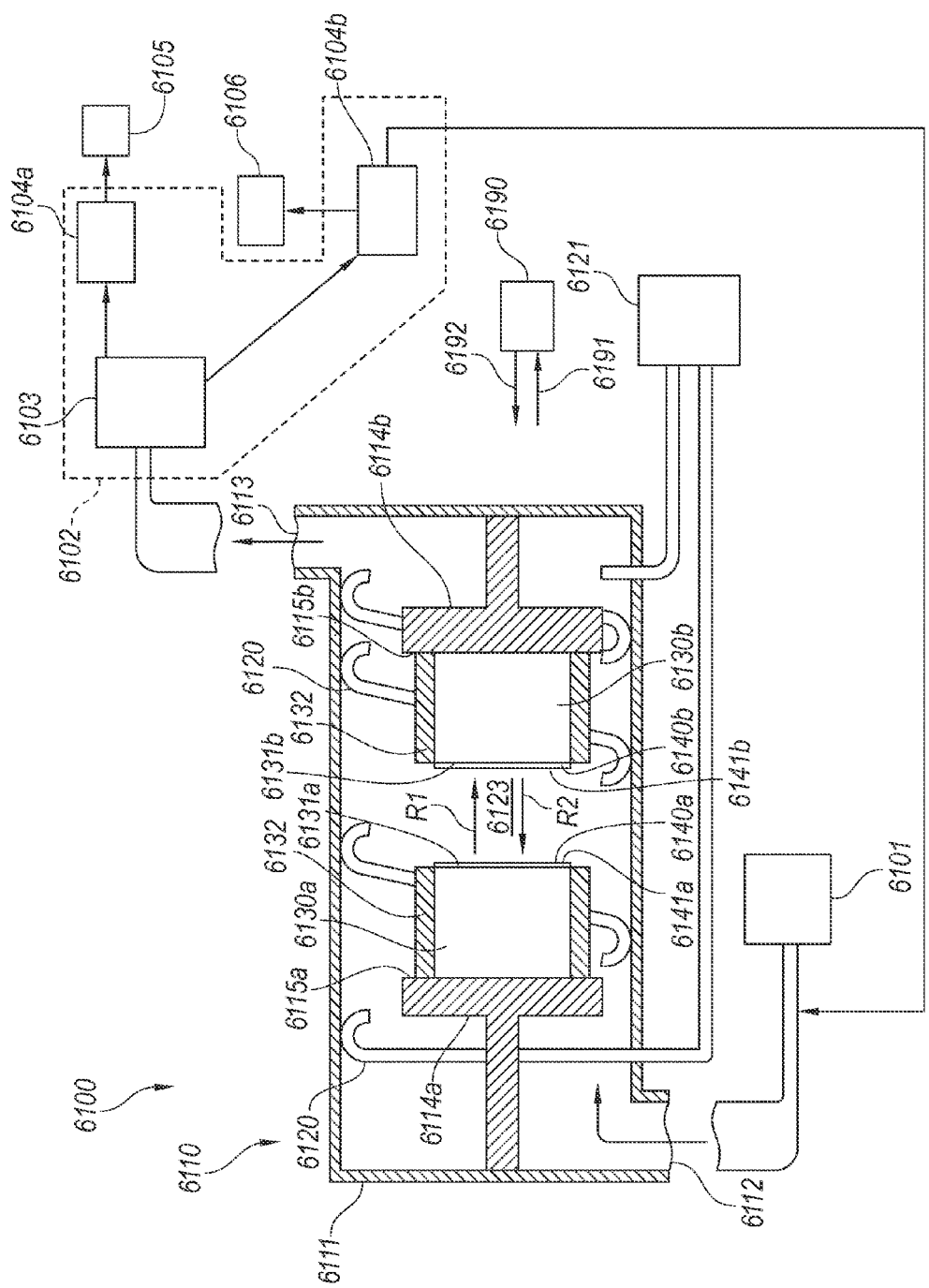
FIG. 22 is a partially schematic illustration of a system having a reactor with facing substrates for operation in a batch mode in accordance with an embodiment of the presently disclosed technology.

FIG. 22 is a partially schematic, partial cross-sectional illustration of a system 6100 having a reactor 6110 configured in accordance with an embodiment of the presently disclosed technology. In one aspect of this embodiment, the reactor 6110 includes a reactor vessel 6111 having a reaction or induction zone 6123 which is heated by an induction coil 6120. The induction coil 6120 can be a liquid-cooled, high frequency alternating current coil coupled to a suitable electrical power source 6121. The reactor vessel 6111 can further include an entrance port 6112 coupled to a precursor gas source 6101 to receive a suitable precursor gas, and an exit port 6113 positioned to remove spent gas and/or other constituents from the vessel 6111. In a particular embodiment, the precursor gas source 6101 carries a hydrocarbon gas (e.g., methane), which is dissociated into carbon and hydrogen at the induction zone 6123. The carbon is then deposited on a substrate to form a product, as is described further below, and the hydrogen and/or other constituents are removed for further processing, as is also described further below.

The reaction vessel 6111 houses a first support 6114a having a first support surface 6115a, and a second support 6114b having a second support surface 6115b facing toward the first support surface 6115a. Each support 6114a, 6114b can carry a substrate upon which one or more constituents of the precursor gas are deposited. For example, the first support 6114a can carry a first substrate 6130a and the second support 6114b can carry a second substrate 6130b. In a representative embodiment in which the precursor gas is selected to deposit carbon, the first and second substrates 6130a, 6130b can also include carbon, e.g., in the form of graphite or a constituent of steel. When the precursor gas includes a different deposition element (e.g., nitrogen and/or boron), the composition of the first and second substrates 6130a, 6130b can be different. Each of the substrates 6130a, 6130b can have an initially exposed surface facing the other. Accordingly, the first substrate 6130a can have an exposed first surface 6131a facing toward a second exposed surface 6131b of the second substrate 6130b. The remaining surfaces of each substrate 6130a, 6130b can be insulated to prevent or significantly restrict radiation losses from these surfaces. The supports 6114a, 6114b can insulate at least one surface of each of the substrates 6130a, 6130b. The other surfaces (other than the exposed first and second substrates 6131a, 6131b) can be protected by a corresponding insulator 6132. The insulator 6132 can be formed from a suitable high temperature ceramic or other material.

The system 6100 can further include a controller 6190 that receives input signals 6191 from any of a variety of sensors, transducers, and/or other elements of the system 6100, and in response to information received from these elements, delivers control signals 6192 to adjust operational parameters of the system 6100. These parameters can include the pressures and flow rates with which the gaseous constituents are provided to and/or removed from the reactor vessel 6111, the operation of the induction coil 6120 and associated power source 6121, and the operation of a separator 6103 (described below), among others.

In operation, the precursor gas source 6101 supplies gas to the induction zone 6123, the induction coil 6120 is activated, and the precursor gas dissociates into at least one constituent (e.g., carbon) that is deposited onto the first and second substrates 6130a, 6130b. The constituent can be deposited in an epitaxial process that preserves the crystal grain orientation of the corresponding substrate 6130a, 6130b. Accordingly, the deposited constituent can also have a crystal and/or other self-organized structure. As the constituent is deposited, it forms a first formed structure or product 6140a at the first substrate 6130a, and a second formed structure or product 6140b at the second substrate 6130b. The first and second formed structures 6140a, 6140b each have a corresponding exposed surface 6141a, 6141b facing toward the other. The structures 6140a, 6140b can have the same or different cross-sectional shapes and/or areas, and/or can have non-crystalline, single crystal or multicrystal organizations, depending upon the selected embodiment. Radiation emitted by the first exposed surface 6131a of the first substrate 6130a, and/or by the first exposed surface 6141a of the first formed structure 6140a (collectively identified by arrow R1) is received at the second exposed surface 6141b of the second formed structure 6140b, and/or the second exposed surface 6131b of the second substrate 6130b. Similarly, radiation emitted by the second exposed surface 6141b of the second formed structure 6140b and/or the second exposed surface 6131b of the second substrate 6130b (collectively identified by arrow R2) is received at the first formed structure 6140a and/or the first substrate 6130a.

As the formed structures 6140a, 6140b grow, the exit port 6113 provides an opening through which residual constituents from the dissociated precursor gas and/or non-dissociated quantities of the precursor gas can pass. These constituents are directed to a collection system 6102, which can include a separator 6103 configured to separate the constituents into two or more flow streams. For example, the separator 6103 can direct one stream of constituents to a first product collector 6104*a*, and a second stream of constituents to a second product collector 6104*b*. In a particular embodiment, the first product collector 6104*a* can collect pure or substantially pure hydrogen, which can be delivered to a hydrogen-based fuel cell 6105 or other device that requires hydrogen at a relatively high level of purity. The second stream of constituents directed to the second product collector 6104*b* can include hydrogen mixed with other elements or compounds. Such elements or compounds can include methane or another undissociated precursor gas, and/or carbon (or another element or compound targeted for deposition) that was not deposited on the first substrate 6130*a* or the second substrate 6130*b*. These constituents can be directed to an engine 6106, for example, a turbine engine or another type of internal combustion engine that can burn a mixture of hydrogen and the other constituents. The engine 6106 and/or the fuel cell 6105 can provide power for any number of devices, including the electrical power source 6121 for the inductive coil 6120. In another aspect of this embodiment, at least some of the constituents (e.g., undissociated precursor gas) received at the second collector 6104*b* can be directed back into the reactor 6110 via the entrance port 6112.

An advantage of the foregoing arrangement is that the radiation losses typically encountered in a chemical vapor deposition apparatus can be avoided by positioning multiple substrates in a manner that allows radiation emitted from one surface to be received by another surface that is also targeted for deposition. In a particular embodiment shown in FIG. 22, two substrates are shown, each having a single exposed surface facing the other. In other embodiments, additional substrates can be positioned (e.g., in a plane extending inwardly and/or outwardly transverse to the plane of FIG. 22) to allow additional exposed surfaces of a formed product to radiate heat to corresponding surfaces of other formed products.

Another advantage of the foregoing arrangement is that it can be used to produce a structural building block and/or an architectural construct, as well as clean burning hydrogen fuel from a hydrogen donor. When the precursor gas includes a hydrocarbon, the architectural construct can include graphene and/or another carbon-bearing material, for example, a material that can be further processed to form a carbon-based composite or a carbon-based polymer. In other embodiments, the precursor gas can include other elements (e.g., boron, nitrogen, sulfur, silicon, and/or a transition metal) than can also be used to form structural building blocks that contain the element, and/or architectural constructs formed from the building blocks. Suitable processes and representative architectural constructs are further described in the following co-pending U.S. patent applications, all of which were filed on Feb. 14, 2011 and are incorporated herein by reference: application Ser. No. 13/027,208; application Ser. No. 13/027,214; and application Ser. No. 13/027,068.

One feature of an embodiment described above with reference to FIG. 22 is that it may be conducted in a batch process. For example, each of the first and second formed structures 6140*a*, 6140*b* can be grown by a particular amount and then removed from the reaction vessel 6111. In other embodiments, the products can be formed in a continuous manner, without the need for halting the reaction to remove the product.

Still further embodiments of suitable reactors with induction heating are disclosed in pending U.S. application Ser. No. 13/027,215, filed Feb. 14, 2011, and incorporated herein by reference.

4.7 Representative Reactors Using Engine Heat

Figure 23:
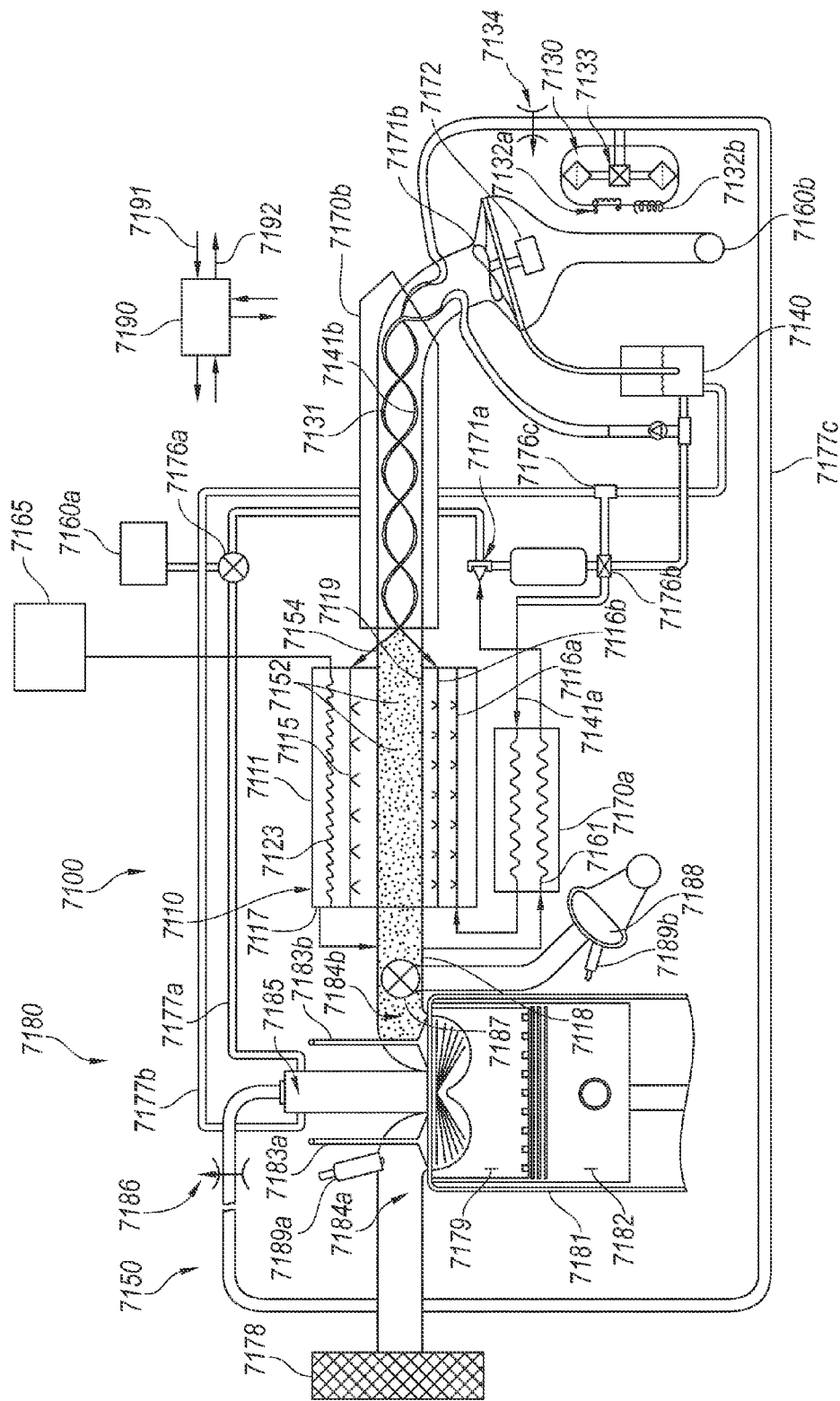
FIG. 23 is a partially schematic, partially cross-sectional illustration of a reactor system that receives energy from a combustion engine and returns reaction products to the engine in accordance with an embodiment of the presently disclosed technology.

FIG. 23 is a partially schematic illustration of system 7100 that includes a reactor 7110 in combination with a radiant energy/reactant source 7150 in accordance with another embodiment of the technology. In this embodiment, the radiant energy/reactant source 7150 includes an engine 7180, e.g., an internal combustion engine having a piston 7182 that reciprocates within a cylinder 7181. In other embodiments, the engine 7180 can have other configurations, for example, an external combustion configuration. In an embodiment shown in FIG. 23, the engine 7180 includes an intake port 7184*a* that is opened and closed by an intake valve 7183*a* to control air entering the cylinder 7181 through an air filter 7178. The air flow can be unthrottled in an embodiment shown in FIG. 23, and can be throttled in other embodiments. A fuel injector 7185 directs fuel into the combustion zone 7179 where it mixes with the air and ignites to produce the combustion products 7152. Additional fuel can be introduced by an injection valve 7189*a*. The combustion products 7152 exit the cylinder 7181 via an exhaust port 7184*b* controlled by an exhaust valve 7183*b*. Further details of representative engines and ignition systems are disclosed in co-pending U.S. application Ser. No. 12/653,085 filed on Dec. 7, 2010, and incorporated herein by reference.

The engine 7180 can include features specifically designed to integrate the operation of the engine with the operation of the reactor 7110. For example, the engine 7180 and the reactor 7110 can share fuel from a common fuel source 7130 which is described in further detail below. The fuel is provided to the fuel injector 7185 via a regulator 7186. The engine 7180 can also receive end products from the reactor 7110 via a first conduit or passage 7177*a*, and water (e.g., liquid or steam) from the reactor 7110 via a second conduit or passage 7177*b*. Further aspects of these features are described in greater detail below, following a description of the other features of the overall system 7100.

The system 7100 shown in FIG. 23 also includes heat exchangers and separators configured to transfer heat and segregate reaction products in accordance with the disclosed technology. In a particular aspect of this embodiment, the system 7100 includes a steam/water source 7140 that provides steam to the reactor vessel 7111 to facilitate product formation. Steam from the steam/water source 7140 can be provided to the reactor 7110 via at least two channels. The first channel includes a first water path 7141*a* that passes through a first heat exchanger 7170*a* and into the reactor vessel 7111 via a first steam distributor 7116*a*. Products removed from the reactor vessel 7111 pass through a reactor product exit port 7117 and along a products path 7161. The products path 7161 passes through the first heat exchanger 7170*a* in a counter-flow or counter-current manner to cool the products and heat the steam entering the reactor vessel 7111. The products continue to a reaction product separator 7171*a* that segregates useful end products (e.g., hydrogen and carbon or carbon compounds). At least some of the products are then directed back to the engine 7180, and other products are then collected at a products collector 7160*a*. A first valve 7176*a* regulates the product flow. Water remaining in the products path 7161 can be separated at the reaction product separator 7171*a* and returned to the steam/water source 7140.

The second channel via which the steam/water source 7140 provides steam to the reactor 7110 includes a second water path 7141*b* that passes through a second heat exchanger 7170*b*. Water proceeding along the second water path 7141*b* enters the reactor 7110 in the form of steam via a second stream distributor 7116*b*. This water is heated by combustion products that have exited the combustion zone 7179 and passed through the transfer passage 7118 (which can include a transmissive surface 7119) along a combustion products path 7154. The spent combustion products 7152 are collected at a combustion products collector 7160b and can include nitrogen compounds, phosphates, re-used illuminant additives (e.g., sources of sodium, magnesium and/or potassium), and/or other compositions that may be recycled or used for other purposes (e.g., agricultural purposes). The illuminant additives can be added to the combustion products 7152 (and/or the fuel used by the engine 7180) upstream of the reactor 7110 to increase the amount of radiant energy available for transmission into the reaction zone 7112.

In addition to heating water along the second water path 7141b and cooling the combustion products along the combustion products path 7154, the second heat exchanger 7170b can heat the hydrogen donor passing along a donor path 7131 to a donor distributor 7115 located within the reactor vessel 7111. The donor vessel 7130 houses a hydrogen donor, e.g., a hydrocarbon such as methane, or a nitrogenous donor such as ammonia. The donor vessel 7130 can include one or more heaters 7132 (shown as first heater 7132a and a second heater 7132b) to vaporize and/or pressurize the hydrogen donor within. A three-way valve 7133 and a regulator 7134 control the amount of fluid and/or vapor that exits the donor vessel 7130 and passes along the donor path 7131 through the second heat exchanger 7170b and into the reactor vessel 7111. As discussed above, the hydrogen donor can also serve as a fuel for the engine 7180, in at least some embodiments, and can be delivered to the engine 7180 via a third conduit or passage 7177c.

In the reactor vessel 7111, the combustion products 7152 pass through the combustion products passage 7118 while delivering radiant energy and/or reactants through the transmissive surface 7119 into the reaction zone 7112. After passing through the second heat exchanger 7170b, the combustion products 7152 can enter a combustion products separator 7171b that separates water from the combustion products. The water returns to the steam/water source 7140 and the remaining combustion products are collected at the combustion products collector 7160b. In a particular embodiment, the separator 7171b can include a centrifugal separator that is driven by the kinetic energy of the combustion product stream. If the kinetic energy of the combustion product stream is insufficient to separate the water by centrifugal force, a motor/generator 7172 can add energy to the separator 7171b to provide the necessary centrifugal force. If the kinetic energy of the combustion product stream is greater than is necessary to separate water, the motor/generator 7172 can produce energy, e.g., to be used by other components of the system 7100. The controller 7190 receives inputs from the various elements of the system 7100 and controls flow rates, pressures, temperatures, and/or other parameters.

The controller 7190 can also control the return of reactor products to the engine 7180. For example, the controller can direct reaction products and/or recaptured water back to the engine 7180 via a series of valves. In a particular embodiment, the controller 7190 can direct the operation of the first valve 7176a which directs hydrogen and carbon monoxide obtained from the first separator 7171a to the engine 7180 via the first conduit 7177a. These constituents can be burned in the combustion zone 7179 to provide additional power from the engine 7180. In some instances, it may be desirable to cool the combustion zone 7179 and/or other elements of the engine 7180 as shown. In such instances, the controller 7190 can control a flow of water or steam to the engine 7180 via second and third valves 7176b, 7176c and the corresponding second conduit 7177b.

In some instances, it may be desirable to balance the energy provided to the reactor 7110 with energy extracted from the engine 7180 used for other proposes. According, the system 7100 can included a proportioning valve 7187 in the combustion products stream that can direct some combustion products 7152 to a power extraction device 7188, for example, a turbo-alternator, turbocharger or a supercharger. When the power extraction device 7188 includes a supercharger, it operates to compress air entering the engine cylinder 7181 via the intake port 7184a. When the extraction device 7188 includes a turbocharger, it can include an additional fuel injection valve 7189b that directs fuel into the mixture of combustion products for further combustion to produce additional power. This power can supplement the power provided by the engine 7180, or it can be provided separately, e.g., via a separate electrical generator.

As is evident from the forgoing discussion, one feature of the system 7100 is that it is specifically configured to conserve and reuse energy from the combustion products 7152. Accordingly, the system 7100 can include additional features that are designed to reduce energy losses from the combustion products 7152. Such features can include insulation positioned around the cylinder 7181, at the head of the piston 7182, and/or at the ends of the valves 7183a, 7183b. Accordingly, the insulation prevents or at least restricts heat from being conveyed away from the engine 7180 via any thermal channel other than the passage 7118.

One feature of at least some of the foregoing embodiments is that the reactor system can include a reactor and an engine linked in an interdependent manner. In particular, the engine can provide waste heat that facilitates a dissociation process conducted at the reactor to produce a hydrogen-based fuel and a non-hydrogen based structural building block. The building block can include a molecule containing carbon, boron, nitrogen, silicon and/or sulfur, and can be used to form an architectural construct. Representative examples of architectural constructs, in addition to the polymers and composites described above are described in further detail in co-pending U.S. application Ser. No. 12/027,214, previously incorporated herein by reference. An advantage of this arrangement is that it can provide a synergy between the engine and the reactor. For example, the energy inputs normally required by the reactor to conduct the dissociation processes described above can be reduced by virtue of the additional energy provided by the combustion product. The efficiency of the engine can be improved by adding clean-burning hydrogen to the combustion chamber, and/or by providing water (e.g., in steam or liquid form) for cooling the engine. Although both the steam and the hydrogen-based fuel are produced by the reactor, they can be delivered to the engine at different rates and/or can vary in accordance with different schedules and/or otherwise in different manners.

Still further embodiments of suitable reactors with using engine heat are disclosed in pending U.S. application Ser. No. 13/027,198, filed Feb. 14, 2011, and incorporated herein by reference.

4.8 Representative Exothermic/Endothermic Reactors

Figure 24:
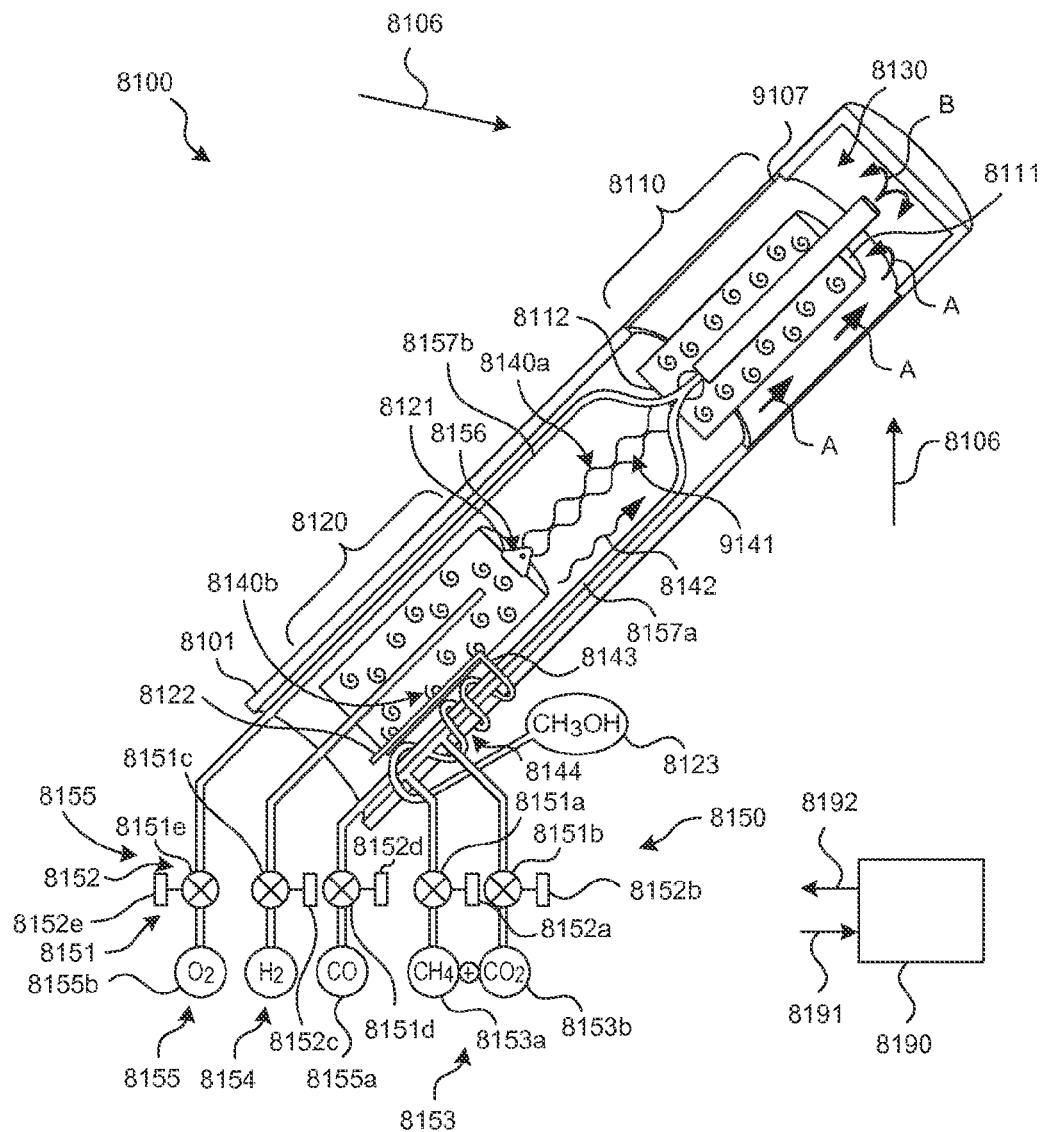
FIG. 24 is a partially schematic, cross-sectional illustration of a reactor having interacting endothermic and exothermic reaction zones in accordance with an embodiment of the disclosure.

FIG. 24 is a partially schematic, cross-sectional illustration of particular components of the system 8100, including the reactor vessel 8101. The reactor vessel 8101 includes the first reaction zone 8110 positioned toward the upper left of FIG. 24 (e.g., at a first reactor portion) to receive incident solar radiation 8106, e.g., through a solar transmissive surface 8107. The second reaction zone 8120 is also positioned within the reactor vessel 8101, e.g., at a second reactor portion, to receive products from the first reaction zone 8110 and to produce an end product, for example, methanol. Reactant sources 8153 provide reactants to the reactor vessel 8101, and a product collector 8123 collects the resulting end product. A regulation system 8150, which can include valves 8151 or other regulators and corresponding actuators 8152, is coupled to the reactant sources 8153 to control the delivery of reactants to the first reaction zone 8110 and to control other flows within the system 8100. In other embodiments, the valves can be replaced by or supplemented with other mechanisms, e.g., pumps.

In a particular embodiment, the reactant sources 8153 include a methane source 8153a and a carbon dioxide source 8153b. The methane source 8153a is coupled to a first reactant valve 8151a having a corresponding actuator 8152a, and the carbon dioxide source 8153b is coupled to a second reactant valve 8151b having a corresponding actuator 8152b. The reactants pass into the reaction vessel 8101 and are conducted upwardly around the second reaction zone 8120 and the first reaction zone 8110 as indicated by arrows A. As the reactants travel through the reactor vessel 8101, they can receive heat from the first and second reaction zones 8110, 8120 and from products passing from the first reaction zone 8110 to the second reaction zone 8120, as will be described in further detail later. The reactants enter the first reaction zone 8110 at a first reactant port 8111. At the first reaction zone 8110, the reactants can undergo the following reaction:

$$CH_4 + CO_2 + HEAT \rightarrow 2CO + 2H_2 \qquad [\text{Equation R8-1}]$$

In a particular embodiment, the foregoing endothermic reaction is conducted at about 900° C. and at pressures of up to about 1,500 psi. In other embodiments, reactions with other reactants can be conducted at other temperatures at the first reaction zone 8110. The first reaction zone 8110 can include any of a variety of suitable catalysts, for example, a nickel/aluminum oxide catalyst. In particular embodiments, the reactants and/or the first reaction zone 8110 can be subjected to acoustic pressure fluctuation (in addition to the overall pressure changes caused by introducing reactants, undergoing the reaction, and removing products from the first reaction zone 8110) to aid in delivering the reactants to the reaction sites of the catalyst. In any of these embodiments, the products produced at the first reaction zone 8110 (e.g. carbon monoxide and hydrogen) exit the first reaction zone 8110 at a first product port 8112 and enter a first heat exchanger 8140a. The first products travel through the first heat exchanger 8140a along a first flow path 8141 and transfer heat to the incoming reactants traveling along a second flow path 8142. Accordingly, the incoming reactants can be preheated at the first heat exchanger 8140a, and by virtue of passing along or around the outside of the first reaction zone 8110. In particular embodiments, one or more surfaces of the first heat exchanger 8140a can include elements or materials that absorb radiation at one frequency and re-radiate it at another. Further details of suitable materials and arrangements are disclosed in Section 4.2 above.

The first products enter the second reaction zone 8120 via a second reactant port 8121 and a check valve 8156 or other flow inhibitor. The check valve 8156 is configured to allow a one-way flow of the first products into the second reaction zone 8120 when the pressure of the first products exceeds the pressure in the second reaction zone 8120. In other embodiments, the check valve 8156 can be replaced with another mechanism, e.g., a piston or pump that conveys the first products to the second reaction zone 8120.

At the second reaction zone 8120, the first products from the first reaction zone 8110 undergo an exothermic reaction, for example:

$$2CO + 2H_2 + 2'H_2 \rightarrow CH_3OH + HEAT \qquad [\text{Equation R8-2}]$$

The foregoing exothermic reaction can be conducted at a temperature of approximately 250° C. and in many cases at a pressure higher than that of the endothermic reaction in the first reaction zone 8110. To increase the pressure at the second reaction zone 8120, the system 8100 can include an additional constituent source 8154 (e.g. a source of hydrogen) that is provided to the second reaction zone 8120 via a valve 8151c and corresponding actuator 8152c. The additional constituent (e.g. hydrogen, represented by $2'H_2$ in Equation R8-2) can pressurize the second reaction zone with or without necessarily participating as a consumable in the reaction identified in Equation R8-2. In particular, the additional hydrogen may be produced at pressure levels beyond 1,500 psi, e.g., up to about 5,000 psi or more, to provide the increased pressure at the second reaction zone 8120. In a representative embodiment, the additional hydrogen may be provided in a separate dissociation reaction using methane or another reactant. For example, the hydrogen can be produced in a separate endothermic reaction, independent of the reactions at the first and second reaction zones 8110, 8120, as follows:

$$CH_4 + HEAT \rightarrow C + 2H_2 \qquad [\text{Equation R8-3}]$$

In addition to producing hydrogen for pressurizing the second reaction zone 8120, the foregoing reaction can produce carbon suitable to serve as a building block in the production of any of a variety of suitable end products, including polymers, self-organizing carbon-based structures such as graphene, carbon composites, and/or other materials. Further examples of suitable products are included in co-pending U.S. application Ser. No. 12/027,214 previously concurrently herewith and incorporated herein by reference.

The reaction at the second reaction zone 8120 can be facilitated with a suitable catalyst, for example, copper, zinc, aluminum and/or compounds including one or more of the foregoing elements. The product resulting from the reaction at the second reaction zone 8120 (e.g. methanol) is collected at the product collector 8123. Accordingly, the methanol exits the second reaction zone 8120 at a second product port 8122 and passes through a second heat exchanger 8140b. At the second heat exchanger 8140b, the methanol travels along a third flow path 8143 and transfers heat to the incoming constituents provided to the first reaction zone 8110 along a fourth flow path 8144. Accordingly, the two heat exchangers 8140a, 8140b can increase the overall efficiency of the reactions taking place in the reactor vessel 8101 by conserving and recycling the heat generated at the first and second reaction zones.

In a particular embodiment, energy is provided to the first reaction zone 8110 via the solar concentrator 8103 described above with reference to FIG. 24. Accordingly, the energy provided to the first reaction zone 8110 by the solar collector 8103 will be intermittent. The system 8100 can include a supplemental energy source that allows the reactions to continue in the absence of sufficient solar energy. In particular, the system 8100 can include a supplemental heat source 8155. For example, the supplemental heat source 8155 can include a combustion reactant source 8155a (e.g. providing carbon monoxide) and an oxidizer source 8155b (e.g. providing oxygen). The flows from the reactant source 8155a and oxidizer source 8155b are controlled by corresponding valves 8151d, 8151e, and actuators 8152d, 8152e. In operation, the reactant and oxidizer are delivered to the reactor vessel 8101 via corresponding conduits 8157a, 8157b. The reactant and oxidizer can be preheated within the reactor vessel 8101, before reaching a combustion zone 8130, as indicated by arrow B. At the combustion zone 8130, the combustion reactant and oxidizer are combusted to provide heat to the first reaction zone 8110, thus supporting the endothermic reaction taking place within the first reaction zone 8110 in the absence of sufficient solar energy. The result of the combustion can also yield carbon dioxide, thus reducing the need for carbon dioxide from the carbon dioxide source 8153*b*. The controller 8190 can control when the secondary heat source 8155 is activated and deactivated, e.g., in response to a heat or light sensor.

In another embodiment, the oxygen provided by the oxidizer source 8155*b* can react directly with the methane at the combustion zone 8130 to produce carbon dioxide and hydrogen. This in turn can also reduce the amount of carbon dioxide required at the first reaction zone 8110. Still further embodiments of suitable exothermic/endothermic reactors are disclosed in pending U.S. application Ser. No. 13/027,060, filed Feb. 14, 2011, and incorporated herein by reference.

From the foregoing, it will be appreciated that specific embodiments of the technology have been described herein for purposes of illustration, but that various modifications may be made without deviating from the technology. For example, in certain embodiments, the working fluid exiting buffer tank 421 is directed to a storage pond that stores excess heat for later retrieval. The storage pond can include an above-ground reservoir, and/or an underground reservoir. In other embodiments, wind power operates the pump 409. In still further embodiments, the geothermal heat source is located at a submerged location or below an ocean floor, with the ocean floor having methane hydrates that may serve as a donor substance for the chemical reactor. In still further embodiments, the geothermal heat source can be located in or beneath a land formation that is itself underwater, e.g., a submerged geothermal heat source, as discussed above with reference to FIG. 2E. Further embodiments include using heat pipes to transfer heat from the geothermal source to a TCP reactor. In still further embodiments, an electrolyzer can operate in conjunction with or instead of the TCP reactor 426 shown in FIG. 4 to dissociate water into hydrogen and oxygen. In yet further embodiments, the working fluid and/or the hydrogen donor can include constituents in addition to or in lieu of those described above, e.g., methanol or propane. In still further embodiments, the reactor can separate constituents via processes other than those specifically described above, e.g., thermal decomposition, electrolysis.

The methods disclosed herein include and encompass, in addition to methods of making and using the disclosed devices and systems, methods of instructing others to make and use the disclosed devices and systems. For example, a method in accordance with a particular embodiment includes heating a working fluid at the geothermal heat source, extracting a constituent from the geothermal heat source with the working fluid, separating the constituent from the working fluid, transferring heat from the working fluid to a reactor, providing a donor substance to the reactor, reacting the donor substance at the reactor using the heat provided by the working fluid, and removing a reaction product from the reactor. A method in accordance with another embodiment includes instructing such a method. Accordingly, any and all methods of use and manufacture disclosed herein also fully disclose and enable corresponding methods of instructing such methods of use and manufacture.

Certain aspects of the technology described in the context of particular embodiments may be combined or eliminated in other embodiments. For example, the elevation feature described above in the context of FIG. 3 can be applied to the arrangement shown in FIGS. 2A and 4. In particular embodiments, additional hydrogen may be obtained from natural plate tectonics phenomena. For example, olivine and limestone can react to cause state changes in iron, which can in turn react with water to produce hydrogen. This hydrogen can be collected by the working fluid. Further embodiments can include features disclosed in any of the following U.S. nonprovisional applications, each of which was filed on Aug. 13, 2012 and is incorporated herein by reference:

U.S. Ser. No. 13/584,748, titled "FUEL-CELL SYSTEMS OPERABLE IN MULTIPLE MODES FOR VARIABLE PROCESSING OF FEEDSTOCK MATERIALS AND ASSOCIATED DEVICES, SYSTEMS, AND METHODS";

U.S. Ser. No. 13/584,741, titled "SYSTEM AND METHOD FOR COLLECTING AND PROCESSING PERMAFROST GASES, AND FOR COOLING PERMAFROST";

U.S. Ser. No. 13/584,688, titled "SYSTEMS AND METHODS FOR PROVIDING SUPPLEMENTAL AQUEOUS THERMAL ENERGY";

U.S. Ser. No. 13/584,708, titled "SYSTEMS AND METHODS FOR EXTRACTING AND PROCESSING GASES FROM SUBMERGED SOURCES";

U.S. Ser. No. 13/584,749, titled "MOBILE TRANSPORT PLATFORMS FOR PRODUCING HYDROGEN AND STRUCTURAL MATERIALS, AND ASSOCIATED SYSTEMS AND METHODS"; and U.S. Ser. No. 13/584,786, titled "REDUCING AND/OR HARVESTING DRAG ENERGY FROM TRANSPORT VEHICLES, INCLUDING FOR CHEMICAL REACTORS, AND ASSOCIATED SYSTEMS AND METHODS".

Further, while advantages associated with certain embodiments of the technology have been described in the context of those embodiments, other embodiments may also exhibit such advantages, and not all embodiments need necessarily exhibit such advantages to fall within the scope of the present disclosure. Accordingly, the present disclosure and associated technology can encompass other embodiments not expressly shown or described herein.

I claim:

1. A method for heating a reactor system with a geothermal heat source, comprising:
    directing a working fluid into thermal contact with the geothermal heat source to transfer heat from the geothermal heat source to the working fluid;
    transferring heat from the working fluid to a chemical reactor;
    dissociating a constituent from a donor substance in a non-combustive chemical process at the chemical reactor, using the heat transferred from the working fluid;
    elevating the working fluid in a gas phase from a first elevation to an intermediate elevation higher than the first elevation;
    at the intermediate elevation, changing the phase of the working fluid from the gas phase to a liquid phase;
    under the force of gravity, recirculating the working fluid in the liquid phase from the intermediate elevation and into thermal contact with the geothermal heat source.

2. The method of claim 1, further comprising:
    extracting a constituent from the geothermal heat source with the working fluid; and
    separating the constituent from the working fluid.

3. The method of claim 1 wherein changing the phase of the working fluid includes cooling the working fluid.

4. The method of claim 3 wherein an outside temperature at the intermediate elevation is less than an outside temperature at the first elevation.

5. The method of claim 1 wherein changing the phase of the working fluid includes compressing the working fluid.

6. The method of claim 1 wherein the intermediate elevation is at least 500 feet above the first elevation.

7. The method of claim 1 wherein the working fluid includes ammonia.

8. The method of claim 1 wherein the working fluid includes at least one of carbon monoxide and carbon dioxide.

9. The method of claim 1 wherein the constituent includes a metal.

10. The method of claim 1 wherein the constituent includes a rare earth metal.

11. The method of claim 1 wherein the reaction product is at least one of carbon, silicon carbide, graphite, graphene, a carbon film, a ceramic, a semiconductor device, and a polymer.

12. The method of claim 1 wherein heating the working fluid includes disposing the working fluid in direct contact with the geothermal heat source.

13. The method of claim 1 wherein heating the working fluid includes directing the working fluid to exit a first conduit at an entry portion of the geothermal heat source, directing the working fluid to pass along a flowpath extending through the geothermal heat source with the working fluid being in direct contact with the geothermal heat source, and directing the working fluid to enter a second conduit at an exit portion of the geothermal source, the second conduit being spaced apart from the first conduit.

* * * * *